United States Patent
Cha

(10) Patent No.: US 10,618,953 B2
(45) Date of Patent: Apr. 14, 2020

(54) METHOD OF PREPARING AN ANTI-SERUM ALBUMIN FAB-EFFECTOR MOIETY FUSION CONSTRUCT

(71) Applicant: AprilBio Co., Ltd., Chuncheon, Gangwon-do (KR)

(72) Inventor: Sanghoon Cha, Gangwon-do (KR)

(73) Assignee: AprilBio Co., Ltd., Chuncheon, Gangwon-do (KR)

( * ) Notice: Subject to any disclaimer, the term of this patent is extended or adjusted under 35 U.S.C. 154(b) by 0 days.

(21) Appl. No.: 15/717,528

(22) Filed: Sep. 27, 2017

(65) Prior Publication Data

US 2018/0030127 A1 Feb. 1, 2018

Related U.S. Application Data

(60) Division of application No. 15/056,299, filed on Feb. 29, 2016, now Pat. No. 9,879,077, which is a continuation of application No. PCT/KR2014/008106, filed on Aug. 29, 2014.

(30) Foreign Application Priority Data

Aug. 30, 2013 (KR) .......................... 10-2013-0104112

(51) Int. Cl.
| | |
|---|---|
| C07K 16/18 | (2006.01) |
| C07K 19/00 | (2006.01) |
| C12N 15/09 | (2006.01) |
| C12N 15/63 | (2006.01) |
| C12N 15/67 | (2006.01) |
| C07K 16/46 | (2006.01) |
| C07K 14/61 | (2006.01) |
| C07K 14/535 | (2006.01) |
| C07K 14/565 | (2006.01) |
| C07K 14/765 | (2006.01) |
| A61K 38/00 | (2006.01) |
| A61K 39/00 | (2006.01) |

(52) U.S. Cl.
CPC ............ *C07K 16/18* (2013.01); *C07K 14/535* (2013.01); *C07K 14/565* (2013.01); *C07K 14/61* (2013.01); *C07K 16/46* (2013.01); *C07K 19/00* (2013.01); *C12N 15/09* (2013.01); *C12N 15/63* (2013.01); *C12N 15/67* (2013.01); *A61K 38/00* (2013.01); *A61K 2039/505* (2013.01); *C07K 14/765* (2013.01); *C07K 2317/14* (2013.01); *C07K 2317/21* (2013.01); *C07K 2317/55* (2013.01); *C07K 2317/56* (2013.01); *C07K 2317/565* (2013.01); *C07K 2317/94* (2013.01); *C07K 2319/30* (2013.01); *C07K 2319/31* (2013.01); *C07K 2319/35* (2013.01); *C07K 2319/75* (2013.01); *Y02A 50/463* (2018.01); *Y02A 50/473* (2018.01)

(58) Field of Classification Search
None
See application file for complete search history.

(56) References Cited

U.S. PATENT DOCUMENTS

2007/0059301 A1* 3/2007 Humphreys ......... C07K 16/244
424/133.1
2009/0111745 A1 4/2009 Tomlinson

FOREIGN PATENT DOCUMENTS

| JP | 2007535472 A | 12/2007 |
|---|---|---|
| JP | 2008500830 A | 1/2008 |
| KR | 10-2007-0041781 A | 4/2007 |
| KR | 10-2007-0073886 A | 7/2007 |
| KR | 10-2011-0008086 A | 1/2011 |
| KR | 10-2012-0133403 A | 12/2012 |
| WO | 2005118642 A2 | 12/2005 |
| WO | 2010063818 A2 | 6/2010 |
| WO | 2011015649 A1 | 2/2011 |
| WO | 2012158818 A2 | 11/2012 |

OTHER PUBLICATIONS

Hust et al (2007. BMC Biotechnology. 7(14), pp. 1-15 as printed.*
Smith, B. J. et al., "Prolonged in Vivo Residence Times of Antibody Fragments Associated with Albumin", Bioconjujate Chem., 2001, 12, pp. 750-756.
International Search Report for International Patent Application No. PCT/KR2014/008106, dated Dec. 2, 2014, 9 pages.
Written Opinion for International Patent Application No. PCT/KR2014/008106, dated Dec. 2, 2014, 7 pages.
Jazayeri et al., "Half-Life Extension by Fusion to the Fc Region." Therapeutic Proteins. 157(2012):157-188.
Sogaard et al. "Treatment with Tumor-Reactive Fab-IL-2 and Fab-Staphylococcal Enterotoxin A Fusion Proteins Leads to Sustained T Cell Activation, and Long-Term Survival of Mice with Established Tumors." International Journal of Oncology. 15.5(1999):873-882.

(Continued)

*Primary Examiner* — Zachary C Howard
(74) *Attorney, Agent, or Firm* — Mintz Levin Cohn Ferris Glovsky and Popeo, P.C.

(57) ABSTRACT

The present invention relates to antigen-binding fragment (Fab) and a Fab-effector fusion protein or polypeptide comprising thereof. The Fab of the present invention specifically binds to serum albumin and thereby has extended in vivo half-life. The Fab of the present invention is characterized by not having cysteine residues that are responsible for the interchain disulfide bond in $C_{H1}$ domain and C kappa L domain as well. The Fab-effector fusion protein or polypeptide of the present invention can be produced in periplasm of *E. coli* with high yield, and has increased in vivo half-life. Further, the present invention provides *E. coli* strain which produces various kinds of Fab-effector fusion proteins or polypeptides, and a pharmaceutical composition comprising the fab-effector fusion proteins or polypeptides.

16 Claims, 38 Drawing Sheets

Specification includes a Sequence Listing.

(56) References Cited

OTHER PUBLICATIONS

Sexton et al. "Resistive-Pulse Studies of Proteins and Protein/Antibody Complexes Using a Conical Nanotube Sensor." Journal of the American Chemical Society. 129.43(2007):13144-13152.
Holt et al. "Anti-Serum Albumin Domain Antibodies for Extending the Half-Lives of Short Lived Drugs." Protein Engineering, Design and Selection. 21(2008):283-288.
Osborn et al. "Albutropin: A Growth Hormone-Albumin Fusion with Improved Pharmacokinetics and Pharmacodynamics in Rats and Monkeys." European Journal of Pharmacology, Elsevier Science, NL. 456, No. 1-3 (2002):149-158.
Kang et al. "Isolation of Human Anti-Serum Albumin Fab Antibodies with an Extended Serum-Half Life." Immunology Letters. 169(2015):33-40.
Office Action dated Mar. 21, 2017 in corresponding Japanese Application No. 2016-538860.
Search Report dated Feb. 27, 2017 in corresponding European Patent Application No. 14839630.2.

\* cited by examiner

FIG. 4

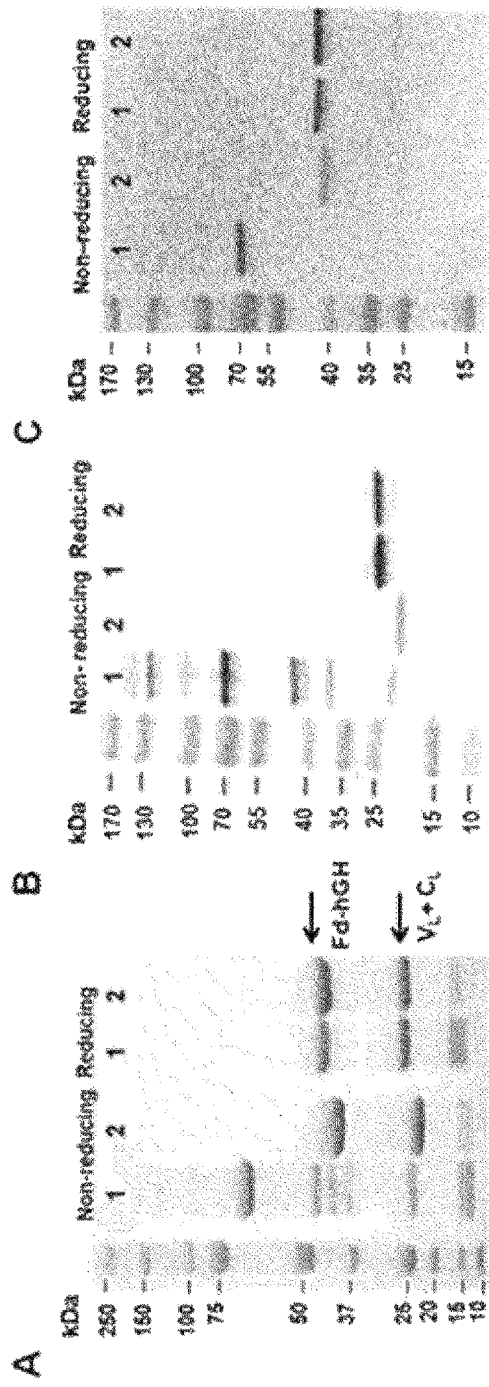

FIG. 19 pHEKA sequence (5240 bp)

[sequence text illegible]

1) SL335$_{wt}$-hGH

| | | |
|---|---|---|
| Heavy chain (Hcys + hGH format) | DNA | CAAGTTCAGCTGGTTCAGAGCGGTGGCGGCCCGGTGAAACCAGGTGGCAGCCTGCG TCTGTCCTGCGCGGCGAGCGGTTTTATGTTTCGTGCGTATAGCATGAACTGGGTGCG CCAGGCGCCGGGCAAAGGCCTGGAATGGGTGAGCAGCATTAGCAGCAGTGGCCGC TATATTCATTATGCCGACAGTGTTAAAGGTCGTTTTACCATTTCTCGTGACAATGCG AAAAACAGCCTGTATCTGCAAATGAATAGCCTGCGCGCGGAAGACACCGCGGTGTA CTACTGTGCGCGCGAAACCGTGATGGCGGGCAAAGCACTGGATTATTGGGGTCAGG GCACCCTGGTGACCGTGAGCAGCGCGAGCACCAAAGGCCCGAGCGCGAGCACCAA AGGCCCGAGCGTGTTTCCGCTGGCACCTAGTTCGAAATCAACGAGCGGTGGCACCG CGGCTCTGGGCTGCCTGGTGAAAGATTATTTCCCGGAACCTGTTACCGTGAGCTGGA ACAGCGGTGCGTTGACGAGTGGTGTGCATACCTTTCCCGCAGTTCTGCAATCGAGC GGCCTGTACTCACTGAGCAGCGTGGTTACGGTCCCGAGCAGTAGCCTGGGTACACA GACCTATATTTGTAACGTGAACCACAAGCCTTCGAACACGAAAGTTGACAAACGCG TGGAACCGAAGAGCTGCGGTTCTGCACCAGCTCCTGGATCTTTTCCGACCATTCCGC TGAGCCGCCTGTTCGATAACGCGATGCTGCGCGCCCACCGCCTGCATCAACTGGCCT TTGATACCTATCAGGAGTTTGAGGAAGCGTACATCCCGAAGGAACAGAAATATTCT TTTCTGCAGAACCCACAGACGAGCCTGTGCTTTAGCGAATCTATCCCGACCCCGTCC AACCGCGAAGAAACCCAACAGAAGTCTAACCTGGAACTGCTGCGTATCTCTCTGCT GCTGATTCAATCCTGGCTGGAACCGGTTCAATTTCTGCGTAGCGTGTTTGCGAACTC TCTGGTGTATGGCGCGTCTGACTCTAACGTGTATGACCTGCTGAAAGATCTGGAAG AAGGCATCCAAACTCTGATGGGCCGTCTGGAGGACGGCTCTCCACGTACCGGCCAG ATCTTTAAACAGACCTATAGCAAATTTGACACCAATTCTCACAACGATGATGCGCTG CTGAAAAACTATGGCCTGCTGTATTGCTTCCGTAAAGACATGGATAAAGTTGAAAC GTTCCTGCGCATTGTTCAGTGCCGTTCCGTGGAGGGCTCCTGCGGCTTC |
| | Amino acid | QVQLVQSGGGPVKPGGSLRLSCAASGFMFRAYSMNWVRQAPGKGLEWVSSISSS GRYIHYADSVKGRFTISRDNAKNSLYLQMNSLRAEDTAVYYCARETVMAGKALDYW GQGTLVTVSSASTKGPSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKRVEPKS CGSAPAPGSFPTIPLSRLFDNAMLRAHRLHQLAFDTYQEFEEAYIPKEQKYSFLQNPQTS LCFSESIPTPSNREETQQKSNLELLRISLLLIQSWLEPVQFLRSVFANSLVYGASDSNVYD LLKDLEEGIQTLMGRLEDGSPRTGQIFKQTYSKFDTNSHNDDALLKNYGLLYCFRKDM DKVETFLRIVQCRSVEGSCGF |
| Light chain (Lcys format) | DNA | GATATCGTTCTGACCCAATCTCCGGGTACGCTGAGCCTGAGCCCGGGCGAAACCGC GACCCTGAGCTGCCGCGCGAGCCAAAGCGTGGGTTCTAATCTGGCTTGGTATCAGC AGAAACCGGGTCAGGCCCCGCGCCTGCTGATCTATGGGGCGAGCACGGGGGCTACC GGCGTTCCGGCGCGCTTTAGTGGCAGTCGCAGCGGCACCGATTTTACCCTGACCATT ACAAGTCTGCAGCCGGAAGATTTTGCGACCTATTATTGCCAGCAATATTATAGCTTC CTGGCGAAAACCTTTGGTCAGGGCACCCAGCTGGAAATTAAACGCACCGTGGCGGC ACCCAGCGTGACGGTGGCGGCACCCAGCGTGTTTATTTTTCCTCCCAGTGATGAACA GCTGAAAAGCGGGACCGCGAGTGTTGTGTGCCTGTTGAACAACTTCTATCCTCGCG AAGCGAAAGTGCAGTGGAAAGTGGATAACGCATTGCAGAGCGGCAACAGTCAGGA AAGCGTTACTGAACAGGATAGCAAAGATAGTACGTACAGCTTGAGCAACACTCTGA CCCTGAGTAAAGCGGATTATGAAAAACATAAAGTGTATGCATGCGAAGTTACGCAT CAGGGGCTGAGCAGTCCGGTGACAAAGAGCTTTAACCGCGGCGAATGC |
| | Amino acid | DIVLTQSPGTLSLSPGETATLSCRASQSVGSNLAWYQQKPGQAPRLLIYGASTGATGVP ARFSGSRSGTDFTLTITSLQPEDFATYYCQQYYSFLAKTFGQGTQLEIKRTVAAPSVTVA APSVFIFPPSDEQLKSGTASVVCLLNNFYPREAKVQWKVDNALQSGNSQESVTEQDSKD STYSLSNTLTLSKADYEKHKVYACEVTHQGLSSPVTKSFNRGEC |

*The linker and the effector domains were underlined and CDRs were written in bold.

FIG. 22B

2) SL335$_{\Delta ds}$-hGH

| | | |
|---|---|---|
| Heavy chain (Hser + hGH format) | DNA | CAAGTTCAGCTGGTTCAGAGCGGTGGCGGCCCGGTGAAACCAGGTGGCAGCCTGCGT
CTGTCCTGCGCGGCGAGCGGTTTTATGTTTCGTGCGTATAGCATGAACTGGGTGCGCC
AGGCGCCGGGCAAAGGCCTGGAATGGGTGAGCAGCATTAGCAGCAGTGGCCGCTAT
ATTCATTATGCCGACAGTGTTAAAGGTCGTTTTACCATTTCTCGTGACAATGCGAAAA
ACAGCCTGTATCTGCAAATGAATAGCCTGCGCGCGGAAGACACCGCGGTGTACTACT
GTGCGCGCGAAACCGTGATGGCGGGCAAAGCACTGGATTATTGGGGTCAGGGCACCC
TGGTGACCGTGAGCAGCGCGAGCACCAAAGGCCCGAGCGCGAGCACCAAAGGCCCG
AGCGTGTTTCCGCTGGCACCTAGTTCGAAATCAACGAGCGGTGGCACCGCGGCTCTG
GGCTGCCTGGTGAAAGATTATTTCCCGGAACCTGTTACCGTGAGCTGGAACAGCGGT
GCGTTGACGAGTGGTGTGCATACCTTTCCGCAGTTCTGCAATCGAGCGGCCTGTACT
CACTGAGCAGCGTGGTTACGGTCCCGAGCAGTAGCCTGGGTACACAGACCTATATTT
GTAACGTGAACCACAAGCCTTCGAACACGAAAGTTGACAAACGCGTGGAACCGAAG
AGCAGCGGTTCTGCACCAGCTCCTGGATCTTTTCCGACCATTCCGCTGAGCCGCCTGT
TCGATAACGCGATGCTGCGCGCCCACCGCCTGCATCAACTGGCCTTTGATACCTATCA
GGAGTTTGAGGAAGCGTACATCCCGAAGGAACAGAAATATTCTTTTCTGCAGAACCC
ACAGACGAGCCTGTGCTTTAGCGAATCTATCCCGACCCCGTCCAACCGCGAAGAAAC
CCAACAGAAGTCTAACCTGGAACTGCTGCGTATCTCTCTGCTGCTGATTCAATCCTGG
CTGGAACCGGTTCAATTTCTGCGTAGCGTGTTTGCGAACTCTCTGGTGTATGGCGCGT
CTGACTCTAACGTGTATGACCTGCTGAAAGATCTGGAAGAAGGCATCCAAACTCTGA
TGGGCCGTCTGGAGGACGGCTCTCCACGTACCGGCCAGATCTTTAAACAGACCTATA
GCAAATTTGACACCAATTCTCACAACGATGATGCGCTGCTGAAAAACTATGGCCTGCT
GTATTGCTTCCGTAAAGACATGGATAAAGTTGAAACGTTCCTGCGCATTGTTCAGTGC
CGTTCCGTGGAGGGCTCCTGCGGCTTC |
| | Amino acid | QVQLVQSGGGPVKPGGSLRLSCAASGFMFRAYSMNWVRQAPGKGLEWVSS**ISSSGRY
IHYADSVKGRFTISRDNAKNSLYLQMNSLRAEDTAVYYCARETVMAGKALDY**WGQG
TLVTVSSASTKGPSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSSGSAPA
PGSFPTIPLSRLFDNAMLRAHRLHQLAFDTYQEFEEAYIPKEQKYSFLQNPQTSLCFSESIPT
PSNREETQQKSNLELLRISLLLIQSWLEPVQFLRSVFANSLVYGASDSNVYDLLKDLEEGI
QTLMGRLEDGSPRTGQIFKQTYSKFDTNSHNDDALLKNYGLLYCFRKDMDKVETFLRIV
QCRSVEGSCGF |
| Light chain (Lser format) | DNA | GATATCGTTCTGACCCAATCTCCGGGTACGCTGAGCCTGAGCCCGGGCGAAACCGCG
ACCCTGAGCTGCCGCGCGAGCCAAAGCGTGGGTTCTAATCTGGCTTGGTATCAGCAG
AAACCGGGTCAGGCCCCGCGCCTGCTGATCTATGGGGCGAGCACGGGGGCTACCGGC
GTTCCGGCGCGCTTTAGTGGCAGTCGCAGCGGCACCGATTTTACCCTGACCATTACAA
GTCTGCAGCCGGAAGATTTTGCGACCTATTATTGCCAGCAATATTATAGCTTCCTGGC
GAAAACCTTTGGTCAGGGCACCCAGCTGGAAATTAAACGCACCGTGGCGGCACCCAG
CGTGACGGTGGCGGCACCCAGCGTGTTTATTTTCCTCCCAGTGATGAACAGCTGAAA
AGCGGGACCGCGAGTGTTGTGTGCCTGTTGAACAACTTCTATCCTCGCGAAGCGAAA
GTGCAGTGGAAAGTGGATAACGCATTGCAGAGCGGCAACAGTCAGGAAAGCGTTACT
GAACAGGATAGCAAAGATAGTACGTACAGCTTGAGCAACACTCTGACCCTGAGTAAA
GCGGATTATGAAAAACATAAAGTGTATGCATGCGAAGTTACGCATCAGGGGCTGAGC
AGTCCGGTGACAAAGAGCTTTAACCGCGGCGAAAGC |
| | Amino acid | DIVLTQSPGTLSLSPGETATLSCRASQSVGSNLAWYQQKPGQAPRLLIYGASTGATGVPA
RFSGSRSGTDFTLTITSLQPEDFATYYCQQYYSFLAKTFGQGTQLEIKRTVAAPSVTVAAP
SVFIFPPSDEQLKSGTASVVCLLNNFYPREAKVQWKVDNALQSGNSQESVTEQDSKDSTY
SLSNTLTLSKADYEKHKVYACEVTHQGLSSPVTKSFNRGES |

*The linker and the effector domains were underlined and CDRs were written in bold.

FIG. 22C

3) SL335$_{wt}$-GCSF

| | | |
|---|---|---|
| Heavy chain (Hcys + GCSF format) | DNA | CAAGTTCAGCTGGTTCAGAGCGGTGGCGGCCCGGTGAAACCAGGTGGCAGCCTGCGT CTGTCCTGCGCGGCGAGCGGTTTTATGTTTCGTGCGTATAGCATGAACTGGGTGCGC AGGCGCCGGGCAAAGGCCTGGAATGGGTGAGCAGCATTAGCAGCAGTGGCCGCTAT ATTCATTATGCCGACAGTGTTAAAGGTCGTTTTACCATTTCTCGTGACAATGCGAAAA ACAGCCTGTATCTGCAAATGAATAGCCTGCGCGCGGAAGACACCGCGGTGTACTACT GTGCGCGCGAAACCGTGATGGCGGGCAAAGCACTGGATTATTGGGGTCAGGGCACCC TGGTGACCGTGAGCAGCGCGAGCACCAAAGGCCCGAGCGCGAGCACCAAAGGCCCG AGCGTGTTTCCGCTGGCACCTAGTTCGAAATCAACGAGCGGTGGCACCGCGGCTCTG GGCTGCCTGGTGAAAGATTATTTCCCGGAACCTGTTACCGTGAGCTGGAACAGCGGT GCGGTTGACGAGTGGTGTGCATACCTTTCCCGCAGTTCTGCAATCGAGCGGCCTGTACT CACTGAGCAGCGTGGTTACGGTCCCGAGCAGTAGCCTGGGTACACAGACCTATATTT GTAACGTGAACCACAAGCTTCGAACACGAAAGTTGACAAACGCGTGGAACCGAAG AGCTGCGGTTCTGCACCAGCTCCTGGATCTGCGCCTACCTATCGCGCGAGCAGCCTGC CGCAGTCGTTTCTGCTGAAAAGCCTGGAACAGGTGCGCAAGATTCAGGGTGACGGCG CAGCTCTGCAAGAAAAACTGTGCGCGACCTACAAATTGTGCCACCCTGAGGAACTGG TTCTGCTGGGCCATAGTCTGGGCATTCCGTGGGCGCCGCTGAGCAGCTGCCCGTCGCA GGCATTGCAGCTGGCTGGCTGTCTGAGCCAGTTACATAGCGGTCTGTTTCTGTATCAG GGCCTGCTGCAAGCGCTGGAAGGCATCAGTCCTGAGTTGGGTCCGACCCTGGATACC TTACAGCTGGATGTGGCGGATTTCGCAACCACCATTTGGCAGCAGATGGAAGAATTG GGCATGGCTCCGGCGTTGCAGCCGACCCAGGGCGCGATGCCTGCGTTTGCAAGCGCT TTTCAGCGCCGCGCGGGTGGGGTGCTGGTGGCGTCGCACTTGCAGAGCTTCCTGGAA GTGAGCTACCGTGTCCTGCGCCATCGGCACAGCCT |
| | Amino acid | QVQLVQSGGGPVKPGGSLRLSCAASGFMFRAYSMNWVRQAPGKGLEWVSSISSSG RYIHYADSVKGRFTISRDNAKNSLYLQMNSLRAEDTAVYYCARETVMAGKALDY WGQGTLVTVSSASTKGPSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKRVEPKSC GSAPAPGSAPTYRASSLPQSFLLKSLEQVRKIQGDGAALQEKLCATYKLCHPEELVLLGHS LGIPWAPLSSCPSQALQLAGCLSQLHSGLFLYQGLLQALEGISPELGPTLDTLQLDVADFA TTIWQQMEELGMAPALQPTQGAMPAFASAFQRRAGGVLVASHLQSFLEVSYRVLRHLA QP |
| Light chain (Lcys format) | DNA | GATATCGTTCTGACCCAATCTCCGGGTACGCTGAGCCTGAGCCCGGGCGAAACCGCG ACCCTGAGCTGCCGCGCGAGCCAAAGCGTGGGTTCTAATCTGGCTTGGTATCAGCAG AAACCGGGTCAGGCCCCGCGCCTGCTGATCTATGGGGCGAGCACGGGGGCTACCGGC GTTCCGGCGCGCTTTAGTGGCAGTCGCAGCGGCACCGATTTTACCCTGACCATTACAA GTCTGCAGCCGGAAGATTTTGCGACCTATTATTGCCAGCAATATTATAGCTTCCTGGC GAAAACCTTTGGTCAGGGCACCCAGCTGGAAATTAAACGCACCGTGGCGGCACCCAG CGTGACGGTGGCGGCACCCAGCGTGTTTATTTTCCTCCAGTGATGAACAGCTGAAA AGCGGGACCGCGAGTGTTGTGTGCCTGTTGAACAACTTCTATCCTCGCGAAGCGAAA GTGCAGTGGAAAGTGGATAACGCATTGCAGACGGCAACAGTCAGGAAAGCGTTACT GAACAGGATAGCAAAGATAGTACGTACAGCTTGAGCAACACTCTGACCCTGAGTAAA GCGGATTATGAAAAACATAAAGTGTATGCATGCGAAGTTACGCATCAGGGGCTGAGC AGTCCGGTGACAAAGAGCTTTAACCGCGGCGAATGC |
| | Amino acid | DIVLTQSPGTLSLSPGETATLSCRASQSVGSNLAWYQQKPGQAPRLLIYGASTGATGVPA RFSGSRSGTDFTLTITSLQPEDFATYYCQQYYSFLAKTFGQGTQLEIKRTVAAPSVTVAAP SVFIFPPSDEQLKSGIASVVCLLNNFYPREAKVQWKVDNALQSGNSQESVTEQDSKDSTY SLSNTLTLSKADYEKHKVYACEVTHQGLSSPVTKSFNRGEC |

*The linker and the effector domains were underlined and CDRs were written in bold.

FIG. 22D

4) SL335$_{\Delta ds}$-GCSF

| | | |
|---|---|---|
| Heavy chain (Hser + GCSF format) | DNA | CAAGTTCAGCTGGTTCAGAGCGGTGGCGGCCCGGTGAAACCAGGTGGCAGCCTGCGT<br>CTGTCCTGCGCGGCGAGCGGTTTTATGTTTCGTGCGTATAGCATGAACTGGGTGCGCC<br>AGGCGCCGGGCAAAGGCCTGGAATGGGTGAGCAGCATTAGCAGCAGTGGCCGCTAT<br>ATTCATTATGCCGACAGTGTTAAAGGTCGTTTTACCATTTCTCGTGACAATGCGAAAA<br>ACAGCCTGTATCTGCAAATGAATAGCCTGCGCGCGGAAGACACCGCGGTGTACTACT<br>GTGCGCGCGAAACCGTGATGGCGGGCAAAGCACTGGATTATTGGGGTCAGGGCACCC<br>TGGTGACCGTGAGCAGCGCGAGCACCAAAGGCCCGAGCGCGAGCACCAAAGGCCCG<br>AGCGTGTTTCCGCTGGCACCTAGTTCGAAATCAACGAGCGGTGGCACCGCGGCTCTG<br>GGCTGCCTGGTGAAAGATTATTTCCCGGAACCTGTTACCGTGAGCTGGAACAGCGGT<br>GCGTTGACGAGTGGTGTGCATACCTTTCCCGCAGTTCTGCAATCGAGCGGCCTGTACT<br>CACTGAGCAGCGTGGTTACGGTCCCGAGCAGTAGCCTGGGTACACAGACCTATATTT<br>GTAACGTGAACCACAAGCCTTCGAACACGAAAGTTGACAAACGCGTGGAACCGAAG<br>AGCAGCGGTTCTGCACCAGCTCCTGGATCTGCGCCTACCTATCGCGCGAGCAGCCTGC<br>CGCAGTCGTTTCTGCTGAAAAGCCTGGAACAGGTGCGCAAGATTCAGGGTGACGGCG<br>CAGCTCTGCAAGAAAAACTGTGCGCGACCTACAAATTGTGCCACCCTGAGGAACTGG<br>TTCTGCTGGGCCATAGTCTGGGCATTCCGTGGGCGCCGCTGAGCAGCTGCCCGTCGCA<br>GGCATTGCAGCTGGCTGGCTGTCTGAGCCAGTTACATAGCGGTCTGTTTCTGTATCAG<br>GGCCTGCTGCAAGCGCTGGAAGGCATCAGTCCTGAGTTGGGTCCGACCCTGGATACC<br>TTACAGCTGGATGTGGCGGATTTCGCAACCACCATTTGGCAGCAGATGGAAGAATTG<br>GGCATGGCTCCGGCGTTGCAGCCGACCCAGGGCGCGATGCCTGCGTTTGCAAGCGCT<br>TTTCAGCGCCGCGCGGGTGGGGTGCTGGTGGCGTCGCACTTGCAGAGCTTCCTGGAA<br>GTGAGCTACCGTGTCCTGCGCCATCGGCACAGCCT |
| | Amino acid | QVQLVQSGGGPVKPGGSLRLSCAASGFMFRAYSMNWVRQAPGKGLEWVSSISSSGRY IHYADSVKGRFTISRDNAKNSLYLQMNSLRAEDTAVYYCARETVMAGKALDYWGQGTL VTVSSASTKGPSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRVEPKSSGSAPAPG SAPTYRASSLPQSFLLKSLEQVRKIQGDGAALQEKLCATYKLCHPEELVLLGHSLGIPWAP LSSCPSQALQLAGCLSQLHSGLFLYQGLLQALEGISPELGPTLDTLQLDVADFATTIWQQM EELGMAPALQPTQGAMPAFASAFQRRAGGVLVASHLQSFLEVSYRVLRHLAQP |
| Light chain (Lser format) | DNA | GATATCGTTCTGACCCAATCTCCGGGTACGCTGAGCCTGAGCCCGGGCGAAACCGCG<br>ACCCTGAGCTGCCGCGCGAGCCAAAGCGTGGGTTCTAATCTGGCTTGGTATCAGCAG<br>AAACCGGGTCAGGCCCCGCGCCTGCTGATCTATGGGGCGAGCACGGGGGCTACCGGC<br>GTTCCGGCGCGCTTTAGTGGCAGTCGCAGCGGCACCGATTTTACCCTGACCATTACAA<br>GTCTGCAGCCGGAAGATTTTGCGACCTATTATTGCCAGCAATATTATAGCTTCCTGGC<br>GAAAACCTTTGGTCAGGGCACCCAGCTGGAAATTAAACGCACCGTGGCGGCACCCAG<br>CGTGACGGTGGCGGCACCCAGCGTGTTTATTTTTCCTCCCAGTGATGAACAGCTGAAA<br>AGCGGGACCGCGAGTGTTGTGTGCCTGTTGAACAACTTCTATCCTCGCGAAGCGAAA<br>GTGCAGTGGAAAGTGGATAACGCATTGCAGAGCGGCAACAGTCAGGAAAGCGTTACT<br>GAACAGGATAGCAAAGATAGTACGTACAGCTTGAGCAACACTCTGACCCTGAGTAAA<br>GCGGATTATGAAAAACATAAAGTGTATGCATGCGAAGTTACGCATCAGGGGCTGAGC<br>AGTCCGGTGACAAGAGCTTTAACCGCGGCGAAAGC |
| | Amino acid | DIVLTQSPGTLSLSPGETATLSCRASQSVGSNLAWYQQKPGQAPRLLIYGASTGATGVPA RFSGSRSGTDFTLTITSLQPEDFATYYCQQYYSFLAKTFGQGTQLEIKRTVAAPSVTVAAP SVFIFPPSDEQLKSGTASVVCLLNNFYPREAKVQWKVDNALQSGNSQESVTEQDSKDSTY SLSNTLTLSKADYEKHKVYACEVTHQGLSSPVTKSFNRGES |

*The linker and the effector domains were underlined and CDRs were written in bold.

FIG. 22E

5) SL335$_{wt}$-IFNβ

| | | |
|---|---|---|
| Heavy chain (Hcys + IFNβ formt) | DNA | CAAGTTCAGCTGGTTCAGAGCGGTGGCGGCCCGGTGAAACCAGGTGGCAGCCTGCGT CTGTCCTGCGCGGCGAGCGGTTTTATGTTTCGTGCGTATAGCATGAACTGGGTGCGC AGGCGCCGGGCAAAGGCCTGGAATGGGTGAGCAGCATTAGCAGCAGTGGCCGCTAT ATTCATTATGCCGACAGTGTTAAAGGTCGTTTTACCATTTCTCGTGACAATGCGAAAA ACAGCCTGTATCTGCAAATGAATAGCCTGCGCGCGGAAGACACCGCGGTGTACTACT GTGCGCGCGAAACCGTGATGGCGGGCAAAGCACTGGATTATTGGGGTCAGGGCACCC TGGTGACCGTGAGCAGCGCGAGCACCAAAGGCCCGAGCGCGAGCACCAAAGGCCCG AGCGTGTTTCCGCTGGCACCTAGTTCGAAATCAACGAGCGGTGGCACCGCGGCTCTG GGCTGCCTGGTGAAAGATTATTTCCCGGAACCTGTTACCGTGAGCTGGAACAGCGGT GCGTTGACGAGTGGTGTGCATACCTTTCCGCAGTTCTGCAATCGAGCGGCCTGTACT CACTGAGCAGCGTGGTTACGGTCCCGAGCAGTAGCCTGGGTACACAGACCTATATTT GTAACGTGAACCACAAGCCTTCGAACACGAAAGTTGACAAACGCGTGGAACCGAAG AGCTGCGGTTCTGCACCAGCTCCTGGATCTTCATACAACCTGCTGGGCTTCCTGCAAC GTAGCAGTAACTTTCAGAGCCAGAAGCTGTTATGGCAACTGAACGGCCGCCTGGAGT ACTGCCTGAAGGATCGCATGAACTTTGATATTCCGGAAGAAATTAAACAGCTGCAAC AGTTCCAGAAAGAAGATGCGGCGCTGACCATTTATGAAATGCTGCAAAACATTTTTG CGATTTTTCGCCAAGATAGTAGTAGCACCGGCTGGAACGAAACCATTGTGGAAACC TGCTCGCCAACGTGTACCATCAGATTAACCACCTGAAGACCGTGCTGGAAGAAAAAC TGGAAAAAGAAGATTTTACCCGCGGCAAACTGATGAGCAGCCTGCATCTGAAACGCT ATTATGGCCGCATTCTCCATTATCTGAAAGCCAAAGAGTATTCCCACTGTGCTTGGAC CATTGTTCGCGTGGAAATTCTGCGCAACTTTTATTTTATTAACCGCCTGACCGGCTATC TGCGCAAC |
| | Amino acid | QVQLVQSGGGPVKPGGSLRLSCAASGFMFRAYSMNWVRQAPGKGLEWVSSISSSGRYIH YADSVKGRFTISRDNAKNSLYLQMNSLRAEDTAVYYCARETVMAGKALDYWGQGTLV TVSSASTKGPSASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEPKSCGSAPAPGS SYNLLGFLQRSSNFQSQKLLWQLNGRLEYCLKDRMNFDIPEEIKQLQQFQKEDAALTIYE MLQNIFAIFRQDSSSTGWNETIVENLLANVYHQINHLKTVLEEKLEKEDFTRGKLMSSLHL KRYYGRILHYLKAKFYSHCAWTIVRVFILRNFYFINRLTGYLRN |
| Light chain (Lcys format) | DNA | GATATCGTTCTGACCCAATCTCCGGGTACGCTGAGCCTGAGCCCCGGGCGAAACCGCG ACCCTGAGCTGCCGCGCGAGCCAAAGCGTGGGTTCTAATCTGGCTTGGTATCAGCAG AAACCGGGTCAGGCCCCGCGCCTGCTGATCTATGGGGCGAGCACGGGGGCTACCGGC GTTCCGGCGCGCTTTAGTGGCAGTCGCAGCGGCACCGATTTTACCCTGACCATTACAA GTCTGCAGCCGGAAGATTTTGCGACCTATTATTGCCAGCAATATTATAGCTTCCTGGC GAAAACCTTTGGTCAGGGCACCCAGCTGGAAATTAAACGCACCGTGGCGGCACCCAG CGTGACGGTGGCGGCACCCAGCGTGTTTATTTTCCTCCCAGTGATGAACAGCTGAAA AGCGGGACCGCGAGTGTTGTGTGCCTGTTGAACAACTTCTATCCTCGCGAAGCGAAA GTGCAGTGGAAAGTGGATAACGCATTGCAGAGCGGCAACAGTCAGGAAAGCGTTACT GAACAGGATAGCAAAGATAGTACGTACGACCTTGAGCAACACTCTGACCCTGAGTAAA GCGGATTATGAAAAACATAAAGTGTATGCATGCGAAGTTACGCATCAGGGGCTGAGC AGTCCGGTGACAAAGAGCTTTAACCGCGGCGAATGC |
| | Amino acid | DIVLTQSPGTLSLSPGETATLSCRASQSVGSNLAWYQQKPGQAPRLLIYGASTGATGVPA RFSGSRSGTDFTLTITSLQPEDFATYYCQQYYSFLAKTFGQGTQLEIKRTVAAPSVTVAAP SVFIFPPSDEQLKSGTASVVCLLNNFYPREAKVQWKVDNALQSGNSQESVTEQDSKDSTY SLSNTLTLSKADYEKHKVYACEVTHQGLSSPVTKSFNRGEC |

*The linker and the effector domains were underlined and CDRs were written in bold.

FIG. 22F

6) SL335$_{\Delta ds}$-IFNβ

| | | |
|---|---|---|
| Heavy chain (Hser + IFNβ formt) | DNA | CAAGTTCAGCTGGTTCAGAGCGGTGGCGGCCCGGTGAAACCAGGTGGCAGCCTGCGT CTGTCCTGCGCGGCGAGCGGTTTTATGTTTCGTGCGTATAGCATGAACTGGGTGCGCC AGGCGCCGGGCAAAGGCCTGGAATGGGTGAGCAGCATTAGCAGCAGTGGCCGCTAT ATTCATTATGCCGACAGTGTTAAAGGTCGTTTTACCATTTCTCGTGACAATGCGAAAA ACAGCCTGTATCTGCAAATGAATAGCCTGCGCGCGGAAGACACCGCGGTGTACTACT GTGCGCGCGAAACCGTGATGGCGGGCAAAGCACTGGATTATTGGGGTCAGGGCACCC TGGTGACCGTGAGCAGCGCGAGCACCAAAGGCCCGAGCGCGAGCACCAAAGGCCCG AGCGTGTTTCCGCTGGCACCTAGTTCGAAATCAACGAGCGGTGGCACCGCGGCTCTG GGCTGCCTGGTGAAAGATTATTTCCCGGAACCTGTTACCGTGAGCTGGAACAGCGGT GCGTTGACGAGTGGTGTGCATACCTTTCCCGCAGTTCTGCAATCGAGCGGCCTGTACT CACTGAGCAGCGTGGTTACGGTCCCGAGCAGTAGCCTGGGTACACAGACCTATATTT GTAACGTGAACCACAAGCCTTCGAACACGAAAGTTGACAAACGCGTGGAACCGAAG AGCAGCGGTTCTGCACCAGCTCCTGGATCTTCATACAACCTGCTGGGCTTCCTGCAAC GTAGCAGTAACTTTCAGAGCCAGAAGCTGTTATGGCAACTGAACGGCCGCCTGGAGT ACTGCCTGAAGGATCGCATGAACTTTGATATTCCGGAAGAAATTAAACAGCTGCAAC AGTTCCAGAAAGAAGATGCGGCGCTGACCATTTATGAAATGCTGCAAAACATTTTTG CGATTTTTCGCCAAGATAGTAGTAGCACCGGCTGGAACGAAACCATTGTGGAAAACC TGCTCGCCAACGTGTACCATCAGATTAACCACCTGAAGACCGTGCTGGAAGAAAAAC TGGAAAAAGAAGATTTTACCCGCGGCAAACTGATGAGCAGCCTGCATCTGAAACGCT ATTATGGCCGCATTCTCCATTATCTGAAAGCCAAAGAGTATTCCCACTGTGCTTGGAC CATTGTTCGCGTGGAAATTCTGCGCAACTTTTATTTTATTAACCGCCTGACCGGCTATC TGCGCAAC |
| | Amino acid | QVQLVQSGGGPVKPGGSLRLSCAASGFMFRAYSMNWVRQAPGKGLEWVSSISSSGRYIH YADSVKGRFTISRDNAKNSLYLQMNSLRAEDTAVYYCARETVMAGKALDYWGQGTLV TVSSASTKGPSASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEPKSSGSAPAPGS SYNLLGFLQRSSNFQSQKLLWQLNGRLEYCLKDRMNFDIPEEIKQLQQFQKEDAALTIYE MLQNIFAIFRQDSSSTGWNETIVENLLANVYHQINHLKTVLEEKLEKEDFTRGKLMSSLHL KRYYGRILHYLKAKEYSHCAWTIVRVEILRNFYFINRLTGYLRN |
| Light chain (Lser format) | DNA | GATATCGTTCTGACCCAATCTCCGGGTACGCTGAGCCTGAGCCCGGGCGAAACCGCG ACCCTGAGCTGCCGCGCGAGCCAAAGCGTGGGTTCTAATCTGGCTTGGTATCAGCAG AAACCGGGTCAGGCCCCGCGCCTGCTGATCTATGGGGCGAGCACGGGGGCTACCGGC GTTCCGGCGCGCTTTAGTGGCAGTCGCAGCGGCACCGATTTTACCCTGACCATTACAA GTCTGCAGCCGGAAGATTTTGCGACCTATTATTGCCAGCAATATTATAGCTTCCTGGC GAAAACCTTTGGTCAGGGCACCCAGCTGGAAATTAAACGCACCGTGGCGGCACCCAG CGTGACGGTGGCGGCACCCAGCGTGTTTATTTTTCCTCCCAGTGATGAACAGCTGAAA AGCGGGACCGCGAGTGTTGTGTGCCTGTTGAACAACTTCTATCCTCGCGAAGCGAAA GTGCAGTGGAAAGTGGATAACGCATTGCAGAGCGGCAACAGTCAGGAAAGCGTTACT GAACAGGATAGCAAAGATAGTACGTACAGCTCTGAGCAACACTCTGACCCTGAGTAAA GCGGATTATGAAAAACATAAAGTGTATGCATGCGAAGTTACGCATCAGGGGCTGAGC AGTCCGGTGACAAAGAGCTTTAACCGCGGCGAAAGC |
| | Amino acid | DIVLTQSPGTLSLSPGETATLSCRASQSVGSNLAWYQQKPGQAPRLLIYGASTGATGVPA RFSGSRSGTDFTLTITSLQPEDFATYYCQQYYSFLAKTFGQGTQLEIKRTVAAPSVTVAAP SVFIFPPSDEQLKSGTASVVCLLNNFYPREAKVQWKVDNALQSGNSQESVTEQDSKDSTY SLSNTLTLSKADYEKHKVYACEVTHQGLSSPVTKSFNRGES |

*The linker and the effector domains were underlined and CDRs were written in bold.

FIG. 22G

7) EGL4$_{wt}$-hGH

| | | |
|---|---|---|
| Heavy chain (Hcys_hGH format) | DNA | GAGGTGCAGCTGGTGCAGTCTGGGGGAGGCTTGGTACAGCCTGGCAGGTCCCTGAGA<br>CTCTCCTGCACAGCCTCTGGATTCACCTTTGATGATTATGCCATGCACTGGGTCCGGC<br>AAGCTCCAGGGAAGGGCCTGGAGTGGGTCTCAGGTATTAGTTGGAATGGTGGTAGCG<br>TAGTCTATGCGGACTCTGTCAGGGGCCGATTCACCATCTCCAGAGACAACGCCAAGA<br>ACTCCCTGTATCTGCAAATGAACAGTCTGAGAACTGAGGACACGGCCGTCTATTACTG<br>TGCGAGAGATTACGGTTACTACGGTATGGACGTCTGGGGCCAAGGAACCCTGGTCAC<br>CGTCTCCTCATCGGCCACATTGGCCGCCTCCACCAAGGGCCCATCGGTCTTCCCCCTG<br>GCACCCTCCTCCAAGAGCACCTCTGAGGGCACAGCGGCCCTGGGCTGCCTGGTCAAG<br>GACTACTTCCCCGAACCGGTGACGGTGTCGTGGAACTCAGGCGCCCTGACCAGCGGC<br>GTGCACACCTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTGAATCACA<br>AGCCCAGCAACACCAAGGTGGACAAGAGAGTTGAGCCCAAATCTTGTGGTTCTGCAC<br>CAGCTCCTGGATCTTTTCCGACCATTCCGCTGAGCCGCCTGTTCGATAACGCGATGCT<br>GCGCGCCCACCGCCTGCATCAACTGGCCTTTGATACCTATCAGGAGTTTGAGGAAGC<br>GTACATCCCGAAGGAACAGAAATATTCTTTTCTGCAGAACCCACAGACGAGCCTGTG<br>CTTTAGCGAATCTATCCCGACCCCGTCCAACCGCGAAGAAACCCAACAGAAGTCTAA<br>CCTGGAACTGCTGCGTATCTCTCTGCTGCTGATTCAATCCTGGCTGGAACCGGTTCAA<br>TTTCTGCGTAGCGTGTTTGCGAACTCTCTGGTGTATGGCGCGTCTGACTCTAACGTGT<br>ATGACCTGCTGAAAGATCTGGAAGAAGGCATCCAAACTCTGATGGGCCGTCTGGAGG<br>ACGGCTCTCCACGTACCGGCCAGATCTTTAAACAGACCTATAGCAAATTTGACACCA<br>ATTCTCACAACGATGATGCGCTGCTGAAAAACTATGGCCTGCTGTATTGCTTCCGTAA<br>AGACATGGATAAAGTTGAAACGTTCCTGCGCATTGTTCAGTGCCGTTCCGTGGAGGG<br>CTCCTGCGGCTTC |
| | Amino acid | EVQLVQSGGGLVQPGRSLRLSCTASGFTFDDYAMHWVRQAPGKGLEWVSGISWNGGSV<br>VYADSVRGRFTISRDNAKNSLYLQMNSLRTEDTAVYYCARDYGYYGMDVWGQGTLVT<br>VSSSATLAASTKGPSVFPLAPSSKSTSEGTAALGCLVKDYFPEPVTVSWNSGALTSGVHTF<br>PAVLQSSGLYSLSSVVTVPSSSLGTQTYICNVNHKPSNTKVDKRVEPKSCGSAPAPGSFPTI<br>PLSRLFDNAMLRAHRLHQLAFDTYQEFEEAYIPKEQKYSFLQNPQTSLCFSESIPTPSNREE<br>TQQKSNLELLRISLLLIQSWLEPVQFLRSVFANSLVYGASDSNVYDLLKDLEEGIQTLMGR<br>LEDGSPRTGQIFKQTYSKFDTNSHNDDALLKNYGLLYCFRKDMDKVETFLRIVQCRSVEG<br>SCGF |
| Light chain (Lcys format) | DNA | GATATTGTGATGACCCAGTCTCCATCTTCCGTGTCTGCATCTGTTGGAGACAGAGTCA<br>CCATCACTTGTCGGGCGAGTCAGAATATTGGCAGCTGGTTAGCCTGGTATCAGCAGA<br>AACCAGGTAACGCCCCTAAGTTGTTGATCTATAGAGCATCCAATTTGCGAAGTGGGG<br>TCCCATCAAGGTTCAGCGGCAGTGGCTCTGGGACAGATTTCACTCTTACCATCAGCAG<br>CCTGCAGCCTGAAGATTTCGCAACTTACTTTTGTCAACAGGCTACCATTTTTCCCTCTCA<br>CTTTCGGCGGAGGGACCCGGGTGGATATCAAACGTTCTAGAGCTGTGGCTGCACCAT<br>CTGTCTTCATCTTCCCGCCATCTGATGAGCAGTTGAAATCTGGAACTGCCTCTGTTGTG<br>TGCCTGCTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAAGGACAG<br>CACCTACAGCCTCAGCAACACCCTGACGCTGAGCAAAGCAGACTACGAGAAACACAA<br>AGTCTACGCCTGCGAAGTCACCCATCAGGGCCTGAGTTCGCCCGTCACAAAGAGCTT<br>CAACAGGGGAGAGTGT |
| | Amino acid | DIVMTQSPSSVSASVGDRVTITCRASQNIGSWLAWYQQKPGNAPKLLIYRASNLRSGVPS<br>RFSGSGSGTDFTLTISSLQPEDFATYFCQQATIFPLTFGGGTRVDIKRSRTVAAPSVFIFPPS<br>DEQLKSGTASVVCLLNNFYPREAKVQWKVDNALQSGNSQESVTEQDSKDSTYSLSNTLT<br>LSKADYEKHKVYACEVTHQGLSSPVTKSFNRGEC |

*The linker and the effector domains were underlined and CDRs were written in bold.

FIG. 22H

8) EGL4$_{\Delta ds}$-hGH

<table>
<tr><td rowspan="2">Heavy chain (Hser_hGH format)</td><td>DNA</td><td>GAGGTGCAGCTGGTGCAGTCTGGGGGAGGCTTGGTACAGCCTGGCAGGTCCCTGAGA<br>CTCTCCTGCACAGCCTCTGGATTCACCTTTGATGATTATGCCATGCACTGGGTCCGGCA<br>AGCTCCAGGGAAGGGCCTGGAGTGGGTCTCAGGTATTAGTTGGAATGGTGGTAGCGT<br>AGTCTATGCGGACTCTGTCAGGGGCCGATTCACCATCTCCAGAGACAACGCCAAGAA<br>CTCCCTGTATCTGCAAATGAACAGTCTGAGAACTGAGGACACGGCCGTCTATTACTGT<br>GCGAGAGATTACGGTTACTACGGTATGGACGTCTGGGGCCAAGGAACCCTGGTCACC<br>GTCTCCTCATCGGCCACATTGGCCGCCTCCACCAAGGGCCCATCGGTCTTCCCCCTGG<br>CACCCTCCTCCAAGAGCACCTCTGAGGGCACAGCGGCCCTGGGCTGCCTGGTCAAGG<br>ACTACTTCCCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCAGCGTGGTG<br>ACCGTGCCCTCCAGCAGCTTGGGCACCCAGACCTACATCTGCAACGTGAATCACAAGC<br>CCAGCAACACCAAGGTGGACAAGAGAGTTGAGCCCAAATCTAGTGGTTCTGCACCAG<br>CTCCTGGATCTTTTCCGACCATTCCGCTGAGCCGCCTGTTCGATAACGCGATGCTGCGC<br>GCCCACCGCCTGCATCAACTGGCCTTTGATACCTATCAGGAGTTTGAGGAAGCGTACA<br>TCCCGAAGGAACAGAAATATTCTTTTCTGCAGAACCCACAGACGAGCCTGTGCTTTAG<br>CGAATCTATCCCGACCCCGTCCAACCGCGAAGAAACCCAACAGAAGTCTAACCTGGA<br>ACTGCTGCGTATCTCTCTGCTGCTGATTCAATCCTGGCTGGAACCGGTTCAATTTCTGC<br>GTAGCGTGTTTGCGAACTCTCTCTGGTGTATGGCGCGTCTGACTCTAACGTGTATGACCT<br>GCTGAAAGATCTGGAAGAAGGCATCCAAACTCTGATGGGCCGTCTGGAGGACGGCTC<br>TCCACGTACCGGCCAGATCTTTAAACAGACCTATAGCAAATTTGACACCAATTCTCAC<br>AACGATGATGCGCTGCTGAAAAACTATGGCCTGCTGTATTGCTTCCGTAAAGACATGG<br>ATAAAGTTGAAACGTTCCTGCGCATTGTTCAGTGCCGTTCCGTGGAGGGCTCCTGCGG<br>CTTC</td></tr>
<tr><td>Amino acid</td><td>EVQLVQSGGGLVQPGRSLRLSCTASGFTFDDYAMHWVRQAPGKGLEWVSGISWNGGSV<br>VYADSVRGRFTISRDNAKNSLYLQMNSLRTEDTAVYYCARDYGYYGMDVWGQGTLVT<br>VSSSATLAASTKGPSVFPLAPSSKSTSEGTAALGCLVKDYFPEPVTVSWNSGALTSGVHTF<br>PAVLQSSGLYSLSSVVTVPSSSLGTQTYICNVNHKPSNTKVDKRVEPKSSGSAPAPGSFPTI<br>PLSRLFDNAMLRAHRLHQLAFDTYQEFEEAYIPKEQKYSFLQNPQTSLCFSESIPTPSNREE<br>TQQKSNLELLRISLLLIQSWLEPVQFLRSVFANSLVYGASDSNVYDLLKDLEEGIQTLMGR<br>LEDGSPRTGQIFKQTYSKFDTNSHNDDALLKNYGLLYCFRKDMDKVETFLRIVQCRSVEG<br>SCGF</td></tr>
<tr><td rowspan="2">Light chain (Lser format)</td><td>DNA</td><td>GATATTGTGATGACCCAGTCTCCATCTTCCGTGTCTGCATCTGTTGGAGACAGAGTCA<br>CCATCACTTGTCGGGCGAGTCAGAATATTGGCAGCTGGTTAGCCTGGTATCAGCAGAA<br>ACCAGGTAACGCCCCTAAGTTGTTGATCTATAGAGCATCCAATTTGCAAGTGGGGTC<br>CCATCAAGGTTCAGCGGCAGTGGCTCTGGGACAGATTTCACTCTTACCATCAGCAGCC<br>TGCAGCCTGAAGATTTCGCAACTTACTTTTGTCAACAGGCTACCATTTTCCCTCTCACT<br>TTCGGCGGAGGGACCCGGGTGGATATCAAACGTTCTAGAGCTGTGGCTGCACCATCTG<br>TCTTCATCTTCCCGCCATCTGATGAGCAGTTGAAATCTGGAACTGCCTCTGTTGTGTGC<br>CTGCTGAATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGACAGCACC<br>TACAGCCTCAGCAACACCCTGACGCTGAGCAAAGCAGACTACGAGAAACACAAAGTC<br>TACGCCTGCGAAGTCACCCATCAGGGCCTGAGTTCGCCCGTCACAAAGAGCTTCAACA<br>GGGGAGAGAGT</td></tr>
<tr><td>Amino acid</td><td>DIVMTQSPSSVSASVGDRVTITCRASQNIGSWLAWYQQKPGNAPKLLIYRASNLRSGVPSR<br>FSGSGSGTDFTLTISSLQPEDFATYFCQQATIFPLT**FGGGTRVDIKRSRTVAAPSVFIFPPSDE<br>QLKSGTASVVCLLNNFYPREAKVQWKVDNALQSGNSQESVTEQDSKDSTYSLSNTLTLS<br>KADYEKHKVYACEVTHQGLSSPVTKSFNRGES</td></tr>
</table>

*The linker and the effector domains were underlined and CDRs were written in bold.

FIG. 22I

9) 1β28$_{wt}$-hGH

| | | |
|---|---|---|
| Heavy chain (Hcys _hGH format) | DNA | CAGGTGCAGCTGGTGCAGTCAGGGGGAGGCCTGGTCAGGCCGGGGGGGTCCCTGAG ACTCTCCTGTGCAGCCTCTGGACTCATATTCAGTAATTATAGCATGAACTGGGTCCGC CAGGCTCCGGGGAAGGGGCTGGAGTGGGTCTCATCAATAAGTAGTGCTGGTAGTTAC AAATACTACACAGACTCAGTGAAGGGCCGATTCACCATCTCCAGAGACAACGCCAAG AAGTCACTGTATCTGCAAATGAACAGCCTGAGAGTCGACGACACGGCCGTCTATTAC TGTGCAAGAGGGGACTATGATACGGGCATGGAGCCCTGGGGCCAAGGCACCATGGTC ACCGTCTCCTCATCGGCCACATTGGCCGCCTCCACCAAGGGCCCATCGGTCTTCCCCC TGGCACCCTCCTCCAAGAGCACCTCTGGGGGCACAGCGGCCCTGGGCTGCCTGGTCA AGGACTACTTCCCCGAACCGGTGACGGTGTCGTGGAACTCAGGCGCCCTGACCAGCG GCGTGCACACCTTCCCGGCTGTCCTACAGTCCTCAGGACTCTACTCCCTCAGCAGCGT GGTGACCGTGCCCTCCAGCAGCTTGGGCACCCAGACCTACATCTGCAACGTGAATCA CAAGCCCAGCAACACCAAGGTGGACAAGAGAGTTGAGCCCAAATCTTGTGGTTCTGC ACCAGCTCCTGGATCTTTTCCGACCATTCCGCTGAGCCGCCTGTTCGATAACGCGATG CTGCGCGCCCACCGCCTGCATCAACTGGCCTTTGATACCTATCAGGAGTTTGAGGAAG CGTACATCCCGAAGGAACAGAAATATTCTTTTCTGCAGAACCCACAGACGAGCCTGT GCTTTAGCGAATCTATCCCGACCCCGTCCAACCGCGAAGAAACCCAACAGAAGTCTA ACCTGGAACTGCTGCGTATCTCTCTGCTGCTGATTCAATCCTGGCTGGAACCGGTTCA ATTTCTGCGTAGCGTGTTTGCGAACTCTCTGGTGTATGGCGCGTCTGACTCTAACGTG TATGACCTGCTGAAAGATCTGGAAGAAGGCATCCAAACTCTGATGGGCCGTCTGGAG GACGGCTCTCCACGTACCGGCCAGATCTTTAAACAGACCTATAGCAAATTTGACACC AATTCTCACAACGATGATGCGCTGCTGAAAAACTATGGCCTGCTGTATTGCTTCCGTA AGACATGGATAAAGTTGAAACGTTCCTGCGCATTGTTCAGTGCCGTTCCGTGGAGG GCTCCTGCGGCTTC |
| | Amino acid | QVQLVQSGGGLVRPGGSLRLSCAASGLIFSNYSMNWVRQAPGKGLEWVSSISSAGSYKY YTDSVKGRFTISRDNAKKSLYLQMNSLRVDDTAVYYCARGDYDTGMEPWGQGTMVTV SSSATLAASTKGPSVFPLAPSSKSTSEGTAALGCLVKDYFPEPVTVSWNSGALTSGVHTFP AVLQSSGLYSLSSVVTVPSSSLGTQTYICNVNIIKPSNTKVDKRVEPKSCGSAPAPGSFPTIP LSRLFDNAMLRAHRLHQLAFDTYQEFEEAYIPKEQKYSFLQNPQTSLCFSESIPTPSNREET QQKSNLELLRISLLLIQSWLEPVQFLRSVFANSLVYGASDSNVYDLLKDLEEGIQTLMGRL EDGSPRTGQIFKQTYSKFDTNSHNDDALLKNYGLLYCFRKDMDKVETFLRIVQCRSVEGS CGF |
| Light chain (Lcys format) | DNA | GAGCTCGAGCTCGTGTCGACGCAGTCTCCATCCTCCCTGTCTGCATCTGTGGGAGACA GAGTCACCATTACTTGCCGGGCAAGTCAGAGCATTAGCAGGTATTTAAATTGGTATCA GCAGAAACCAGGGAAAGCCCCTAAGCTCCTGATCTATGGTGCATCCAGATTAGAAAG TGGGGTCCCATCAAGGTTCAGTGGCAGTGGTTCTGGGACAGACTTCACTCTCACCATC AACAGCCTGCAACCTGAAGATTTTGCAACTTACTACTGTCAACAGAGTTACAGTACCC CTCTAACTTTTGGCCAGGGGACCCGAGTCGAAATTAAACGTGCTGTGGCTGCACCATC TGTCTTCATCTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTGGATAACG CCCTCCAATCGGGTAACTCCCAGGAGAGTGTCACAGAGCAGGACAGCAAGGACAGC ACCTACAGCCTCAGCAACACCCTGACGCTGAGCAAAGCAGACTACGAGAAACACAA AGTCTACGCCTGCGAAGTCACCCATCAGGGCCTGAGTTCGCCCGTCACAAAGAGCTT CAACAGGGGAGAGTGT |
| | Amino acid | ELVSTQSPSSLSASVGDRVTITCRASQSISRYLNWYQQKPGKAPKLLIYGASRLESGVPSRF SGSGSGTDFTLTINSLQPEDFATYYCQQSYSTPLTFGQGTRVEIKRSRTVAAPSVFIFPPSDE QLKSGTASVVCLLNNFYPREAKVQWKVDNALQSGNSQESVTEQDSKDSTYSLSNTLTLS KADYEKHKVYACEVTHQGLSSPVTKSFNRGEC |

*The linker and the effector domains were underlined and CDRs were written in bold.

FIG. 22J

10) 1β28$_{\Delta ds}$-hGH

| | | |
|---|---|---|
| Heavy chain (Hser_hGH format) | DNA | CAGGTGCAGCTGGTGCAGTCAGGGGGAGGCCTGGTCAGGCCGGGGGGGTCCCTGAG<br>ACTCTCCTGTGCAGCCTCTGGACTCATATTCAGTAATTATAGCATGAACTGGGTCCGC<br>CAGGCTCCGGGGAAGGGGCTGGAGTGGGTCTCATCAATAAGTAGTGCTGGTAGTTAC<br>AAATACTACACAGACTCAGTGAAGGGCCGATTCACCATCTCCAGAGACAACGCCAAG<br>AAGTCACTGTATCTGCAAATGAACAGCCTGAGAGTCGACGACACGGCCGTCTATTAC<br>TGTGCAAGAGGGGACTATGATACGGGCATGGAGCCCTGGGGCCAAGGCACCATGGTC<br>ACCGTCTCCTCATCGGCCACATTGGCCGCCTCCACCAAGGGCCCATCGGTCTTCCCCC<br>TGGCACCCTCCTCCAAGAGCACCTCTGGGGGCACAGCGGCCCTGGGCTGCCTGGTCA<br>AGGACTACTTCCCCGAACCGGTGACGGTGTCGTGGAACTCAGGCGCCCTGACCAGCG<br>GCGTGCACACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACGTGAATCA<br>CAAGCCCAGCAACACCAAGGTGGACAAGAGAGTTGAGCCCAAATCTAGTGGTTCTGC<br>ACCAGCTCCTGGATCTTTTCCGACCATTCCGCTGAGCCGCCTGTTCGATAACGCGATG<br>CTGCGCGCCCACCGCCTGCATCAACTGGCCTTTGATACCTATCAGGAGTTTGAGGAAG<br>CGTACATCCCGAAGGAACAGAAATATTCTTTTCTGCAGAACCCACAGACGAGCCTGT<br>GCTTTAGCGAATCTATCCCGACCCCGTCCAACCGCGAAGAAACCCAACAGAAGTCTA<br>ACCTGGAACTGCTGCGTATCTCTCTGCTGATTCAATCCTGGCTGGAACCGGTTCA<br>ATTTCTGCGTAGCGTGTTTGCGAACTCTCTGGTGTATGGCGCGTCTGACTCTAACGTG<br>TATGACCTGCTGAAAGATCTGGAAGAAGGCATCCAAACTCTGATGGGCCGTCTGGAG<br>GACGGCTCTCCACGTACCGGCCAGATCTTTAAACAGACCTATAGCAAATTTGACACC<br>AATTCTCACAACGATGATGCGCTGCTGAAAAACTATGGCCTGCTGTATTGCTTCCGTA<br>AAGACATGGATAAAGTTGAAACGTTCCTGCGCATTGTTCAGTGCCGTTCCGTGGAGG<br>GCTCCTGCGGCTTC |
| | Amino acid | QVQLVQSGGGLVRPGGSLRLSCAASGLIFSNYSMNWVRQAPGKGLEWVSSISSAGSYKY<br>YTDSVKGRFTISRDNAKKSLYLQMNSLRVDDIAVYYCARGDYDTGMEPWGQGTMVTV<br>SSSATLAASTKGPSVFPLAPSSKSTSEGTAALGCLVKDYFPEPVTVSWNSGALTSGVHTFP<br>AVLQSSGLYSLSSVVTVPSSSLGTQTYICNVNHKPSNTKVDKRVEPKSSGSAPAPGSFPTIP<br>LSRLFDNAMLRAHRLHQLAFDTYQEFEEAYIPKEQKYSFLQNPQTSLCFSESIPTPSNREET<br>QQKSNLELLRISLLIQSWLEPVQFLRSVFANSLVYGASDSNVYDLLKDLEFGIQTLMGRL<br>EDGSPRTGQIFKQTYSKFDTNSHNDDALLKNYGLLYCFRKDMDKVETFLRIVQCRSVEGS<br>CGF |
| Light chain (Lser format) | DNA | GAGCTCGAGCTCGTGTCGACGCAGTCTCCATCCTCCCTGTCTGCATCTGTGGGAGACA<br>GAGTCACCATTACTTGCCGGGCAAGTCAGAGCATTAGCAGGTATTTAAATTGGTATCA<br>GCAGAAACCAGGGAAAGCCCCTAAGCTCCTGATCTATGGTGCATCCAGATTAGAAAG<br>TGGGGTCCCATCAAGGTTCAGTGGCAGTGGTTCTGGGACAGACTTCACTCTCACCATC<br>AACAGCCTGCAACCTGAAGATTTTGCAACTTACTACTGTCAACAGAGTTACAGTACCC<br>CTCTAACTTTTGGCCAGGGGACCCGAGTCGAAATTAAACGTGCTGTGGCTGCACCATC<br>TGTCTTCATCTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAACACCCTGACGCTGAGCAAAGCAGACTACGAGAAACACAA<br>AGTCTACGCCTGCGAAGTCACCCATCAGGGCCTGAGTTCGCCCGTCACAAAGAGCTT<br>CAACAGGGGAGAGAGT |
| | Amino acid | ELVSTQSPSSLSASVGDRVTITCRASQSISRYLNWYQQKPGKAPKLLIYGASRLESGVPSRF<br>SGSGSGTDFTLTINSLQPEDFATYYCQQSYSTPLTFGQGTRVEIKRSRTVAAPSVFIFPPSDE<br>QLKSGTASVVCLLNNFYPREAKVQWKVDNALQSGNSQESVTEQDSKDSTYSLSNTLTLS<br>KADYEKHKVYACEVTHQGLSSPVTKSFNRGES |

*The linker and the effector domains were underlined and CDRs were written in bold.

SEQUENCE LISTING

```
<160> NUMBER OF SEQ ID NOS: 110

<210> SEQ ID NO 1
<211> LENGTH: 124
<212> TYPE: PRT
<213> ORGANISM: Homo sapiens

<400> SEQUENCE: 1

Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Val
        35                  40                  45

Gly Trp Ile Asn Thr Tyr Ser Gly Gly Thr Lys Tyr Ala Gln Lys Phe
    50                  55                  60

Gln Gly Arg Val Thr Met Thr Arg Asp Thr Ser Ile Ser Thr Val Tyr
65                  70                  75                  80

Met Glu Leu Ser Gly Leu Lys Ser Asp Asp Thr Ala Val Tyr Tyr Cys
                85                  90                  95

Ala Arg Leu Gly His Cys Gln Arg Gly Ile Cys Ser Asp Ala Leu Asp
            100                 105                 110

Thr Trp Gly Gln Gly Thr Leu Val Thr Val Ser Ser
        115                 120

<210> SEQ ID NO 2
<211> LENGTH: 124
<212> TYPE: PRT
<213> ORGANISM: Homo sapiens

<400> SEQUENCE: 2

Glu Val Gln Leu Leu Gln Ser Gly Ala Glu Val Lys Glu Pro Gly Ala
1               5                   10                  15

Ser Val Lys Val Ser Cys Lys Ala Ser Gly Tyr Thr Phe Ser Ser Tyr
            20                  25                  30

Gly Ile Ser Trp Val Arg Gln Ala Pro Gly Gln Gly Leu Glu Trp Val
        35                  40                  45

Gly Arg Ile Asn Thr Tyr Asn Gly Asn Thr Gly Tyr Ala Gln Arg Leu
    50                  55                  60

Gln Gly Arg Val Thr Met Thr Thr Asp Thr Ser Thr Ser Ile Ala Tyr
65                  70                  75                  80

Met Glu Val Arg Ser Leu Arg Ser Asp Asp Thr Ala Val Tyr Tyr Cys
```

```
                85                  90                  95
Ala Arg Leu Gly His Cys Gln Arg Gly Ile Cys Ser Asp Ala Leu Asp
            100                 105                 110

Thr Trp Gly Gln Gly Thr Met Val Thr Val Ser Ser
        115                 120
```

<210> SEQ ID NO 3
<211> LENGTH: 125
<212> TYPE: PRT
<213> ORGANISM: Homo sapiens

<400> SEQUENCE: 3

```
Gln Val Gln Leu Val Gln Ser Gly Gly Gly Val Val Gln Thr Gly Gly
1               5                   10                  15

Ser Leu Arg Leu Ser Cys Ala Ala Ser Gly Phe Thr Phe Arg Asn Tyr
            20                  25                  30

Gly Ile His Trp Val Arg Gln Ala Pro Gly Lys Gly Leu Glu Trp Val
            35                  40                  45

Ala Ser Ile Ser Tyr Asp Gly Ser Asn Lys Tyr Tyr Ala Asp Ser Val
        50                  55                  60

Lys Gly Arg Phe Thr Ile Ser Arg Asp Asn Ser Arg Asn Thr Val His
65                  70                  75                  80

Val Gln Met Asp Ser Leu Arg Gly Gly Asp Thr Ala Val Tyr Tyr Cys
                85                  90                  95

Ala Arg Asp Val His Tyr Tyr Gly Ser Gly Ser Tyr Tyr Asn Ala Phe
            100                 105                 110

Asp Ile Trp Gly Gln Gly Thr Leu Val Thr Val Ser Ser
            115                 120                 125
```

<210> SEQ ID NO 4
<211> LENGTH: 120
<212> TYPE: PRT
<213> ORGANISM: Homo sapiens

<400> SEQUENCE: 4

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
            35                  40                  45

Ser Val Ile Ser His Asp Gly Phe Gln Tyr Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Trp Leu Arg Gly Tyr Gly Met Asp Val Trp Gly Gln
            100                 105                 110

Gly Thr Leu Val Thr Val Ser Ser
        115                 120
```

<210> SEQ ID NO 5
<211> LENGTH: 117
<212> TYPE: PRT
<213> ORGANISM: Homo sapiens

<400> SEQUENCE: 5

```
Glu Val Gln Leu Val Gln Ser Gly Thr Glu Val Lys Pro Gly Glu
1               5                   10                  15

Ser Leu Lys Ile Ser Cys Lys Ile Ser Gly Tyr Ser Phe Thr Ala Tyr
            20                  25                  30

Trp Ile Ala Trp Val Arg Gln Met Pro Gly Lys Gly Leu Glu Trp Met
        35                  40                  45

Gly Met Ile Trp Pro Pro Asp Ala Asp Ala Arg Tyr Ser Pro Ser Phe
    50                  55                  60

Gln Gly Gln Val Thr Phe Ser Val Asp Lys Ser Ile Ser Thr Ala Tyr
65                  70                  75                  80

Leu Gln Trp His Ser Leu Lys Thr Ser Asp Thr Ala Val Tyr Tyr Cys
                85                  90                  95

Ala Arg Leu Tyr Ser Gly Ser Tyr Ser Pro Trp Gly Gln Gly Thr Leu
            100                 105                 110

Val Thr Val Ser Ser
            115
```

```
<210> SEQ ID NO 6
<211> LENGTH: 120
<212> TYPE: PRT
<213> ORGANISM: Homo sapiens

<400> SEQUENCE: 6

Gln Val Gln Leu Val Gln Ser Gly Gly Gly Pro Val Lys Pro Gly Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
            35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
            100                 105                 110

Gly Thr Leu Val Thr Val Ser Ser
            115                 120
```

```
<210> SEQ ID NO 7
<211> LENGTH: 108
<212> TYPE: PRT
<213> ORGANISM: Homo sapiens

<400> SEQUENCE: 7

Glu Leu Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
            35                  40                  45

Tyr Gly Ala Ser Arg Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Asp Ser Val Pro Val
                85                  90                  95

Thr Phe Gly Gln Gly Thr Arg Leu Glu Ile Lys Arg
            100                 105

<210> SEQ ID NO 8
<211> LENGTH: 109
<212> TYPE: PRT
<213> ORGANISM: Homo sapiens

<400> SEQUENCE: 8

Asp Ile Val Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Tyr Thr Phe Gly Gln Gly Thr Lys Leu Glu Ile Lys Arg
            100                 105

<210> SEQ ID NO 9
<211> LENGTH: 110
<212> TYPE: PRT
<213> ORGANISM: Homo sapiens

<400> SEQUENCE: 9

Glu Leu Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Phe Asn Tyr
                20                  25                  30

Val Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Thr Trp Thr Phe Gly Gln Gly Thr Arg Val Asp Ile Lys Arg
            100                 105                 110

<210> SEQ ID NO 10
<211> LENGTH: 109
<212> TYPE: PRT
<213> ORGANISM: Homo sapiens

<400> SEQUENCE: 10

Glu Leu Val Leu Thr Gln Ser Pro Gly Thr Leu Ser Leu Ser Pro Gly
1               5                   10                  15

Glu Arg Ala Thr Leu Ser Cys Arg Ala Ser Glu Thr Val Ser Ser Arg
                20                  25                  30
```

Gln Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Ser Ala Val Phe Tyr Cys Gln Gln Tyr Gly Ser Ser Pro
                85                  90                  95

Arg Thr Phe Gly Gly Gly Thr Lys Leu Glu Ile Lys Arg
            100                 105

<210> SEQ ID NO 11
<211> LENGTH: 109
<212> TYPE: PRT
<213> ORGANISM: Homo sapiens

<400> SEQUENCE: 11

Glu Leu Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Ser Leu Gln
65                  70                  75                  80

Pro Glu Asp Ala Ala Thr Tyr Tyr Cys Gln Lys Tyr Ser Ser Tyr Pro
                85                  90                  95

Leu Thr Phe Gly Gln Gly Thr Lys Leu Glu Ile Lys Arg
            100                 105

<210> SEQ ID NO 12
<211> LENGTH: 109
<212> TYPE: PRT
<213> ORGANISM: Homo sapiens

<400> SEQUENCE: 12

Glu Leu Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Gly Ala Thr Gly Val Pro Ala Arg Phe Ser Gly
 50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg
            100                 105

<210> SEQ ID NO 13
<211> LENGTH: 5
<212> TYPE: PRT
<213> ORGANISM: Homo sapiens

<400> SEQUENCE: 13

Ala Tyr Ser Met Asn
1               5

<210> SEQ ID NO 14
<211> LENGTH: 17
<212> TYPE: PRT
<213> ORGANISM: Homo sapiens

<400> SEQUENCE: 14

Ser Ile Ser Ser Ser Gly Arg Tyr Ile His Tyr Ala Asp Ser Val Lys
1               5                   10                  15

Gly

<210> SEQ ID NO 15
<211> LENGTH: 11
<212> TYPE: PRT
<213> ORGANISM: Homo sapiens

<400> SEQUENCE: 15

Glu Thr Val Met Ala Gly Lys Ala Leu Asp Tyr
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Ser Val Gly Ser Asn Leu Ala
1               5                   10

<210> SEQ ID NO 17
<211> LENGTH: 7
<212> TYPE: PRT
<213> ORGANISM: Homo sapiens

<400> SEQUENCE: 17

Gly Ala Ser Thr Gly Ala Thr
1               5

<210> SEQ ID NO 18
<211> LENGTH: 10
<212> TYPE: PRT
<213> ORGANISM: Homo sapiens

<400> SEQUENCE: 18

Gln Gln Tyr Tyr Ser Phe Leu Ala Lys Thr
1               5                   10

<210> SEQ ID NO 19
<211> LENGTH: 23
<212> TYPE: DNA
<213> ORGANISM: Homo sapiens

<400> SEQUENCE: 19
gtgccgttct atagccatag cac                                            23

<210> SEQ ID NO 20
<211> LENGTH: 25
<212> TYPE: DNA
<213> ORGANISM: Homo sapiens

<400> SEQUENCE: 20

```
ggcactggct ggtttcgcta ccgtg                                              25

<210> SEQ ID NO 21
<211> LENGTH: 39
<212> TYPE: DNA
<213> ORGANISM: Homo sapiens

<400> SEQUENCE: 21
gggagatctt gaaatgagct gttgacaatt aatcatccg                               39

<210> SEQ ID NO 22
<211> LENGTH: 39
<212> TYPE: DNA
<213> ORGANISM: Homo sapiens

<400> SEQUENCE: 22
cctctttaat ttttaataat aaagttaatc gataattcc                               39

<210> SEQ ID NO 23
<211> LENGTH: 70
<212> TYPE: DNA
<213> ORGANISM: Homo sapiens

<400> SEQUENCE: 23
ggaattatcg attaacttta ttattaaaaa ttaagaggt atatattagg atccgagctc         60
gagttctgca                                                               70

<210> SEQ ID NO 24
<211> LENGTH: 34
<212> TYPE: DNA
<213> ORGANISM: Homo sapiens

<400> SEQUENCE: 24
gggcactacg tgcgaaaggc ccagtctttc gact                                    34

<210> SEQ ID NO 25
<211> LENGTH: 69
<212> TYPE: DNA
<213> ORGANISM: Homo sapiens

<400> SEQUENCE: 25
ggccgcagat ctgttaatta aggaggaatt taaagaattc atgaaaaaac tgctgttcgc        60
gattccgct                                                                69

<210> SEQ ID NO 26
<211> LENGTH: 41
<212> TYPE: DNA
<213> ORGANISM: Homo sapiens

<400> SEQUENCE: 26
gggaagctta ttaacaagat ttgggctcaa ctctcttgtc c                            41

<210> SEQ ID NO 27
<211> LENGTH: 39
<212> TYPE: DNA
<213> ORGANISM: Homo sapiens

<400> SEQUENCE: 27
gggggatcca tgaaaaagac agctatcgcg attgcagtg                               39

<210> SEQ ID NO 28
```

```
<211> LENGTH: 69
<212> TYPE: DNA
<213> ORGANISM: Homo sapiens

<400> SEQUENCE: 28
attcctcctt aattaacaga tctgcggccg cactcgagat taacactctc ccctgttgaa    60
gctctttgt                                                            69

<210> SEQ ID NO 29
<211> LENGTH: 63
<212> TYPE: DNA
<213> ORGANISM: Homo sapiens

<400> SEQUENCE: 29
ggggaattca tgaaatatct gctgcctacg gcggcggcgg gcctgctgct gctggctgca    60
caa                                                                  63

<210> SEQ ID NO 30
<211> LENGTH: 35
<212> TYPE: DNA
<213> ORGANISM: Homo sapiens

<400> SEQUENCE: 30
gggaagcttt tagctgctct tcggttccac gcgtt                               35

<210> SEQ ID NO 31
<211> LENGTH: 52
<212> TYPE: DNA
<213> ORGANISM: Homo sapiens

<400> SEQUENCE: 31
gggggatcca tgaaaaaaac tgcgattgcg attgcggtgc tggccggctt tg            52

<210> SEQ ID NO 32
<211> LENGTH: 38
<212> TYPE: DNA
<213> ORGANISM: Homo sapiens

<400> SEQUENCE: 32
gggctcgagt tagctttcgc cgcggttaaa gctctttg                            38

<210> SEQ ID NO 33
<211> LENGTH: 47
<212> TYPE: DNA
<213> ORGANISM: Homo sapiens

<400> SEQUENCE: 33
agatccagga gctggtgcag aaccgcagct cttcggttcc acgcgtt                  47

<210> SEQ ID NO 34
<211> LENGTH: 47
<212> TYPE: DNA
<213> ORGANISM: Homo sapiens

<400> SEQUENCE: 34
ggttctgcac cagctcctgg atcttttccg accattccgc tgagccg                  47

<210> SEQ ID NO 35
<211> LENGTH: 32
<212> TYPE: DNA
<213> ORGANISM: Homo sapiens

<400> SEQUENCE: 35
```

-continued

```
gggaagcttt tagaagccgc aggagccctc ca                                    32

<210> SEQ ID NO 36
<211> LENGTH: 49
<212> TYPE: DNA
<213> ORGANISM: Homo sapiens

<400> SEQUENCE: 36
agatccagga gctggtgcag aaccgcattc gccgcggtta aagctcttt                  49

<210> SEQ ID NO 37
<211> LENGTH: 32
<212> TYPE: DNA
<213> ORGANISM: Homo sapiens

<400> SEQUENCE: 37
gggctcgagt tagaagccgc aggagccctc ca                                    32

<210> SEQ ID NO 38
<211> LENGTH: 32
<212> TYPE: DNA
<213> ORGANISM: Homo sapiens

<400> SEQUENCE: 38
gggctcgagt tagaagccgc aggagccctc ca                                    32

<210> SEQ ID NO 39
<211> LENGTH: 47
<212> TYPE: DNA
<213> ORGANISM: Homo sapiens

<400> SEQUENCE: 39
agatccagga gctggtgcag aaccgctgct cttcggttcc acgcgtt                    47

<210> SEQ ID NO 40
<211> LENGTH: 50
<212> TYPE: DNA
<213> ORGANISM: Homo sapiens

<400> SEQUENCE: 40
agatccagga gctggtgcag aaccgctttc gccgcggtta aagctctttg                 50

<210> SEQ ID NO 41
<211> LENGTH: 46
<212> TYPE: DNA
<213> ORGANISM: Homo sapiens

<400> SEQUENCE: 41
ggttctgcac cagctcctgg atctgcgcct acctatcgcg cgagca                     46

<210> SEQ ID NO 42
<211> LENGTH: 34
<212> TYPE: DNA
<213> ORGANISM: Homo sapiens

<400> SEQUENCE: 42
gggaagctta ttaaggctgt gccagatggc gcag                                  34

<210> SEQ ID NO 43
<211> LENGTH: 49
<212> TYPE: DNA
<213> ORGANISM: Homo sapiens
```

```
<400> SEQUENCE: 43
agatccagga gctggtgcag aaccgcattc gccgcggtta aagctcttt            49

<210> SEQ ID NO 44
<211> LENGTH: 50
<212> TYPE: DNA
<213> ORGANISM: Homo sapiens

<400> SEQUENCE: 44
taacagatct gcggccgcac tcgagattaa ggctgtgcca gatggcgcag           50

<210> SEQ ID NO 45
<211> LENGTH: 47
<212> TYPE: DNA
<213> ORGANISM: Homo sapiens

<400> SEQUENCE: 45
agatccagga gctggtgcag aaccgctgct cttcggttcc acgcgtt              47

<210> SEQ ID NO 46
<211> LENGTH: 50
<212> TYPE: DNA
<213> ORGANISM: Homo sapiens

<400> SEQUENCE: 46
agatccagga gctggtgcag aaccgctttc gccgcggtta aagctctttg           50

<210> SEQ ID NO 47
<211> LENGTH: 47
<212> TYPE: DNA
<213> ORGANISM: Homo sapiens

<400> SEQUENCE: 47
agatccagga gctggtgcag aaccgcagct cttcggttcc acgcgtt              47

<210> SEQ ID NO 48
<211> LENGTH: 48
<212> TYPE: DNA
<213> ORGANISM: Homo sapiens

<400> SEQUENCE: 48
ggttctgcac cagctcctgg atcttcatac aacctgctgg gcttcctg             48

<210> SEQ ID NO 49
<211> LENGTH: 33
<212> TYPE: DNA
<213> ORGANISM: Homo sapiens

<400> SEQUENCE: 49
gggaagcttt tagttgcgca gatagccggt cag                             33

<210> SEQ ID NO 50
<211> LENGTH: 47
<212> TYPE: DNA
<213> ORGANISM: Homo sapiens

<400> SEQUENCE: 50
agatccagga gctggtgcag aaccgctgct cttcggttcc acgcgtt              47

<210> SEQ ID NO 51
<211> LENGTH: 38
<212> TYPE: DNA
<213> ORGANISM: Homo sapiens
```

<400> SEQUENCE: 51
gggaagctta ttaactagat ttgggctcaa ctctcttg        38

<210> SEQ ID NO 52
<211> LENGTH: 37
<212> TYPE: DNA
<213> ORGANISM: Homo sapiens

<400> SEQUENCE: 52
gggctcgagt tagcattcgc cgcggttaaa gctcttt        37

<210> SEQ ID NO 53
<211> LENGTH: 37
<212> TYPE: DNA
<213> ORGANISM: Homo sapiens

<400> SEQUENCE: 53
gggctcgagt tagctttcgc cgcggttaaa gctcttt        37

<210> SEQ ID NO 54
<211> LENGTH: 51
<212> TYPE: DNA
<213> ORGANISM: Homo sapiens

<400> SEQUENCE: 54
agatccagga gctggtgcag aaccacaaga tttgggctca actctcttgt c        51

<210> SEQ ID NO 55
<211> LENGTH: 51
<212> TYPE: DNA
<213> ORGANISM: Homo sapiens

<400> SEQUENCE: 55
agatccagga gctggtgcag aaccactaga tttgggctca actctcttgt c        51

<210> SEQ ID NO 56
<211> LENGTH: 20
<212> TYPE: PRT
<213> ORGANISM: Homo sapiens

<400> SEQUENCE: 56

Met Lys Lys Thr Ala Ile Ala Ile Ala Val Leu Ala Gly Phe Ala Thr
1               5                   10                  15

Val Ala Gln Ala
            20

<210> SEQ ID NO 57
<211> LENGTH: 22
<212> TYPE: PRT
<213> ORGANISM: Homo sapiens

<400> SEQUENCE: 57

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 58
<211> LENGTH: 1287
<212> TYPE: DNA
<213> ORGANISM: Homo sapiens

<400> SEQUENCE: 58

```
caagttcagc tggttcagag cggtggcggc ccggtgaaac caggtggcag cctgcgtctg      60
tcctgcgcgg cgagcggttt tatgtttcgt gcgtatagca tgaactgggt gcgccaggcg     120
ccgggcaaag gcctggaatg ggtgagcagc attagcagca gtggccgcta tattcattat     180
gccgacagtg ttaaaggtcg ttttaccatt tctcgtgaca atgcgaaaaa cagcctgtat     240
ctgcaaatga atagcctgcg cgcggaagac accgcggtgt actactgtgc gcgcgaaacc     300
gtgatggcgg gcaaagcact ggattattgg ggtcagggca ccctggtgac cgtgagcagc     360
gcgagcacca aaggcccgag cgcgagcacc aaaggcccga gcgtgtttcc gctggcacct     420
agttcgaaat caacgagcgg tggcaccgcg gctctgggct gcctggtgaa agattatttc     480
ccggaacctg ttaccgtgag ctggaacagc ggtgcgttga cgagtggtgt gcatacccttt     540
cccgcagttc tgcaatcgag cggcctgtac tcactgagca gcgtggttac ggtcccgagc     600
agtagcctgg gtacacagac ctatatttgt aacgtgaacc acaagccttc gaacacgaaa     660
gttgacaaac gcgtggaacc gaagagctgc ggttctgcac cagctcctgg atcttttccg     720
accattccgc tgagccgcct gttcgataac gcgatgctgc gcgcccaccg cctgcatcaa     780
ctggcctttg atacctatca ggagtttgag gaagcgtaca tcccgaagga acagaaatat     840
tcttttctgc agaacccaca gacgagcctg tgctttagcg aatctatccc gaccccgtcc     900
aaccgcgaag aaacccaaca gaagtctaac ctggaactgc tgcgtatctc tctgctgctg     960
attcaatcct ggctggaacc ggttcaattt ctgcgtagcg tgtttgcgaa ctctctggtg    1020
tatggcgcgt ctgactctaa cgtgtatgac ctgctgaaag atctggaaga aggcatccaa    1080
actctgatgg gccgtctgga ggacggctct ccacgtaccg ccagatctt taaacagacc    1140
tatagcaaat ttgacaccaa ttctcacaac gatgatgcgc tgctgaaaaa ctatggcctg    1200
ctgtattgct ccgtaaaga catggataaa gttgaaacgt tcctgcgcat tgttcagtgc    1260
cgttccgtgg agggctcctg cggcttc                                       1287
```

<210> SEQ ID NO 59
<211> LENGTH: 429
<212> TYPE: PRT
<213> ORGANISM: Homo sapiens

<400> SEQUENCE: 59

```
Gln Val Gln Leu Val Gln Ser Gly Gly Gly Pro Val Lys Pro Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
            100                 105                 110

Gly Thr Leu Val Thr Val Ser Ser Ala Ser Thr Lys Gly Pro Ser Ala
        115                 120                 125

Ser Thr Lys Gly Pro Ser Val Phe Pro Leu Ala Pro Ser Ser Lys Ser
```

```
            130                 135                 140
Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Gly Ser Ala Pro Ala Pro Gly Ser Phe Pro
225                 230                 235                 240

Thr Ile Pro Leu Ser Arg Leu Phe Asp Asn Ala Met Leu Arg Ala His
                245                 250                 255

Arg Leu His Gln Leu Ala Phe Asp Thr Tyr Gln Glu Phe Glu Glu Ala
            260                 265                 270

Tyr Ile Pro Lys Glu Gln Lys Tyr Ser Phe Leu Gln Asn Pro Gln Thr
        275                 280                 285

Ser Leu Cys Phe Ser Glu Ser Ile Pro Thr Pro Ser Asn Arg Glu Glu
    290                 295                 300

Thr Gln Gln Lys Ser Asn Leu Glu Leu Leu Arg Ile Ser Leu Leu Leu
305                 310                 315                 320

Ile Gln Ser Trp Leu Glu Pro Val Gln Phe Leu Arg Ser Val Phe Ala
                325                 330                 335

Asn Ser Leu Val Tyr Gly Ala Ser Asp Ser Asn Val Tyr Asp Leu Leu
            340                 345                 350

Lys Asp Leu Glu Glu Gly Ile Gln Thr Leu Met Gly Arg Leu Glu Asp
        355                 360                 365

Gly Ser Pro Arg Thr Gly Gln Ile Phe Lys Gln Thr Tyr Ser Lys Phe
    370                 375                 380

Asp Thr Asn Ser His Asn Asp Asp Ala Leu Leu Lys Asn Tyr Gly Leu
385                 390                 395                 400

Leu Tyr Cys Phe Arg Lys Asp Met Asp Lys Val Glu Thr Phe Leu Arg
                405                 410                 415

Ile Val Gln Cys Arg Ser Val Glu Gly Ser Cys Gly Phe
            420                 425

<210> SEQ ID NO 60
<211> LENGTH: 666
<212> TYPE: DNA
<213> ORGANISM: Homo sapiens

<400> SEQUENCE: 60
gatatcgttc tgacccaatc tccgggtacg ctgagcctga gcccgggcga aaccgcgacc      60
ctgagctgcc gcgcgagcca aagcgtgggt tctaatctgg cttggtatca gcagaaaccg     120
ggtcaggccc cgcgcctgct gatctatggg gcgagcacgg gggctaccgg cgttccggcg     180
cgctttagtg gcagtcgcag cggcaccgat tttaccctga ccattacaag tctgcagccg     240
gaagattttg cgacctatta ttgccagcaa tattatagct tcctggcgaa aacctttggt     300
cagggcaccc agctggaaat taaacgcacc gtggcggcac ccagcgtgac ggtggcggca     360
cccagcgtgt ttatttttcc tcccagtgat gaacagctga aaagcgggac cgcgagtgtt     420
gtgtgcctgt tgaacaactt ctatcctcgc gaagcgaaag tgcagtggaa agtggataac     480
```

```
gcattgcaga gcggcaacag tcaggaaagc gttactgaac aggatagcaa agatagtacg    540
tacagcttga gcaacactct gaccctgagt aaagcggatt atgaaaaaca taaagtgtat    600
gcatgcgaag ttacgcatca ggggctgagc agtccggtga caaagagctt taaccgcggc    660
gaatgc                                                               666
```

```
<210> SEQ ID NO 61
<211> LENGTH: 222
<212> TYPE: PRT
<213> ORGANISM: Homo sapiens

<400> SEQUENCE: 61
```

Asp Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg Thr Val Ala
            100                 105                 110

Ala Pro Ser Val Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Asn Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

```
<210> SEQ ID NO 62
<211> LENGTH: 1287
<212> TYPE: DNA
<213> ORGANISM: Homo sapiens

<400> SEQUENCE: 62
```

```
caagttcagc tggttcagag cggtggcggc ccggtgaaac aggtggcag cctgcgtctg     60 tcctgcgcgg cgagcggttt tatgtttcgt gcgtatagca tgaactgggt gcgccaggcg    120
ccgggcaaag gcctggaatg ggtgagcagc attagcagca gtggccgcta tattcattat    180
gccgacagtg ttaaaggtcg ttttaccatt tctcgtgaca atgcgaaaaa cagcctgtat    240
ctgcaaatga atagcctgcg cgcggaagac accgcggtgt actactgtgc gcgcgaaacc    300
gtgatggcgg gcaaagcact ggattattgg ggtcagggca ccctggtgac cgtgagcagc    360
```

```
gcgagcacca aaggcccgag cgcgagcacc aaaggcccga gcgtgtttcc gctggcacct    420
agttcgaaat caacgagcgg tggcaccgcg gctctgggct gcctggtgaa agattatttc    480
ccggaacctg ttaccgtgag ctggaacagc ggtgcgttga cgagtggtgt gcataccttt    540
cccgcagttc tgcaatcgag cggcctgtac tcactgagca gcgtggttac ggtcccgagc    600
agtagcctgg gtacacagac ctatatttgt aacgtgaacc acaagccttc gaacacgaaa    660
gttgacaaac gcgtggaacc gaagagcagc ggttctgcac cagctcctgg atctttccg     720 accattccgc tgagccgcct gttcgataac gcgatgctgc gcgcccaccg cctgcatcaa    780
ctggcctttg atacctatca ggagtttgag gaagcgtaca tcccgaagga acagaaatat    840
tcttttctgc agaacccaca gacgagcctg tgctttagcg aatctatccc gaccccgtcc    900
aaccgcgaag aaacccaaca gaagtctaac ctggaactgc tgcgtatctc tctgctgctg    960
attcaatcct ggctggaacc ggttcaattt ctgcgtagcg tgtttgcgaa ctctctggtg   1020
tatggcgcgt ctgactctaa cgtgtatgac ctgctgaaag atctggaaga aggcatccaa   1080
actctgatgg gccgtctgga ggacggctct ccacgtaccg ccagatcttt aaacagacc    1140 tatagcaaat ttgacaccaa ttctcacaac gatgatgcgc tgctgaaaaa ctatggcctg   1200
ctgtattgct tccgtaaaga catggataaa gttgaaacgt cctgcgcat tgttcagtgc   1260 cgttccgtgg agggctcctg cggcttc                                       1287
```

<210> SEQ ID NO 63
<211> LENGTH: 429
<212> TYPE: PRT
<213> ORGANISM: Homo sapiens

<400> SEQUENCE: 63

```
Gln Val Gln Leu Val Gln Ser Gly Gly Gly Pro Val Lys Pro Gly Gly
1               5                   10                  15

Ser Leu Arg Leu Ser Cys Ala Ala Ser Gly Phe Met Phe Arg Ala Tyr
                20                  25                  30

Ser Met Asn Trp Val Arg Gln Ala Pro Gly Lys Gly Leu Glu Trp Val
            35                  40                  45

Ser Ser Ile Ser Ser Ser Gly Arg Tyr Ile His Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
                100                 105                 110

Gly Thr Leu Val Thr Val Ser Ser Ala Ser Thr Lys Gly Pro Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205
```

Ile Cys Asn Val Asn His Lys Pro Ser Asn Thr Lys Val Asp Lys Arg
210                 215                 220

Val Glu Pro Lys Ser Ser Gly Ser Ala Pro Ala Pro Gly Ser Phe Pro
225                 230                 235                 240

Thr Ile Pro Leu Ser Arg Leu Phe Asp Asn Ala Met Leu Arg Ala His
            245                 250                 255

Arg Leu His Gln Leu Ala Phe Asp Thr Tyr Gln Glu Phe Glu Glu Ala
        260                 265                 270

Tyr Ile Pro Lys Glu Gln Lys Tyr Ser Phe Leu Gln Asn Pro Gln Thr
    275                 280                 285

Ser Leu Cys Phe Ser Glu Ser Ile Pro Thr Pro Ser Asn Arg Glu Glu
290                 295                 300

Thr Gln Gln Lys Ser Asn Leu Glu Leu Leu Arg Ile Ser Leu Leu Leu
305                 310                 315                 320

Ile Gln Ser Trp Leu Glu Pro Val Gln Phe Leu Arg Ser Val Phe Ala
            325                 330                 335

Asn Ser Leu Val Tyr Gly Ala Ser Asp Ser Asn Val Tyr Asp Leu Leu
        340                 345                 350

Lys Asp Leu Glu Glu Gly Ile Gln Thr Leu Met Gly Arg Leu Glu Asp
    355                 360                 365

Gly Ser Pro Arg Thr Gly Gln Ile Phe Lys Gln Thr Tyr Ser Lys Phe
370                 375                 380

Asp Thr Asn Ser His Asn Asp Asp Ala Leu Leu Lys Asn Tyr Gly Leu
385                 390                 395                 400

Leu Tyr Cys Phe Arg Lys Asp Met Asp Lys Val Glu Thr Phe Leu Arg
            405                 410                 415

Ile Val Gln Cys Arg Ser Val Glu Gly Ser Cys Gly Phe
        420                 425

<210> SEQ ID NO 64
<211> LENGTH: 666
<212> TYPE: DNA
<213> ORGANISM: Homo sapiens

<400> SEQUENCE: 64
gatatcgttc tgacccaatc tccgggtacg ctgagcctga gcccgggcga aaccgcgacc      60
ctgagctgcc gcgcgagcca aagcgtgggt tctaatctgg cttggtatca gcagaaaccg     120
ggtcaggccc cgcgcctgct gatctatggg gcgagcacgg gggctaccgg cgttccggcg     180
cgctttagtg gcagtcgcag cggcaccgat tttacccctg accattacaa gtctgcagcc     240
gaagattttg cgacctatta ttgccagcaa tattatagct tcctggcgaa aaccttcggt     300
cagggcaccc agctggaaat taaacgcacc gtggcggcac ccagcgtgac ggtggcggca     360
cccagcgtgt ttattttcc tcccagtgat gaacagctga aaagcgggac cgcgagtgtt     420
gtgtgcctgt tgaacaactt ctatcctcgc gaagcgaaag tgcagtggaa agtggataac     480
gcattgcaga gcggcaacag tcaggaaagc gttactgaac aggatagcaa agatagtacg     540
tacagcttga gcaacactct gaccctgagt aaagcggatt atgaaaaaca taaagtgtat     600
gcatgcgaag ttcgcatca ggggctgagc agtccggtga caaagagctt aaccgcggc     660 gaaagc                                                                666

<210> SEQ ID NO 65
<211> LENGTH: 222
<212> TYPE: PRT
<213> ORGANISM: Homo sapiens

<400> SEQUENCE: 65

Asp Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg Thr Val Ala
            100                 105                 110

Ala Pro Ser Val Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Asn Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Ser
    210                 215                 220

<210> SEQ ID NO 66
<211> LENGTH: 1236
<212> TYPE: DNA
<213> ORGANISM: Homo sapiens

<400> SEQUENCE: 66
caagttcagc tggttcagag cggtggcggc ccggtgaaac aggtggcag cctgcgtctg     60 tcctgcgcgg cgagcggttt tatgtttcgt gcgtatagca tgaactgggt gcgccaggcg    120
ccgggcaaag gcctggaatg ggtgagcagc attagcagca gtggccgcta tattcattat    180
gccgacagtg ttaaaggtcg ttttaccatt tctcgtgaca atgcgaaaaa cagcctgtat    240
ctgcaaatga atagcctgcg cgcggaagac accgcgtgt actactgtgc gcgcgaaacc    300
gtgatggcgg gcaaagcact ggattattgg ggtcaggca ccctggtgac cgtgagcagc    360
gcgagcacca aaggcccgag cgcgagcacc aaaggcccga gcgtgtttcc gctggcacct    420
agttcgaaat caacgagcgg tggcaccgcg gctctgggct gcctggtgaa agattatttc    480
ccggaacctg ttaccgtgag ctggaacagc ggtgcgttga cgagtggtgt gcatacctt    540 cccgcagttc tgcaatcgag cggcctgtac tcactgagca gcgtggttac ggtcccgagc    600
agtagcctgg gtacacagac ctatatttgt aacgtgaacc acaagccttc gaacacgaaa    660
gttgacaaac gcgtggaacc gaagagctgc ggttctgcac cagctcctgg atctgcgcct    720
acctatcgcg cgagcagcct gccgcagtcg tttctgctga aaagcctgga acaggtgcgc    780

```
aagattcagg gtgacggcgc agctctgcaa gaaaaactgt gcgcgaccta caaattgtgc    840
caccctgagg aactggttct gctgggccat agtctgggca ttccgtgggc gccgctgagc    900
agctgcccgt cgcaggcatt gcagctggct ggctgtctga gccagttaca tagcggtctg    960
tttctgtatc agggcctgct gcaagcgctg gaaggcatca gtcctgagtt gggtccgacc   1020
ctggatacct tacagctgga tgtggcggat ttcgcaacca ccatttggca gcagatggaa   1080
gaattgggca tggctccggc gttgcagccg acccagggcg cgatgcctgc gtttgcaagc   1140
gcttttcagc gccgcgcggg tggggtgctg gtggcgtcgc acttgcagag cttcctggaa   1200
gtgagctacc gtgtcctgcg ccatctggca cagcct                             1236
```

<210> SEQ ID NO 67
<211> LENGTH: 412
<212> TYPE: PRT
<213> ORGANISM: Homo sapiens

<400> SEQUENCE: 67

```
Gln Val Gln Leu Val Gln Ser Gly Gly Gly Pro Val Lys Pro Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
            100                 105                 110

Gly Thr Leu Val Thr Val Ser Ser Ala Ser Thr Lys Gly Pro Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Gly Ser Ala Pro Ala Pro Gly Ser Ala Pro
225                 230                 235                 240

Thr Tyr Arg Ala Ser Ser Leu Pro Gln Ser Phe Leu Leu Lys Ser Leu
                245                 250                 255

Glu Gln Val Arg Lys Ile Gln Gly Asp Gly Ala Ala Leu Gln Glu Lys
            260                 265                 270

Leu Cys Ala Thr Tyr Lys Leu Cys His Pro Glu Glu Leu Val Leu Leu
        275                 280                 285

Gly His Ser Leu Gly Ile Pro Trp Ala Pro Leu Ser Ser Cys Pro Ser
```

```
                    290                 295                 300
Gln Ala Leu Gln Leu Ala Gly Cys Leu Ser Gln Leu His Ser Gly Leu
305                 310                 315                 320

Phe Leu Tyr Gln Gly Leu Leu Gln Ala Leu Glu Gly Ile Ser Pro Glu
                325                 330                 335

Leu Gly Pro Thr Leu Asp Thr Leu Gln Leu Asp Val Ala Asp Phe Ala
                340                 345                 350

Thr Thr Ile Trp Gln Gln Met Glu Glu Leu Gly Met Ala Pro Ala Leu
            355                 360                 365

Gln Pro Thr Gln Gly Ala Met Pro Ala Phe Ala Ser Ala Phe Gln Arg
        370                 375                 380

Arg Ala Gly Gly Val Leu Val Ala Ser His Leu Gln Ser Phe Leu Glu
385                 390                 395                 400

Val Ser Tyr Arg Val Leu Arg His Leu Ala Gln Pro
                405                 410
```

<210> SEQ ID NO 68
<211> LENGTH: 666
<212> TYPE: DNA
<213> ORGANISM: Homo sapiens
<400> SEQUENCE: 68

```
gatatcgttc tgacccaatc tccgggtacg ctgagcctga gcccgggcga accgcgacc    60
ctgagctgcc gcgcgagcca aagcgtgggt tctaatctgg cttggtatca gcagaaaccg   120
ggtcaggccc cgcgcctgct gatctatggg gcgagcacgg gggctaccgg cgttccggcg   180
cgctttagtg gcagtcgcag cggcaccgat tttaccctga ccattacaag tctgcagccg   240
gaagattttg cgacctatta ttgccagcaa tattatagct tcctggcgaa aacctttggt   300
cagggcaccc agctggaaat taaacgcacc gtggcggcac ccagcgtgac ggtggcggca   360
cccagcgtgt ttatttttcc tcccagtgat gaacagctga aaagcgggac cgcgagtgtt   420
gtgtgcctgt tgaacaactt ctatcctcgc gaagcgaaag tgcagtggaa agtggataac   480
gcattgcaga gcggcaacag tcaggaaagc gttactgaac aggatagcaa agatagtacg   540
tacagcttga gcaacactct gaccctgagt aaagcggatt atgaaaaaca taaagtgtat   600
gcatgcgaag ttacgcatca ggggctgagc agtccggtga caaagagctt aaccgcggc   660
gaatgc                                                              666
```

<210> SEQ ID NO 69
<211> LENGTH: 222
<212> TYPE: PRT
<213> ORGANISM: Homo sapiens
<400> SEQUENCE: 69

```
Asp Ile Val Leu Thr Gln Ser Pro Gly Thr Leu Ser Leu Ser Pro Gly
1               5                  10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
```

|   |   |   | 85 |   |   |   | 90 |   |   |   | 95 |   |   |
|---|---|---|---|---|---|---|---|---|---|---|---|---|---|
Lys Thr Phe Gly Gln Gly Thr Gln Leu Glu Ile Lys Arg Thr Val Ala
                    100                  105              110

Ala Pro Ser Val Thr Val Ala Ala Pro Ser Val Phe Ile Phe Pro Pro
          115                  120                125

Ser Asp Glu Gln Leu Lys Ser Gly Thr Ala Ser Val Val Cys Leu Leu
    130                  135                140

Asn Asn Phe Tyr Pro Arg Glu Ala Lys Val Gln Trp Lys Val Asp Asn
145                  150                  155              160

Ala Leu Gln Ser Gly Asn Ser Gln Glu Ser Val Thr Glu Gln Asp Ser
          165                  170                175

Lys Asp Ser Thr Tyr Ser Leu Ser Asn Thr Leu Thr Leu Ser Lys Ala
              180                  185              190

Asp Tyr Glu Lys His Lys Val Tyr Ala Cys Glu Val Thr His Gln Gly
                195                200              205

Leu Ser Ser Pro Val Thr Lys Ser Phe Asn Arg Gly Glu Cys
    210                  215                220

<210> SEQ ID NO 70
<211> LENGTH: 1236
<212> TYPE: DNA
<213> ORGANISM: Homo sapiens

<400> SEQUENCE: 70

```
caagttcagc tggttcagag cggtggcggc ccggtgaaac caggtggcag cctgcgtctg      60
tcctgcgcgg cgagcggttt tatgtttcgt gcgtatagca tgaactgggt gcgccaggcg     120
ccgggcaaag gcctggaatg ggtgagcagc attagcagca gtggccgcta tattcattat     180
gccgacagtg ttaaaggtcg ttttaccatt tctcgtgaca tgcgaaaaa cagcctgtat     240
ctgcaaatga atagcctgcg cgcggaagac accgcggtgt actactgtgc gcgcgaaacc     300
gtgatggcgg gcaaagcact ggattattgg ggtcagggca ccctggtgac cgtgagcagc     360
gcgagcacca aaggcccgag cgcgagcacc aaaggcccga gcgtgtttcc gctggcacct     420
agttcgaaat caacgagcgg tggcaccgcg gctctgggct gcctggtgaa agattatttc     480
ccggaacctg ttaccgtgag ctggaacagc ggtgcgttga cgagtggtgt gcatacctt     540
cccgcagttc tgcaatcgag cggcctgtac tcactgagca gcgtggttac ggtcccgagc     600
agtagcctgg gtacacagac ctatatttgt aacgtgaacc acaagccttc gaacacgaaa     660
gttgacaaac gcgtggaacc gaagagcagc ggttctgcac cagctcctgg atctgcgcct     720
acctatcgcg cgagcagcct gccgcagtcg tttctgctga aaagcctgga acaggtgcgc     780
aagattcagg gtgacggcgc agctctgcaa gaaaaactgt gcgcgaccta caaattgtgc     840
cacccctgag gaactggttct gctgggccat agtctgggca ttccgtgggc gccgctgagc     900
agctgcccgt cgcaggcatt gcagctggct ggctgtctga gccagttaca tagcggtctg     960
tttctgtatc agggcctgct gcaagcgctg aaggcatca gtcctgagtt gggtccgacc    1020
ctggatacct tacagctgga tgtggcggat tcgcaaccac ccatttggca gcagatggaa    1080
gaattgggca tggctccggc gttgcagccg acccagggcg cgatgcctgc gtttgcaagc    1140
gcttttcagc gccgcgcggg tggggtgctg gtggcgtcgc acttgcagag cttcctggaa    1200
gtgagctacc gtgtcctgcg ccatctggca cagcct                              1236
```

<210> SEQ ID NO 71
<211> LENGTH: 412

<212> TYPE: PRT
<213> ORGANISM: Homo sapiens

<400> SEQUENCE: 71

Gln Val Gln Leu Val Gln Ser Gly Gly Gly Pro Val Lys Pro Gly Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
            100                 105                 110

Gly Thr Leu Val Thr Val Ser Ser Ala Ser Thr Lys Gly Pro Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Ser Gly Ser Ala Pro Ala Pro Gly Ser Ala Pro
225                 230                 235                 240

Thr Tyr Arg Ala Ser Ser Leu Pro Gln Ser Phe Leu Leu Lys Ser Leu
                245                 250                 255

Glu Gln Val Arg Lys Ile Gln Gly Asp Gly Ala Ala Leu Gln Glu Lys
            260                 265                 270

Leu Cys Ala Thr Tyr Lys Leu Cys His Pro Glu Glu Leu Val Leu Leu
        275                 280                 285

Gly His Ser Leu Gly Ile Pro Trp Ala Pro Leu Ser Ser Cys Pro Ser
    290                 295                 300

Gln Ala Leu Gln Leu Ala Gly Cys Leu Ser Gln Leu His Ser Gly Leu
305                 310                 315                 320

Phe Leu Tyr Gln Gly Leu Leu Gln Ala Leu Glu Gly Ile Ser Pro Glu
                325                 330                 335

Leu Gly Pro Thr Leu Asp Thr Leu Gln Leu Asp Val Ala Asp Phe Ala
            340                 345                 350

Thr Thr Ile Trp Gln Gln Met Glu Glu Leu Gly Met Ala Pro Ala Leu
        355                 360                 365

Gln Pro Thr Gln Gly Ala Met Pro Ala Phe Ala Ser Ala Phe Gln Arg
    370                 375                 380

Arg Ala Gly Gly Val Leu Val Ala Ser His Leu Gln Ser Phe Leu Glu
385                 390                 395                 400

Val Ser Tyr Arg Val Leu Arg His Leu Ala Gln Pro
                405                 410

<210> SEQ ID NO 72
<211> LENGTH: 666
<212> TYPE: DNA
<213> ORGANISM: Homo sapiens

<400> SEQUENCE: 72
gatatcgttc tgacccaatc tccgggtacg ctgagcctga gcccgggcga aaccgcgacc      60
ctgagctgcc gcgcgagcca aagcgtgggt tctaatctgg cttggtatca gcagaaaccg     120
ggtcaggccc cgcgcctgct gatctatggg gcgagcacgg gggctaccgg cgttccggcg     180
cgctttagtg gcagtcgcag cggcaccgat tttacccctga ccattacaag tctgcagccg     240
gaagattttg cgacctatta ttgccagcaa tattatagct tcctggcgaa aacctttggt     300
cagggcaccc agctggaaat taaacgcacc gtggcggcac ccagcgtgac ggtggcggca     360
cccagcgtgt ttatttttcc tcccagtgat gaacagctga aaagcgggac cgcgagtgtt     420
gtgtgcctgt tgaacaactt ctatcctcgc gaagcgaaag tgcagtggaa agtggataac     480
gcattgcaga gcggcaacag tcaggaaagc gttactgaac aggatagcaa agatagtacg     540
tacagcttga gcaacactct gaccctgagt aaagcggatt atgaaaaaca taaagtgtat     600
gcatgcgaag ttacgcatca ggggctgagc agtccggtga caaagagctt taaccgcggc     660
gaaagc                                                                666

<210> SEQ ID NO 73
<211> LENGTH: 222
<212> TYPE: PRT
<213> ORGANISM: Homo sapiens

<400> SEQUENCE: 73

Asp Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg Thr Val Ala
            100                 105                 110

Ala Pro Ser Val Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Asn Thr Leu Thr Leu Ser Lys Ala
            180                 185                 190

Asp Tyr Glu Lys His Lys Val Tyr Ala Cys Glu Val Thr His Gln Gly
           195                 200                 205

Leu Ser Ser Pro Val Thr Lys Ser Phe Asn Arg Gly Glu Ser
    210                 215                 220

<210> SEQ ID NO 74
<211> LENGTH: 1209
<212> TYPE: DNA
<213> ORGANISM: Homo sapiens

<400> SEQUENCE: 74
caagttcagc tggttcagag cggtggcggc ccggtgaaac caggtggcag cctgcgtctg      60
tcctgcgcgg cgagcggttt tatgtttcgt gcgtatagca tgaactgggt gcgccaggcg     120
ccgggcaaag gcctggaatg ggtgagcagc attagcagca gtggccgcta tattcattat     180
gccgacagtg ttaaaggtcg ttttaccatt tctcgtgaca atgcgaaaaa cagcctgtat     240
ctgcaaatga atagcctgcg cgcggaagac accgcggtgt actactgtgc gcgcgaaacc     300
gtgatggcgg gcaaagcact ggattattgg ggtcaggca cctggtgac cgtgagcagc      360 gcgagcacca aaggcccgag cgcgagcacc aaaggcccga gcgtgtttcc gctggcacct    420
agttcgaaat caacgagcgg tggcaccgcg gctctgggct gcctggtgaa agattatttc    480
ccggaacctg ttaccgtgag ctggaacagc ggtgcgttga cgagtggtgt gcataccttt    540
cccgcagttc tgcaatcgag cggcctgtac tcactgagca gcgtggttac ggtcccgagc    600
agtagcctgg gtacacagac ctatatttgt aacgtgaacc acaagccttc gaacacgaaa    660
gttgacaaac gcgtggaacc gaagagctgc ggttctgcac cagctcctgg atcttcatac    720
aacctgctgg gcttcctgca acgtagcagt aactttcaga gccagaagct gttatggcaa    780
ctgaacggcc gcctggagta ctgcctgaag gatcgcatga actttgatat tccggaagaa    840
attaaacagc tgcaacagtt ccagaaagaa gatgcggcgc tgaccattta tgaaatgctg    900
caaaacattt ttgcgatttt tcgccaagat agtagtagca ccggctggaa cgaaaccatt    960
gtggaaaacc tgctcgccaa cgtgtaccat cagattaacc acctgaagac cgtgctggaa   1020
gaaaaactgg aaaagaaga ttttacccgc ggcaaactga tgagcagcct gcatctgaaa   1080
cgctattatg ccgcattcct ccattatctg aaagccaaag agtattccca ctgtgcttgg   1140
accattgttc gcgtggaaat tctgcgcaac ttttatttta ttaaccgcct gaccggctat   1200
ctgcgcaac                                                           1209

<210> SEQ ID NO 75
<211> LENGTH: 402
<212> TYPE: PRT
<213> ORGANISM: Homo sapiens

<400> SEQUENCE: 75

Gln Val Gln Leu Val Gln Ser Gly Gly Gly Pro Val Lys Pro Gly Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Glu Thr Val Met Ala Gly Lys Ala Leu Asp Tyr Trp Gly Gln Gly
        100                 105                 110

Thr Leu Val Thr Val Ser Ser Ala Ser Thr Lys Gly Pro Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Gly Ser Ala Pro Ala Pro Gly Ser Ser Tyr Asn
225                 230                 235                 240

Leu Leu Gly Phe Leu Gln Arg Ser Ser Asn Phe Gln Ser Gln Lys Leu
                245                 250                 255

Leu Trp Gln Leu Asn Gly Arg Leu Glu Tyr Cys Leu Lys Asp Arg Met
            260                 265                 270

Asn Phe Asp Ile Pro Glu Glu Ile Lys Gln Leu Gln Gln Phe Gln Lys
        275                 280                 285

Glu Asp Ala Ala Leu Thr Ile Tyr Glu Met Leu Gln Asn Ile Phe Ala
    290                 295                 300

Ile Phe Arg Gln Asp Ser Ser Ser Thr Gly Trp Asn Glu Thr Ile Val
305                 310                 315                 320

Glu Asn Leu Leu Ala Asn Val Tyr His Gln Ile Asn His Leu Lys Thr
                325                 330                 335

Val Leu Glu Glu Lys Leu Glu Lys Glu Asp Phe Thr Arg Gly Lys Leu
            340                 345                 350

Met Ser Ser Leu His Leu Lys Arg Tyr Tyr Gly Arg Ile Leu His Tyr
        355                 360                 365

Leu Lys Ala Lys Glu Tyr Ser His Cys Ala Trp Thr Ile Val Arg Val
    370                 375                 380

Glu Ile Leu Arg Asn Phe Tyr Phe Ile Asn Arg Leu Thr Gly Tyr Leu
385                 390                 395                 400

Arg Asn

<210> SEQ ID NO 76
<211> LENGTH: 666
<212> TYPE: DNA
<213> ORGANISM: Homo sapiens

<400> SEQUENCE: 76
gatatcgttc tgacccaatc tccgggtacg ctgagcctga gcccgggcga aaccgcgacc    60
ctgagctgcc gcgcgagcca aagcgtgggt tctaatctgg cttggtatca gcagaaaccg   120
ggtcaggccc cgcgcctgct gatctatggg gcgagcacgg gggctaccgg cgttccggcg   180
cgctttagtg gcagtcgcag cggcaccgat tttaccctga ccattacaag tctgcagccg   240

```
gaagattttg cgacctatta ttgccagcaa tattatagct tcctggcgaa aacctttggt      300
cagggcaccc agctggaaat taaacgcacc gtggcggcac ccagcgtgac ggtggcggca      360
cccagcgtgt ttattttcc tcccagtgat gaacagctga aaagcgggac cgcgagtgtt      420
gtgtgcctgt tgaacaactt ctatcctcgc gaagcgaaag tgcagtggaa agtggataac      480
gcattgcaga gcggcaacag tcaggaaagc gttactgaac aggatagcaa agatagtacg      540
tacagcttga gcaacactct gaccctgagt aaagcggatt atgaaaaaca taaagtgtat      600
gcatgcgaag ttacgcatca ggggctgagc agtccggtga caaagagctt taaccgcggc      660
gaatgc                                                                 666

<210> SEQ ID NO 77
<211> LENGTH: 222
<212> TYPE: PRT
<213> ORGANISM: Homo sapiens

<400> SEQUENCE: 77

Asp Ile Val Leu Thr Gln Ser Pro Gly Thr Leu Ser Leu Ser Pro Gly
 1               5                  10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg Thr Val Ala
            100                 105                 110

Ala Pro Ser Val Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Asn Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 78
<211> LENGTH: 1209
<212> TYPE: DNA
<213> ORGANISM: Homo sapiens

<400> SEQUENCE: 78
caagttcagc tggttcagag cggtggcggc ccggtgaaac aggtggcag cctgcgtctg       60 tcctgcgcgg cgagcggttt tatgtttcgt gcgtatagca tgaactgggt gcgccaggcg     120
ccgggcaaag gcctggaatg ggtgagcagc attagcagca gtggccgcta tattcattat     180
```

```
gccgacagtg ttaaaggtcg ttttaccatt tctcgtgaca atgcgaaaaa cagcctgtat    240
ctgcaaatga atagcctgcg cgcggaagac accgcggtgt actactgtgc gcgcgaaacc    300
gtgatggcgg gcaaagcact ggattattgg ggtcagggca ccctggtgac cgtgagcagc    360
gcgagcacca aaggcccgag cgcgagcacc aaaggcccga gcgtgtttcc gctggcacct    420
agttcgaaat caacgagcgg tggcaccgcg gctctgggct gcctggtgaa agattatttc    480
ccggaacctg ttaccgtgag ctggaacagc ggtgcgttga cgagtggtgt gcataccttt    540
cccgcagttc tgcaatcgag cggcctgtac tcactgagca gcgtggttac ggtcccgagc    600
agtagcctgg gtacagacac ctatatttgt aacgtgaacc acaagccttc gaacacgaaa    660
gttgacaaac gcgtggaacc gaagagcagc ggttctgcac cagctcctgg atcttcatac    720
aacctgctgg cttcctgca acgtagcagt aactttcaga gccagaagct gttatggcaa    780
ctgaacggcc gcctggagta ctgcctgaag gatcgcatga actttgatat tccggaagaa    840
attaaacagc tgcaacagtt ccagaaagaa gatgcggcgc tgaccattta tgaaatgctg    900
caaaacattt ttgcgatttt tcgccaagat agtagtagca ccggctggaa cgaaaccatt    960
gtggaaaacc tgctcgccaa cgtgtaccat cagattaacc acctgaagac cgtgctggaa   1020
gaaaaactgg aaaagaagaa ttttacccgc ggcaaactga tgagcagcct gcatctgaaa   1080
cgctattatg ccgcattcct ccattatctg aaagccaaag agtattccca ctgtgcttgg   1140
accattgttc gcgtggaaat tctgcgcaac ttttatttta ttaaccgcct gaccggctat   1200
ctgcgcaac                                                           1209
```

<210> SEQ ID NO 79
<211> LENGTH: 403
<212> TYPE: PRT
<213> ORGANISM: Homo sapiens

<400> SEQUENCE: 79

```
Gln Val Gln Leu Val Gln Ser Gly Gly Gly Pro Val Lys Pro Gly Gly
1               5                   10                  15

Ser Leu Arg Leu Ser Cys Ala Ala Ser Gly Phe Met Phe Arg Ala Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Arg Tyr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Met Ala Gly Lys Ala Leu Asp Tyr Trp Gly Gln
            100                 105                 110

Gly Thr Leu Val Thr Val Ser Ser Ala Ser Thr Lys Gly Pro Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
```

```
                180                 185                 190
Ser Ser Val Val Thr Val Pro Ser Ser Leu Gly Thr Gln Thr Tyr
        195                 200                 205
Ile Cys Asn Val Asn His Lys Pro Ser Asn Thr Lys Val Asp Lys Arg
    210                 215                 220
Val Glu Pro Lys Ser Ser Gly Ser Ala Pro Ala Pro Gly Ser Ser Tyr
225                 230                 235                 240
Asn Leu Leu Gly Phe Leu Gln Arg Ser Ser Asn Phe Gln Ser Gln Lys
                245                 250                 255
Leu Leu Trp Gln Leu Asn Gly Arg Leu Glu Tyr Cys Leu Lys Asp Arg
            260                 265                 270
Met Asn Phe Asp Ile Pro Glu Glu Ile Lys Gln Leu Gln Gln Phe Gln
                275                 280                 285
Lys Glu Asp Ala Ala Leu Thr Ile Tyr Glu Met Leu Gln Asn Ile Phe
        290                 295                 300
Ala Ile Phe Arg Gln Asp Ser Ser Ser Thr Gly Trp Asn Glu Thr Ile
305                 310                 315                 320
Val Glu Asn Leu Leu Ala Asn Val Tyr His Gln Ile Asn His Leu Lys
                325                 330                 335
Thr Val Leu Glu Glu Lys Leu Glu Lys Glu Asp Phe Thr Arg Gly Lys
            340                 345                 350
Leu Met Ser Ser Leu His Leu Lys Arg Tyr Tyr Gly Arg Ile Leu His
                355                 360                 365
Tyr Leu Lys Ala Lys Glu Tyr Ser His Cys Ala Trp Thr Ile Val Arg
        370                 375                 380
Val Glu Ile Leu Arg Asn Phe Tyr Phe Ile Asn Arg Leu Thr Gly Tyr
385                 390                 395                 400

Leu Arg Asn

<210> SEQ ID NO 80
<211> LENGTH: 666
<212> TYPE: DNA
<213> ORGANISM: Homo sapiens

<400> SEQUENCE: 80
gatatcgttc tgacccaatc tccgggtacg ctgagcctga gcccgggcga aaccgcgacc      60
ctgagctgcc gcgcgagcca aagcgtgggt tctaatctgg cttggtatca gcagaaaccg     120
ggtcaggccc cgcgcctgct gatctatggg gcgagcacgg gggctaccgg cgttccggcg     180
cgctttagtg gcagtcgcag cggcaccgat tttaccctga ccattacaag tctgcagccg     240
gaagattttg cgacctatta ttgccagcaa tattatagct tcctggcgaa aacctttggt     300
cagggcaccc agctggaaat taaacgcacc gtggcggcac ccagcgtgac ggtggcggca     360
cccagcgtgt ttatttttcc tcccagtgat gaacagctga aaagcgggac cgcgagtgtt     420
gtgtgcctgt gaacaacttc tatcctcgc gaagcgaaag tgcagtggaa agtggataac     480
gcattgcaga gcggcaacag tcaggaaagc gttactgaac aggatagcaa agatagtacg     540
tacagcttga gcaacactct gaccctgagt aaagcggatt atgaaaaaca taagtgtat     600
gcatgcgaag ttacgcatca ggggctgagc agtccggtga caaagagctt taaccgcggc     660
gaaagc                                                                666

<210> SEQ ID NO 81
<211> LENGTH: 222
<212> TYPE: PRT
```

<213> ORGANISM: Homo sapiens

<400> SEQUENCE: 81

Asp Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Gly Ala Thr Gly Val Pro Ala Arg Phe Ser Gly
    50                  55                  60

Ser Arg Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Tyr Ser Phe Leu Ala
                85                  90                  95

Lys Thr Phe Gly Gln Gly Thr Gln Leu Glu Ile Lys Arg Thr Val Ala
            100                 105                 110

Ala Pro Ser Val Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Asn Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Ser
    210                 215                 220

<210> SEQ ID NO 82
<211> LENGTH: 1275
<212> TYPE: DNA
<213> ORGANISM: Homo sapiens

<400> SEQUENCE: 82
gaggtgcagc tggtgcagtc tggggggaggc ttggtacagc ctggcaggtc cctgagactc      60
tcctgcacag cctctggatt caccttggat gattatgcca tgcactgggt ccggcaagct     120
ccagggaagg gcctggagtg ggtctcaggt attagttgga atggtggtag cgtagtctat     180
gcggactctg tcaggggccg attcaccatc tccagagaca acgccaagaa ctccctgtat     240
ctgcaaatga acagtctgag aactgaggac acggccgtct attactgtgc gagagattac     300
ggttactacg gtatggacgt ctggggccaa ggaaccctgg tcaccgtctc ctcatcggcc     360
acattggccg cctccaccaa gggcccatcg gtcttccccc tggcaccctc ctccaagagc     420
acctctgagg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaga     660
gttgagccca aatcttgtgg ttctgcacca gctcctggat cttttccgac cattccgctg     720
agccgcctgt tcgataacgc gatgctgcgc gcccaccgcc tgcatcaact ggcctttgat     780

```
acctatcagg agtttgagga agcgtacatc ccgaaggaac agaaatattc ttttctgcag    840
aacccacaga cgagcctgtg ctttagcgaa tctatcccga ccccgtccaa ccgcgaagaa    900
acccaacaga agtctaacct ggaactgctg cgtatctctc tgctgctgat tcaatcctgg    960
ctggaaccgg ttcaatttct gcgtagcgtg tttgcgaact ctctggtgta tggcgcgtct   1020
gactctaacg tgtatgacct gctgaaagat ctggaagaag gcatccaaac tctgatgggc   1080
cgtctggagg acggctctcc acgtaccggc cagatcttta aacagaccta tagcaaattt   1140
gacaccaatt ctcacaacga tgatgcgctg ctgaaaaact atggcctgct gtattgcttc   1200
cgtaaagaca tggataaagt tgaaacgttc ctgcgcattg ttcagtgccg ttccgtggag   1260
ggctcctgcg gcttc                                                   1275
```

<210> SEQ ID NO 83
<211> LENGTH: 425
<212> TYPE: PRT
<213> ORGANISM: Homo sapiens

<400> SEQUENCE: 83

```
Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Gly Gly Ser Val Val Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Tyr Cys
                85                  90                  95

Ala Arg Asp Tyr Gly Tyr Tyr Gly Met Asp Val Trp Gly Gln Gly Thr
            100                 105                 110

Leu Val Thr Val Ser Ser Ala Thr Leu Ala Ala Ser Thr Lys Gly
        115                 120                 125

Pro Ser Val Phe Pro Leu Ala Pro Ser Ser Lys Ser Thr Ser Glu Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Gly Ser Ala Pro Ala Pro Gly Ser Phe Pro Thr Ile Pro Leu
225                 230                 235                 240

Ser Arg Leu Phe Asp Asn Ala Met Leu Arg Ala His Arg Leu His Gln
                245                 250                 255

Leu Ala Phe Asp Thr Tyr Gln Glu Phe Glu Glu Ala Tyr Ile Pro Lys
            260                 265                 270

Glu Gln Lys Tyr Ser Phe Leu Gln Asn Pro Gln Thr Ser Leu Cys Phe
```

Ser Glu Ser Ile Pro Thr Pro Ser Asn Arg Glu Glu Thr Gln Gln Lys
            275                 280                 285
290

Ser Asn Leu Glu Leu Leu Arg Ile Ser Leu Leu Leu Ile Gln Ser Trp
305                 310                 315                 320

Leu Glu Pro Val Gln Phe Leu Arg Ser Val Phe Ala Asn Ser Leu Val
                    325                 330                 335

Tyr Gly Ala Ser Asp Ser Asn Val Tyr Asp Leu Leu Lys Asp Leu Glu
                340                 345                 350

Glu Gly Ile Gln Thr Leu Met Gly Arg Leu Glu Asp Gly Ser Pro Arg
            355                 360                 365

Thr Gly Gln Ile Phe Lys Gln Thr Tyr Ser Lys Phe Asp Thr Asn Ser
370                 375                 380

His Asn Asp Asp Ala Leu Leu Lys Asn Tyr Gly Leu Leu Tyr Cys Phe
385                 390                 395                 400

Arg Lys Asp Met Asp Lys Val Glu Thr Phe Leu Arg Ile Val Gln Cys
                405                 410                 415

Arg Ser Val Glu Gly Ser Cys Gly Phe
                420                 425

<210> SEQ ID NO 84
<211> LENGTH: 648
<212> TYPE: DNA
<213> ORGANISM: Homo sapiens

<400> SEQUENCE: 84
gatattgtga tgacccagtc tccatcttcc gtgtctgcat ctgttggaga cagagtcacc    60
atcacttgtc gggcgagtca gaatattggc agctggttag cctggtatca gcagaaacca   120
ggtaacgccc ctaagttgtt gatctataga gcatccaatt tgcgaagtgg ggtcccatca   180
aggttcagcg gcagtggctc tgggacagat ttcactctta ccatcagcag cctgcagcct   240
gaagatttcg caacttactt ttgtcaacag gctacctttt tccctctcac tttcggcgga   300
gggacccggg tggatatcaa acgttctaga gctgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcaacacc   540
ctgacgctga gcaaagcaga ctacgagaaa cacaaagtct acgcctgcga agtcacccat   600
cagggcctga gttcgcccgt cacaaagagc ttcaacaggg gagagtgt              648

<210> SEQ ID NO 85
<211> LENGTH: 216
<212> TYPE: PRT
<213> ORGANISM: Homo sapiens

<400> SEQUENCE: 85

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Gly Ser Trp
            20                  25                  30

Leu Ala Trp Tyr Gln Gln Lys Pro Gly Asn Ala Pro Lys Leu Leu Ile
        35                  40                  45

Tyr Arg Ala Ser Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Ala Thr Ile Phe Pro Leu
                 85                  90                  95

Thr Phe Gly Gly Gly Thr Arg Val Asp Ile Lys Arg Ser Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Asn Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 86
<211> LENGTH: 1275
<212> TYPE: DNA
<213> ORGANISM: Homo sapiens

<400> SEQUENCE: 86
gaggtgcagc tggtgcagtc tggggggaggc ttggtacagc ctggcaggtc cctgagactc     60
tcctgcacag cctctggatt caccttttgat gattatgcca tgcactgggt ccggcaagct    120
ccagggaagg gcctggagtg gtctcaggt attagttgga atggtggtag cgtagtctat    180
gcggactctg tcaggggccg attcaccatc tccagagaca cgccaagaa ctccctgtat    240 ctgcaaatga acagtctgag aactgaggac acggccgtct attactgtgc gagagattac    300
ggttactacg gtatggacgt ctggggccaa ggaaccctgg tcaccgtctc ctcatcggcc    360
acattggccg cctccaccaa gggcccatcg gtcttccccc tggcaccctc tccaagagc    420 acctctgagg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaga    660 gttgagccca aatctagtgg ttctgcacca gctcctggat cttttccgac cattccgctg    720
agccgcctgt tcgataacgc gatgctgcgc gcccaccgcc tgcatcaact ggcctttgat    780
acctatcagg agtttgagga agcgtacatc ccgaaggaac agaaatattc tttctgcag    840 aacccacaga cgagcctgtg ctttagcgaa tctatcccga ccccgtccaa ccgcgaagaa    900
acccaacaga agtctaacct ggaactgctg cgtatctctc tgctgctgat tcaatcctgg    960
ctggaaccgg ttcaatttct cgtagcgtg tttgcgaact ctctggtgta tggcgcgtct   1020
gactctaacg tgtatgacct gctgaaagat ctggaagaag gcatccaaac tctgatgggc   1080
cgtctggagg acggctctcc acgtaccggc cagatcttta acagacccta tagcaaattt   1140
gacaccaatt ctcacaacga tgatgcgctg ctgaaaaact atggcctgct gtattgcttc   1200
cgtaaagaca tggataaagt tgaaacgttc ctgcgcattg ttcagtgccg ttccgtggag   1260

```
ggctcctgcg gcttc                                                    1275
```

<210> SEQ ID NO 87
<211> LENGTH: 425
<212> TYPE: PRT
<213> ORGANISM: Homo sapiens

<400> SEQUENCE: 87

```
Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Gly Ser Val Val Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Tyr Cys
                85                  90                  95

Ala Arg Asp Tyr Gly Tyr Tyr Gly Met Asp Val Trp Gly Gln Gly Thr
            100                 105                 110

Leu Val Thr Val Ser Ser Ala Ser Thr Lys Gly
        115                 120                 125

Pro Ser Val Phe Pro Leu Ala Pro Ser Ser Lys Ser Thr Ser Glu Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Ser Gly Ser Ala Pro Ala Pro Gly Ser Phe Pro Thr Ile Pro Leu
225                 230                 235                 240

Ser Arg Leu Phe Asp Asn Ala Met Leu Arg Ala His Arg Leu His Gln
                245                 250                 255

Leu Ala Phe Asp Thr Tyr Gln Glu Phe Glu Glu Ala Tyr Ile Pro Lys
            260                 265                 270

Glu Gln Lys Tyr Ser Phe Leu Gln Asn Pro Gln Thr Ser Leu Cys Phe
        275                 280                 285

Ser Glu Ser Ile Pro Thr Pro Ser Asn Arg Glu Glu Thr Gln Gln Lys
    290                 295                 300

Ser Asn Leu Glu Leu Leu Arg Ile Ser Leu Leu Ile Gln Ser Trp
305                 310                 315                 320

Leu Glu Pro Val Gln Phe Leu Arg Ser Val Phe Ala Asn Ser Leu Val
                325                 330                 335

Tyr Gly Ala Ser Asp Ser Asn Val Tyr Asp Leu Leu Lys Asp Leu Glu
            340                 345                 350

Glu Gly Ile Gln Thr Leu Met Gly Arg Leu Glu Asp Gly Ser Pro Arg
        355                 360                 365
```

Thr Gly Gln Ile Phe Lys Gln Thr Tyr Ser Lys Phe Asp Thr Asn Ser
    370                 375                 380

His Asn Asp Asp Ala Leu Leu Lys Asn Tyr Gly Leu Leu Tyr Cys Phe
385                 390                 395                 400

Arg Lys Asp Met Asp Lys Val Glu Thr Phe Leu Arg Ile Val Gln Cys
                405                 410                 415

Arg Ser Val Glu Gly Ser Cys Gly Phe
            420                 425

<210> SEQ ID NO 88
<211> LENGTH: 648
<212> TYPE: DNA
<213> ORGANISM: Homo sapiens

<400> SEQUENCE: 88
gatattgtga tgacccagtc tccatcttcc gtgtctgcat ctgttggaga cagagtcacc      60
atcacttgtc gggcgagtca gaatattggc agctggttag cctggtatca gcagaaacca     120
ggtaacgccc ctaagttgtt gatctataga gcatccaatt tgcgaagtgg ggtcccatca     180
aggttcagcg gcagtggctc tgggacagat ttcactctta ccatcagcag cctgcagcct     240
gaagatttcg caacttactt ttgtcaacag gctaccattt tccctctcac tttcggcgga     300
gggacccggg tggatatcaa acgttctaga gctgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcaacacc     540
ctgacgctga gcaaagcaga ctacgagaaa cacaaagtct acgcctgcga agtcacccat     600
cagggcctga gttcgcccgt cacaaagagc ttcaacaggg gagagagt                  648

<210> SEQ ID NO 89
<211> LENGTH: 216
<212> TYPE: PRT
<213> ORGANISM: Homo sapiens

<400> SEQUENCE: 89

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Gly Ser Trp
            20                  25                  30

Leu Ala Trp Tyr Gln Gln Lys Pro Gly Asn Ala Pro Lys Leu Leu Ile
        35                  40                  45

Tyr Arg Ala Ser Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Thr Ile Phe Pro Leu
                85                  90                  95

Thr Phe Gly Gly Gly Thr Arg Val Asp Ile Lys Arg Ser Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn

```
145                 150                 155                 160
Ser Gln Glu Ser Val Thr Glu Gln Asp Ser Lys Asp Ser Thr Tyr Ser
                165                 170                 175

Leu Ser Asn Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser
    210                 215

<210> SEQ ID NO 90
<211> LENGTH: 1275
<212> TYPE: DNA
<213> ORGANISM: Homo sapiens

<400> SEQUENCE: 90
caggtgcagc tggtgcagtc agggggaggc ctggtcaggc cgggggggtc cctgagactc      60
tcctgtgcag cctctggact catattcagt aattatagca tgaactgggt ccgccaggct     120
ccggggaagg gctggagtg gtctcatca ataagtagtg ctggtagtta caaatactac       180
acagactcag tgaagggccg attcaccatc tccagagaca cgccaagaa gtcactgtat     240 ctgcaaatga acagcctgag agtcgacgac acggccgtct attactgtgc aagaggggac    300
tatgatacgg gcatggagcc ctggggccaa ggcaccatgg tcaccgtctc ctcatcggcc    360
acattggccg cctccaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca aatcttgtgg ttctgcacca gctcctggat cttttccgac cattccgctg    720
agccgcctgt cgataacgc gatgctgcgc gccaccgcc tgcatcaact ggcctttgat      780
acctatcagg agtttgagga agcgtacatc ccgaaggaac agaaatattc ttttctgcag    840
aacccacaga cgagcctgtg ctttagcgaa tctatcccga ccccgtccaa ccgcgaagaa    900
acccaacaga gtctaacctg gaactgctg cgtatctctc tgctgctgat tcaatcctgg     960
ctggaaccgg ttcaatttct gcgtagcgtg tttgcgaact ctctggtgta tggcgcgtct   1020
gactctaacg tgtatgacct gctgaaagat ctggaagaag gcatccaaac tctgatgggc   1080
cgtctggagg acggctctcc acgtaccggc cagatcttta aacagaccta tagcaaattt   1140
gacaccaatt ctcacaacga tgatgcgctg ctgaaaaaact atggcctgct gtattgcttc   1200
cgtaaagaca tggataaagt tgaaacgttc ctgcgcattg ttcagtgccg ttccgtggag   1260
ggctcctgcg gcttc                                                    1275

<210> SEQ ID NO 91
<211> LENGTH: 425
<212> TYPE: PRT
<213> ORGANISM: Homo sapiens

<400> SEQUENCE: 91

Gln Val Gln Leu Val Gln Ser Gly Gly Gly Leu Val Arg Pro Gly Gly
1                5                  10                  15

Ser Leu Arg Leu Ser Cys Ala Ala Ser Gly Leu Ile Phe Ser Asn Tyr
            20                  25                  30
```

Ser Met Asn Trp Val Arg Gln Ala Pro Gly Lys Gly Leu Glu Trp Val
        35                  40                  45

Ser Ser Ile Ser Ser Ala Gly Ser Tyr Lys Tyr Tyr Thr Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Val Asp Thr Ala Val Tyr Tyr Cys
                85                  90                  95

Ala Arg Gly Asp Tyr Asp Thr Gly Met Glu Pro Trp Gly Gln Gly Thr
                100                 105                 110

Met Val Thr Val Ser Ser Ala Thr Leu Ala Ala Ser Thr Lys Gly
                115                 120                 125

Pro Ser Val Phe Pro Leu Ala Pro Ser Ser Lys Ser Thr Ser Glu Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
                210                 215                 220

Ser Cys Gly Ser Ala Pro Ala Pro Gly Ser Phe Pro Thr Ile Pro Leu
225                 230                 235                 240

Ser Arg Leu Phe Asp Asn Ala Met Leu Arg Ala His Arg Leu His Gln
                245                 250                 255

Leu Ala Phe Asp Thr Tyr Gln Glu Phe Glu Glu Ala Tyr Ile Pro Lys
                260                 265                 270

Glu Gln Lys Tyr Ser Phe Leu Gln Asn Pro Gln Thr Ser Leu Cys Phe
                275                 280                 285

Ser Glu Ser Ile Pro Thr Pro Ser Asn Arg Glu Glu Thr Gln Gln Lys
                290                 295                 300

Ser Asn Leu Glu Leu Leu Arg Ile Ser Leu Leu Leu Ile Gln Ser Trp
305                 310                 315                 320

Leu Glu Pro Val Gln Phe Leu Arg Ser Val Phe Ala Asn Ser Leu Val
                325                 330                 335

Tyr Gly Ala Ser Asp Ser Asn Val Tyr Asp Leu Leu Lys Asp Leu Glu
                340                 345                 350

Glu Gly Ile Gln Thr Leu Met Gly Arg Leu Glu Asp Gly Ser Pro Arg
                355                 360                 365

Thr Gly Gln Ile Phe Lys Gln Thr Tyr Ser Lys Phe Asp Thr Asn Ser
        370                 375                 380

His Asn Asp Asp Ala Leu Leu Lys Asn Tyr Gly Leu Leu Tyr Cys Phe
385                 390                 395                 400

Arg Lys Asp Met Asp Lys Val Glu Thr Phe Leu Arg Ile Val Gln Cys
                405                 410                 415

Arg Ser Val Glu Gly Ser Cys Gly Phe
                420                 425

<210> SEQ ID NO 92
<211> LENGTH: 648

<212> TYPE: DNA
<213> ORGANISM: Homo sapiens

<400> SEQUENCE: 92

```
gagctcgagc tcgtgtcgac gcagtctcca tcctccctgt ctgcatctgt gggagacaga    60
gtcaccatta cttgccgggc aagtcagagc attagcagga atttaaattg gtatcagcag   120
aaaccaggga aagcccctaa gctcctgatc tatggtgcat ccagattaga aagtggggtc   180
ccatcaaggt tcagtggcag tggttctggg acagacttca ctctcaccat caacagcctg   240
caacctgaag attttgcaac ttactactgt caacagagtt acagtacccc tctaactttt   300
ggccagggga cccgagtcga aattaaacgt gctgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata cgccctcca atcgggtaac   480
tcccaggaga gtgtcacaga gcaggacagc aaggacagca cctacagcct cagcaacacc   540
ctgacgctga gcaaagcaga ctacgagaaa cacaaagtct acgcctgcga agtcacccat   600
cagggcctga gttcgcccgt cacaaagagc ttcaacaggg gagagtgt                648
```

<210> SEQ ID NO 93
<211> LENGTH: 216
<212> TYPE: PRT
<213> ORGANISM: Homo sapiens

<400> SEQUENCE: 93

```
Glu Leu Val Ser Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Lys Pro Gly Lys Ala Pro Lys Leu Leu Ile
            35                  40                  45

Tyr Gly Ala Ser Arg Leu Glu Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Arg Val Glu Ile Lys Arg Ser Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Asn Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 94

<211> LENGTH: 1275
<212> TYPE: DNA
<213> ORGANISM: Homo sapiens

<400> SEQUENCE: 94

```
caggtgcagc tggtgcagtc agggggaggc ctggtcaggc cggggggtc cctgagactc      60
tcctgtgcag cctctggact catattcagt aattatagca tgaactgggt ccgccaggct     120
ccggggaagg ggctggagtg ggtctcatca ataagtagtg ctggtagtta caaatactac    180
acagactcag tgaagggccg attcaccatc tccagagaca acgccaagaa gtcactgtat    240
ctgcaaatga acagcctgag agtcgacgac acggccgtct attactgtgc aagaggggac    300
tatgatacgg gcatggagcc ctggggccaa ggcaccatgg tcaccgtctc ctcatcggcc    360
acattggccg cctccaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca atctagtgg ttctgcacca gctcctggat cttttccgac cattccgctg    720
agccgcctgt tcgataacgc gatgctgcgc gcccaccgcc tgcatcaact ggcctttgat    780
acctatcagg agtttgagga agcgtacatc ccgaaggaac agaaatattc ttttctgcag    840
aacccacaga cgagcctgtg ctttagcgaa tctatcccga cccgtccaa ccgcgaagaa    900
acccaacaga agtctaacct ggaactgctg cgtatctctc tgctgctgat tcaatcctgg    960
ctggaaccgg ttcaattct gcgtagcgtg tttgcgaact ctctggtgta tggcgcgtct   1020
gactctaacg tgtatgacct gctgaaagat ctggaagaag gcatccaaac tctgatgggc   1080
cgtctggagg acggctctcc acgtaccggc cagatcttta aacagaccta tagcaaattt   1140
gacaccaatt ctcacaacga tgatgcgctg ctgaaaaact atggcctgct gtattgcttc   1200
cgtaaagaca tggataaagt tgaaacgttc ctgcgcattg ttcagtgccg ttccgtggag   1260
ggctcctgcg gcttc                                                    1275
```

<210> SEQ ID NO 95
<211> LENGTH: 425
<212> TYPE: PRT
<213> ORGANISM: Homo sapiens

<400> SEQUENCE: 95

```
Gln Val Gln Leu Val Gln Ser Gly Gly Gly Leu Val Arg Pro Gly Gly
1               5                   10                  15

Ser Leu Arg Leu Ser Cys Ala Ala Ser Gly Leu Ile Phe Ser Asn Tyr
            20                  25                  30

Ser Met Asn Trp Val Arg Gln Ala Pro Gly Lys Gly Leu Glu Trp Val
        35                  40                  45

Ser Ser Ile Ser Ser Ala Gly Ser Tyr Lys Tyr Tyr Thr Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Val Asp Asp Thr Ala Val Tyr Tyr Cys
                85                  90                  95

Ala Arg Gly Asp Tyr Asp Thr Gly Met Glu Pro Trp Gly Gln Gly Thr
            100                 105                 110
```

```
Met Val Thr Val Ser Ser Ala Thr Leu Ala Ala Ser Thr Lys Gly
            115                 120                 125
Pro Ser Val Phe Pro Leu Ala Pro Ser Ser Lys Ser Thr Ser Glu Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
210                 215                 220
Ser Ser Gly Ser Ala Pro Ala Pro Gly Ser Phe Pro Thr Ile Pro Leu
225                 230                 235                 240
Ser Arg Leu Phe Asp Asn Ala Met Leu Arg Ala His Arg Leu His Gln
                245                 250                 255
Leu Ala Phe Asp Thr Tyr Gln Glu Phe Glu Glu Ala Tyr Ile Pro Lys
            260                 265                 270
Glu Gln Lys Tyr Ser Phe Leu Gln Asn Pro Gln Thr Ser Leu Cys Phe
        275                 280                 285
Ser Glu Ser Ile Pro Thr Pro Ser Asn Arg Glu Glu Thr Gln Gln Lys
290                 295                 300
Ser Asn Leu Glu Leu Leu Arg Ile Ser Leu Leu Leu Ile Gln Ser Trp
305                 310                 315                 320
Leu Glu Pro Val Gln Phe Leu Arg Ser Val Phe Ala Asn Ser Leu Val
                325                 330                 335
Tyr Gly Ala Ser Asp Ser Asn Val Tyr Asp Leu Leu Lys Asp Leu Glu
            340                 345                 350
Glu Gly Ile Gln Thr Leu Met Gly Arg Leu Glu Asp Gly Ser Pro Arg
        355                 360                 365
Thr Gly Gln Ile Phe Lys Gln Thr Tyr Ser Lys Phe Asp Thr Asn Ser
370                 375                 380
His Asn Asp Asp Ala Leu Leu Lys Asn Tyr Gly Leu Leu Tyr Cys Phe
385                 390                 395                 400
Arg Lys Asp Met Asp Lys Val Glu Thr Phe Leu Arg Ile Val Gln Cys
                405                 410                 415
Arg Ser Val Glu Gly Ser Cys Gly Phe
            420                 425

<210> SEQ ID NO 96
<211> LENGTH: 648
<212> TYPE: DNA
<213> ORGANISM: Homo sapiens

<400> SEQUENCE: 96
gagctcgagc tcgtgtcgac gcagtctcca tcctccctgt ctgcatctgt gggagacaga      60
gtcaccatta cttgccgggc aagtcagagc attagcaggt atttaaattg gtatcagcag     120
aaaccaggga agcccctaa gctcctgatc tatggtgcat ccagattaga aagtggggtc     180
ccatcaaggt tcagtggcag tggttctggg acagacttca ctctcaccat caacagcctg     240
caacctgaag attttgcaac ttactactgt caacagagtt acagtacccc tctaactttt     300
ggccagggga cccgagtcga aattaaacgt gctgtggctg caccatctgt cttcatcttc     360
```

```
ccgccatctg atgagcagtt gaaatctgga actgcctctg ttgtgtgcct gctgaataac    420
ttctatccca gagaggccaa agtacagtgg aaggtggata cgcccctcca atcgggtaac    480
tcccaggaga gtgtcacaga gcaggacagc aaggacagca cctacagcct cagcaacacc    540
ctgacgctga gcaaagcaga ctacgagaaa cacaaagtct acgcctgcga agtcacccat    600
cagggcctga gttcgcccgt cacaaagagc ttcaacaggg gagagagt                 648
```

<210> SEQ ID NO 97
<211> LENGTH: 216
<212> TYPE: PRT
<213> ORGANISM: Homo sapiens

<400> SEQUENCE: 97

Glu Leu Val Ser Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Lys Pro Gly Lys Ala Pro Lys Leu Leu Ile
            35                  40                  45

Tyr Gly Ala Ser Arg Leu Glu Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Arg Val Glu Ile Lys Arg Ser Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Asn Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser
    210                 215

<210> SEQ ID NO 98
<211> LENGTH: 372
<212> TYPE: DNA
<213> ORGANISM: Homo sapiens

<400> SEQUENCE: 98

```
caggtgcagc tgttgcagtc tggagctgag gtgaagaagc ctggggcctc agtgaaggtc    60
tcctgcaagg cttctggtta caccttacc agctatggta tcagctgggt gcgacaggcc    120
cctggacaag gacttgagtg ggtgggatgg atcaacactt acagcggtgg cacaaagtat    180
gcacagaagt tcagggcag ggtcaccatg accagggaca cgtcaattag cacagtctac    240
atggaattaa gtggactgaa atcagacgac acggccgtct attactgtgc gaggctcgga    300
```

```
cattgtcaga ggggaatttg ctccgatgct ctggacactt ggggccaagg caccctggtc    360
accgtctcct ca                                                        372
```

<210> SEQ ID NO 99
<211> LENGTH: 372
<212> TYPE: DNA
<213> ORGANISM: Homo sapiens

<400> SEQUENCE: 99

```
gaggtgcagc tgttgcagtc tggagctgag gtgaaggagc ctggggcctc agtgaaggtc    60
tcctgcaagg cttctggtta cacctttagc agctatggta tcagctgggt gcgacaggcc    120
cctggacaag gacttgagtg ggtgggacgg atcaacactt acaatggtaa cacaggctat    180
gcacagaggc tccagggcag agtcaccatg actacagaca catccacgag catagcctac    240
atggaagtga ggagcctgag atctgacgac acggccgtct attactgtgc gaggctcgga    300
cattgtcaga ggggaatttg ctccgatgct ctggacactt ggggccaagg caccatggtc    360
accgtctcct ca                                                        372
```

<210> SEQ ID NO 100
<211> LENGTH: 375
<212> TYPE: DNA
<213> ORGANISM: Homo sapiens

<400> SEQUENCE: 100

```
caggtgcagc tggtgcagtc tgggggaggc gtggtccaga ctggggggtc cctgagactc    60
tcctgtgccg cctctggatt cacccttcagg aattatggca tacactgggt ccgccaggct    120
ccaggcaagg ggctggagtg ggtagcaagt atatcatatg atggaagtaa taaatactat    180
gcagactccg tgaagggccg attcaccatc tccagagaca attccaggaa cacggtgcat    240
gtgcaaatgg acagtctgag aggtggggac acggccgtct attactgtgc gagagatgtg    300
cattactatg gttcggggag ttattataat gcttttgata tctggggcca agggaccctg    360
gtcaccgtct cctca                                                     375
```

<210> SEQ ID NO 101
<211> LENGTH: 360
<212> TYPE: DNA
<213> ORGANISM: Homo sapiens

<400> SEQUENCE: 101

```
gaggtgcagc tggtgcagtc tgggggaggc ttggtacagc ctggggggtc cctgagactc    60
tcctgtgcag cctctggatt cacctttagc agctatgcca tgagctgggt ccgccaggct    120
ccagggaagg gactggagtg gctgtcagtc atatcacatg atggaggttt tcaatattat    180
gcagactccg tgaagggccg attcaccgtc tccagagaca attccaagaa cacactttat    240
ctgcaaatga acagcctgag agctgaggac acggccgtct attactgtgc gagagcgggg    300
tggctacgac aatatggtat ggacgtctgg ggccaaggca ccctggtcac cgtctcctca    360
```

<210> SEQ ID NO 102
<211> LENGTH: 351
<212> TYPE: DNA
<213> ORGANISM: Homo sapiens

<400> SEQUENCE: 102

```
gaggtgcagc tggtgcagtc tggtacagag gttaaaaagc ccggggagtc tctgaagatc    60
tcctgtaaga tttctggata cagcttcacc gcctattgga tcgcctgggt gcgccagatg    120
```

```
cccgggaaag gcctggagtg gatggggatg atctggcctc ctgacgctga tgccagatac    180
agcccgtcct tccaaggcca ggtcaccttt tcagtcgaca agtccattag taccgcctac    240
ttgcagtggc acagcctgaa gacctcggac acggccgtct attactgtgc gagattgtat    300
agtgggagct actcccctg gggccaaggg accctggtca ccgtctcctc a              351
```

<210> SEQ ID NO 103
<211> LENGTH: 360
<212> TYPE: DNA
<213> ORGANISM: Homo sapiens

<400> SEQUENCE: 103

```
caggtgcagc tggtgcagtc tgggggaggc ccggtcaagc ctgggggggtc cctgagactc     60 tcctgtgcag cctctggatt catgttccgt gcctatagca tgaattgggt ccgccaggct    120
ccagggaagg ggctggagtg ggtctcatcc attagtagca gtggtcgtta catacactac    180
gcagactcag tgaagggccg attcaccatc tccagagaca acgccaagaa ctcactgtat    240
ctacaaatga acagcctgag agccgaggac acggccgtct attactgtgc gagagagaca    300
gtaatggctg ggaaggccct tgactactgg ggccaaggaa ccctggtcac cgtctcctca    360
```

<210> SEQ ID NO 104
<211> LENGTH: 324
<212> TYPE: DNA
<213> ORGANISM: Homo sapiens

<400> SEQUENCE: 104

```
gagctcgtgt tgacccagtc tccatcctcc ctgtctgcat ctgtgggaga cagagtcacc     60
attacttgcc gggcaagtca gagcattagc aggtatttaa attggtatca gcagaaacca    120
gggaaagccc ctaagctcct gatctatggt gcatccagat tagaaagtgg ggtcccatca    180
aggttcagtg gcagtggttc tgggacagat ttcactctca ccatcagcag tctgcaacct    240
gaagattttg caacttacta ctgtcaacag agtgacagtg tcccggtcac cttcggccaa    300
ggtacacgac tggagattaa acga                                           324
```

<210> SEQ ID NO 105
<211> LENGTH: 327
<212> TYPE: DNA
<213> ORGANISM: Homo sapiens

<400> SEQUENCE: 105

```
gacatcgtgt tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccctccgta cacttttggc    300 cagggggacaa agctggaaat caaacgt                                       327
```

<210> SEQ ID NO 106
<211> LENGTH: 330
<212> TYPE: DNA
<213> ORGANISM: Homo sapiens

<400> SEQUENCE: 106

```
gagctcgtgt tgacgcagtc tccaggcacc ctgtctttgt ctccagggga aagagccacc     60
```

```
ctctcctgca gggccagtca gagtatttc aactacgtag cctggtacca acagaaacct    120
ggccaggctc ccaggctcct catctatgat gcatccaaca gggccactgg cataccagcc    180
aggttcagtg gcagtgggtc tgggacagac ttcactctca ccatcagcag cctagagcct    240
gaagattttg cagtttatta ctgtcagcag cgtagcaagt ggcctcccac gtggacgttc    300
ggccaaggga cccgagtgga tatcaaacgt                                     330

<210> SEQ ID NO 107
<211> LENGTH: 327
<212> TYPE: DNA
<213> ORGANISM: Homo sapiens

<400> SEQUENCE: 107
gagctcgtgt tgacgcagtc tccaggcacc ctgtctttgt ctccagggga aagagccacc     60
ctctcctgca gggccagtga gaccgttagc agccggcagt tagcctggta ccagcagaaa    120
cctggccagg ctcccaggct cctcatctat ggtgcttcca gcagggccac tggcatccct    180
gacaggttca gtggcagtgg gtctgggaca gacttcactc tcaccatcag cagactggag    240
cctgaagatt ctgcagtgtt ttactgtcag cagtatggta gctcacctcg cactttcggc    300
ggagggacca agctggaaat caaacgt                                        327

<210> SEQ ID NO 108
<211> LENGTH: 327
<212> TYPE: DNA
<213> ORGANISM: Homo sapiens

<400> SEQUENCE: 108
gagctcgtgt tgacgcagtc tccaggcacc ctgtctttgt ctccagggga aagagccacc     60
ctctcctgca gggccagtca gagtgttagc agcagtcctt agcctggta ccagcagaaa    120 cctggccagg ctcccaggct cctcatctat ggtgcatcca gcagggccac tggcatccca    180
gacaggttca gtggcagtgg gtctgggaca gatttcactc tcaccatcag cagcctgcag    240
cctgaagatg ctgccacata ctactgccaa agtatagta gttacccgct caccttcggc    300
caagggacca aactggaaat taaacgt                                        327

<210> SEQ ID NO 109
<211> LENGTH: 327
<212> TYPE: DNA
<213> ORGANISM: Homo sapiens

<400> SEQUENCE: 109
gagctcgtgt tgacgcagtc tccaggcacc ctgtctttgt ctccggggga aacagccacc     60
ctctcttgca gggccagcca gagtgttggc agcaacttag cctggtacca gcagaaacct    120
ggccaggctc ccaggctcct catctatggt gcatccactg gggccactgg tgtcccagcc    180
aggttcagtg gcagtcgatc tgggacagac ttcactctca ctatcaccag cctgcagcct    240
gaagattttg caacttacta ttgtcaacag tattatagtt cctagctaa gacgttcggc    300 caagggaccc agctggaaat caaacgt                                        327

<210> SEQ ID NO 110
<211> LENGTH: 5240
<212> TYPE: DNA
<213> ORGANISM: Escherichia coli

<400> SEQUENCE: 110
cgaaaggccc agtctttcga ctgagccttt cgttttattt gatgcctggc gttccctact     60
```

```
ctcgcatggg gagaccccac actaccatcg gcgctacggc gtttcacttc tgagttcggc    120
atggggtcag gtgggaccac cgcgctactg acgccaggca aattctgttt tatcagaccg    180
cttctgcgtt ctgatttaat ctgtatcagg ctgaaaatct tctctcatcc gccaaaacag    240
ccaagcttcg aattcccata tggtaccagc tgcagatctc gagctctgca gaactcgagc    300
tcggatccta atatatacct ctttaatttt taataataaa gttaatcgat aattccggtc    360
gagtgcccac acagattgtc tgataaattg ttaaagagca gtgccgcttc gcttttctc    420 agcggcgctg tttcctgtgt gaaattgtta tccgctcaca attccacaca ttatacgagc    480
cggatgatta attgtcaaca gctcatttca agatctcgat cctctacgcc ggacgcatcg    540
tggccggcat caccggcgcc acaggtgcgg ttgctggcgc ctatatcgcc gacatcaccg    600
atggggaaga tcgggctcgc cacttcgggc tcatgagcgc ttgtttcggc gtgggtatgg    660
tggcaggccc cgtggccggg ggactgttgg gcgccatctc cttgcatgca ccattccttg    720
cggcggcggt gctcaacggc ctcaacctac tactgggctg cttcctaatg caggagtcgc    780
ataagggaga gcgtcgagat cccggacacc atcgaatggc gcaaaacctt tcgcggtatg    840
gcatgatagc gcccggaaga gagtcaattc agggtggtga atgtgaaacc agtaacgtta    900
tacgatgtcg cagagtatgc cggtgtctct tatcagaccg tttcccgcgt ggtgaaccag    960
gccagccacg tttctgcgaa aacgcgggaa aaagtggaag cggcgatggc ggagctgaat   1020
tacattccca accgcgtggc acaacaactg gcgggcaaac agtcgttgct gattggcgtt   1080
gccacctcca gtctggccct gcacgcgccg tcgcaaattg tcgcggcgat taaatctcgc   1140
gccgatcaac tgggtgccag cgtggtggtg tcgatggtag aacgaagcgg cgtcgaagcc   1200
tgtaaagcgg cggtgcacaa tcttctcgcg caacgcgtca gtgggctgat cattaactat   1260
ccgctggatg accaggatgc cattgctgtg gaagctgcct gcactaatgt tccggcgtta   1320
tttcttgatg tctctgacca gacacccatc aacagtatta ttttctccca tgaagacggt   1380
acgcgactgg gcgtggagca tctggtcgca ttgggtcacc agcaaatcgc gctgttagcg   1440
ggcccattaa gttctgtctc ggcgcgtctg cgtctggctg gctggcataa atatctcact   1500
cgcaatcaaa ttcagccgat agcggaacgg gaaggcgact ggagtgccat gtccggtttt   1560
caacaaacca tgcaaatgct gaatgagggc atcgttccca ctgcgatgct ggttgccaac   1620
gatcagatgg cgctgggcgc aatgcgcgcc attaccgagt ccgggctgcg cgttggtgcg   1680
gatatctcgg tagtgggata cgacgatacc gaagacagct catgttatat cccgccgtta   1740
accaccatca acaggatttt cgcctgctg gggcaaacca gcgtggaccg cttgctgcaa    1800
ctctctcagg ccaggcggt gaagggcaat cagctgttgc ccgtctcact ggtgaaaaga   1860
aaaaccaccc tggcgcccaa tacgcaaacc gcctctcccc gcgcgttggc cgattcatta   1920
atgcagctgg cacgacaggt ttcccgactg aaagcgggc agtgagcgca acgcaattaa   1980
tgtaagttag ctcactcatt aggcaccggg atctcgaccg atgcccttga gagccttcaa   2040
cccagtcagc tccttccggt gggcgcgggg catgactatc gtcgccgcac ttatgactgt   2100
cttctttatc atgcaactcg taggacaggt gccggcagcg ctctgggtca ttttcggcga   2160
ggaccgcttt cgctggagcg cgacgatgat cggcctgtcg cttgcggtat cggaatctt   2220 gcacgccctc gctcaagcct tcgtcactgg tcccgccacc aaacgtttcg gcgagaagca   2280
ggccattatc gccggcatgg cggccccacg ggtgcgcatg atcgtgctcc tgtcgttgag   2340
gacccggcta ggctggcggg gttgccttac tggttagcag aatgaatcac cgatacgcga   2400
```

```
gcgaacgtga agcgactgct gctgcaaaac gtctgcgacc tgagcaacaa catgaatggt    2460
cttcggtttc cgtgtttcgt aaagtctgga acgcggaag tcagcgccct gcaccattat    2520
gttccggatc tgcatcgcag gatgctgctg gctaccctgt ggaacaccta catctgtatt    2580
aacgaagcgc tggcattgac cctgagtgat ttttctctgg tcccgccgca tccataccgc    2640
cagttgttta ccctcacaac gttccagtaa ccgggcatgt tcatcatcag taacccgtat    2700
cgtgagcatc ctctctcgtt tcatcggtat cattaccccc atgaacagaa atccccctta    2760
cacggaggca tcagtgacca aacaggaaaa aaccgcccct aacatggccc gctttatcag    2820
aagccagaca ttaacgcttc tggagaaact caacgagctg gacgcggatg aacaggcaga    2880
catctgtgaa tcgcttcacg accacgctga tgagctttac cgcagctgcc tcgcgcgttt    2940
cggtgatgac ggtgaaaacc tctgacacat gcagctcccg gagacggtca cagcttgtct    3000
gtaagcggat gccgggagca gacaagcccg tcagggcgcg tcagcgggtg ttggcgggtg    3060
tcggggcgca gccatgaccc agtcacgtag cgatagcgga gtgtatactg gcttaactat    3120
gcggcatcag agcagattgt actgagagtg caccatatat gcggtgtgaa ataccgcaca    3180
gatgcgtaag gagaaaatac cgcatcaggc gctcttccgc ttcctcgctc actgactcgc    3240
tgcgctcggt cgttcggctg cggcgagcgg tatcagctca ctcaaaggcg gtaatacggt    3300
tatccacaga atcaggggat aacgcaggaa agaacatgtg agcaaaaggc cagcaaaagg    3360
ccaggaaccg taaaaaggcc gcgttgctgg cgtttttcca taggctccgc cccccctgacg    3420 agcatcacaa aaatcgacgc tcaagtcaga ggtggcgaaa cccgacagga ctataaagat    3480
accaggcgtt tcccctgga agctccctcg tgcgctctcc tgttccgacc ctgccgctta    3540
ccggatacct gtccgccttt ctcccttcgg gaagcgtggc gctttctcat agctcacgct    3600
gtaggtatct cagttcggtg taggtcgttc gctccaagct gggctgtgtg cacgaacccc    3660
ccgttcagcc cgaccgctgc gccttatccg gtaactatcg tcttgagtcc aacccggtaa    3720
gacacgactt atcgccactg gcagcagcca ctggtaacag gattagcaga gcgaggtatg    3780
taggcggtgc tacagagttc ttgaagtggt ggcctaacta cggctacact agaaggacag    3840
tatttggtat ctgcgctctg ctgaagccag ttaccttcgg aaaaagagtt ggtagctctt    3900
gatccggcaa acaaaccacc gctggtagcg gtggtttttt tgtttgcaag cagcagatta    3960
cgcgcagaaa aaaaggatct caagaagatc ctttgatctt ttctacgggg tctgacgctc    4020
agtggaacga aaactcacgt taagggattt tggtcatgaa caataaaact gtctgcttac    4080
ataaacagta atacaagggg tgttatgagc catattcaac gggaaacgtc ttgctctagg    4140
ccgcgattaa attccaacat ggatgctgat ttatatgggt ataaatgggc tcgcgataat    4200
gtcgggcaat caggtgcgac aatctatcga ttgtatggga agcccgatgc gccagagttg    4260
tttctgaaac atggcaaagg tagcgttgcc aatgatgtta cagatgagat ggtcagacta    4320
aactggctga cggcatttat gcctcttccg accatcaagc atttatccg tactcctgat    4380 gatgcatggt tactcaccac tgcgatcccc gggaaaacag cattccaggt attagaagaa    4440
tatcctgatt caggtgaaaa tattgttgat gcgctggcag tgttcctgcg ccggttgcat    4500
tcgattcctg tttgtaattg tccttttaac agcgatcgcg tatttcgtct cgctcaggcg    4560
caatcacgaa tgaataacgg tttggttgat gcgagtgatt ttgatgacga gcgtaatggc    4620
tggcctgttg aacaagtctg gaaagaaatg cataaacttt tgccattctc accggattca    4680
gtcgtcactc atggtgattt ctcacttgat aaccttattt ttgacgaggg gaaattaata    4740
ggttgtattg atgttggacg agtcggaatc gcagaccgat accaggatct tgccatccta    4800
```

```
tggaactgcc tcggtgagtt ttctccttca ttacagaaac ggcttttca aaaatatggt    4860 attgataatc ctgatatgaa taaattgcag tttcatttga tgctcgatga gtttttctaa    4920
gaattaattc atgagcggat acatatttga atgtatttag aaaaataaac aaataggggt    4980
tccgcgcaca tttccccgaa aagtgccacc tgaaattgta aacgttaata ttttgttaaa    5040
attcgcgtta aattttgtt aaatcagctc attttttaac caataggccg aaatcggcaa     5100
aatcccttat aaatcaaaag aatagaccga gatagggttg agtgttgttc cagtttggaa    5160
caagagtcca ctattaaaga acgtggactc caacgtcaaa gggcgaaaaa ccgtctatca    5220
gggcgatggc ccactacgtg                                                 5240
```

METHOD OF PREPARING AN ANTI-SERUM ALBUMIN FAB-EFFECTOR MOIETY FUSION CONSTRUCT

CROSS REFERENCE TO RELATED APPLICATIONS

This application is a divisional application of U.S. application Ser. No. 15/056,299 filed on Feb. 29, 2016, which is a continuation of International Application No. PCT/KR2014/008106 filed on Aug. 29, 2014, which claims priority to Korean Application No. 10-2013-0104112 filed on Aug. 30, 2013. The applications are incorporated herein by reference.

TECHNICAL FIELD

The present invention relates to antigen-binding fragment (Fab) and a Fab-effector fusion protein comprising thereof.

INCORPORATION BY REFERENCE OF SEQUENCE LISTING

The contents of the text file named "50527-501C01US_ST25.txt", which was created on Aug. 4, 2016 and filed on Sep. 13, 2016 with USPTO in U.S. application Ser. No. 15/056,299 and is 110 KB in size, are hereby incorporated by reference in their entireties.

BACKGROUND ART

Antigen-binding fragment (Fab) preparation is one of the most successful monoclonal antibody therapeutic agents. For example, Abciximab(ReoPro®), Ranibizumab(Lucentis®), and Certolizumab pegol(Cimzia®) etc. had already been approved as drugs in many countries. Furthermore, polyclonal Fab preparations including Abciximab(ReoPro®), Ranibizumab(Lucentis®) and Certolizumab pegol (Clmzia®) are commercially available in EU.

Conjugation of an exogenous effector domain may confer therapeutic effects to Fab fragments, when they form a Fab-effecter fusion format. Therefore, in fact, lots of antibody fragments in clinical development status are conjugated to an exogenous functional moiety. In such a Fab-fusion protein construct (or Fab-effector moieties construct), the antigen binding fragment may provide a target-specific delivery, and the fusion protein or (poly)peptide (effector domain) may provide therapeutic effects. Fusion domains originated from prokaryotic origin may include cytotoxins, for example, deBouganin (a de-immunized plant toxin) (see Entwistle et al., (2012) *Cancer Biother Radiopharm.* 27, 582-92), staphylococcal enterotoxin (SE) (see Ilack et al., (2003) *Toxicology.* 185, 161-174) or a mutant form of *Pseudomonas* exotoxin (see Choe et al., (1994) *Cancer Res.* 54, 3460-3467; see Kreitman et al., (1994) *Int. J. Cancer* 57, 856-864). In addition, fusion domains comprising polypeptides from eukaryotes, such as, scFv (see Lu et al., (2002) *J Immunolog Meth.* 267, 213-226) or cytokine (see Holzer et al., (1996) *Cytokine.* 8, 214-221; see Sjogaard et al., (1999) *Int J Oncol.* 15, 873-882), may function as therapeutics. Although radioactive isotope is chemically conjugated to Fab or (Fab')$_2$ fragment in general, cytotoxin, cytokine or enzyme is genetically fused to Fab or (Fab')$_2$. It is known that Fab molecules, unlike scFv, Fv or dsFv, can be produced with ease up to 1-2 g/L as a soluble form in the periplasm of *E. coli* (see Humphreys et al., *J. Immunol. Methods.* 209, 193-202; Carter et al., *Biotechnology* (N Y). 10, 163167; Venturi et al., J Mol Biol. 315, 1-8; Donzeau et al., *Methods Mol Biol.* 378, 14-31), or even in *Pseudomonas fluorescens* (see Retallack et al., *Prot Exp Purif.* 81, 157-165). Currently, lots of commercially available biological agents such as rhGH, insulin or various types of cytokines are being produced in *E. coli* (see Graumann and Premstaller, (2006) *Biotechnol J.* 1, 164-186; Chadd and Chamow, (2001) *Curr Opin Biotechnol.* 12, 188-194). In this regard, the genetic linkage of a therapeutic domain to a Fab fragment and other therapeutic agents has great advantage in the development of a new biological medicinal agent, and the improvement of the current biological drugs efficacy as well. Further, a Fab molecule might be fused with other antibody fragments such as scFv, Fv, dsFv or dAb to prepare bi-specific or tri-specific antibody molecule (see Lu et al., (2002) *J Immunolog Meth.* 267, 213-226). However, the expression of Fab-effector fusion proteins of which the effector is of eukaryotic origin in *E. coli* has been hampered because the effector domain could not be biologically functional due to inappropriate folding or the lack of glycosylation process in *E. coli*. Futhermore, the optimal fusion format to produce Fab-effector fusion proteins in *E. coli* periplasm has not yet been throughly studied. Most of serum proteins having molecular weight less than between 50 kDa and 60 kDa, such as, cytokines and growth factors, have a short half-life in vivo, for instance, from several minutes to several hours due to renal clearance. Thus, extending the serum half-life of therapeutic polypeptides or proteins is one of the most intensely studied areas in bio-pharmaceutical research (see Kontermann, (2012) Wiley, ISBN: 978-3-527-32849-9). For this purpose, various methods including pegylation, polysialylation, HESylation, glycosylation, or recombinant PEG analogue fused to flexible and hydrophilic amino acid chain (500 to 600 amino acids) have been developed (See Chapman, 2002; *Adv Drug Deliv Rev.* 54. 531~545; Schlapschy et al., (2007) *Prot Eng Des Sel.* 20, 273~283; Contermann (2011) *Curr Op Biotechnol.* 22, 868~876; Jevsevar et al., (2012) *Methods Mol Biol.* 901, 233~246). Furthermore, the FcRn-mediated recycling mechanism has been directly or indirectly employed in order to extend in vivo half-life of therapeutic proteins. Among serum proteins, it is known that a human serum albumin (HSA) and an immune globulin (in particular, IgG) have exceptionally a long half-life through the FcRn-mediated recycling mechanism. In a human body, the serum half-life of albumin is 19 days and that of an IgG molecule is between one week and almost 4 weeks depending on the subclass of IgG. Thus, these two molecules have been used as fusion partners to extend half-life of therapeutic proteins and/or (poly)peptides.

Recombinant hGH (~19 kDa) prepared in cytoplasm or the periplasm of *E. coli* has been used in clinics to treat diseases caused by the lack of growth hormones in infants and adults as well, after in vitro folding process (see Blethen et al., (1997) *J. Clin. Endocrinol. Metab.* 82, 418-420). One major inconvenience in rhGH administration is the daily injection due to the short period of half-life (<30 minutes). To extend the serum half-life of hGH, chemical conjugation of polyethylene glycol (see Clark et al., (1996) *J. Biol. Chem.* 271, 21969-21977; Pradhananga et al., 2002 *J Mol Endocrinol.* 29, 1114; Cho et al., 2011; Sondergaard et al., (2011) *J Clin Endocrinol Metabol.* 96, 681-688), and chemical conjugation of the modified hGH to the arm of Fab of humanized CovX-Body IgG (see Palanki et al., (2013) *Bioorg. Med. Chem. Lett.* 23, 402-406) had been attempted. In addition, the elongation of the half-life of hGH in serum has been successfully achieved by the genetic fusion of human serum albumin (HSA) (Albutropin®) or the polypepeptide sequences comprising hundreds of Pro-Ala-Ser (PAS) residues (PASylation) (see Osborn et al., 2002 *Eur J Pharmacol.* 456, 149-158; Anderson et al., (2011) *J Biol Chem.* 286, 5234-5241; Sleep et al., (2013) *Biochimica et Biophysica Acta.* 1830, 5526-5534; Schlapschy et al., (2013) *Protein Eng Des Sel.* 26, 489~501). The most well studied one in this category is VRS-317, a rGH genetically linked with XTEN amino acid sequences to the N-terminus and the C-terminus, which allows one month dosage regimen (see Schellenberger et al., (2007) *Nat Biotech.* 27, 1186-1190; Cleland et al., (2012) *J Pharm Sci.* 101, 2744-2754; Yuen et al., (2013) *J Clin Endocrinol Metab.* 98, 2595-2603). Also, hGH is associated with vascular disease (See Thomas J Merimee et. al., (1973), *Diabetes,* 22, 813-819) and CRETZFELDT-JAKOB disease (See John Powell-Jackson et al., 1985, *Lancet,* 2, 244-246). In addition, IFN-γ accelerates Graft-Versus-Host-Disease (See Bruce R.Blazar et. al., 2003, *The Journal of Immunology,* 171, 1272-1277) and IFN-α is related with autoimmune disease (See A Imagawa et al., 1995, *The Journal of clinical endocrinology & metabolism,* 80, 922-926). Also, GSCF is related with autoimmune disease (See Anke Franzke et al., 2003, *Blood,* 102, 734-739) and HCV associated with liver disease (See Van Thiel D H et al., 1995, *Hepato-gastroenterology,* 42, 907-912).

A Fab-fusion protein (or polypeptide) has a great potential as a therapeutic agent for treating chronical diseases which require a large dose of drugs for a long period of time, in particular, especially when the Fab-fusion protein can be produced in microorganism expression system with low cost. Despite such possible potent advantages of employing a Fab, however, there has been no attempt applying an anti-serum albumin (SA) Fab antibody in the development of a protein or a (poly)peptide drug having extended in vivo half-life. Herein, the inventors have completed the present invention by constructing a novel anti-serum albumin (SA) Fab-effector protein (or (poly)peptide) fusion constructs, and confirming the high-yield production of funtional fusion constructs in the periplasm of *E. coli*.

SUMMARY

The technical problem to be solved by the present invention is to provide a novel antigen binding fragment (Fab) having extended in vivo serum half-life.

Another technical problem to be solved by the present invention is to provide the Fab-effector moieties fusion construct which enables the optimal production in the periplasm of host cell.

Yet another technical problem to be solved by the present invention is to provide an expression vector and a host cell to produce the Fab-effector constructs in soluble form with high yield.

Yet another technical problem to be solved by the present invention is to provide a pharmaceutical composition comprising the fusion constructs above.

In order to solve the problems above, the present invention provides an optimal Fab-effector fusion construct (or format) for the periplasmic expression in *E. coli*, wherein the Fab has a heavy chain variable domain binding to heavy chain constant 1 domain ($C_{H1}$), and has a light chain variable domain binding to light chain constant domain ($C_L$).

In one embodiment of the present invention, a human anti-SA Fab was chosen as an antibody fragment, considering that the fusion of various therapeutic proteins to albumin or to albumin-binding moieties, such as small peptides or domain antibodies (dAb) has been shown to extend the half-lives of therapeutic proteins through the FcRn-mediated recycling mechanism (see Dennis et al., (2002) *Biochimica et Biophysica Acta.* 1830, 5526-5534; Sleep et al., (2013) *Biochimica et Biophysica Acta.* 1830, 5526-5534; Nguyen et al., (2006) *Protein Eng Des Sel.* 19, 291-297; Kontermann, (2011) *Curr Op Biotechnol.* 22, 868~876). According to the prior studies, a Fab fragment has an eleimination half-life of 16-20 h in humans(See Ujhelyi and Robert, (1995) *Clin Pharmacokinet.* 28, 483493) and ~3 h in rats after intravenous administration (see Nguyen et al., 2006 *Protein Eng Des Sel.* 19, 291~297). Surprisingly, the half-life of Fab (SL335) in this invention is 37 h in rats which is approximately 12-fold longer than conventional human Fabs, and thus it is reasonable to assume that SL335 might have a half-life of at least 160 200 h (6-8 days) in humans. In the meantime, two Vk domains, dAbr3 and dAbr16 possessing 13 nM and 1 mM of binding affinities to RSA, respectively, had been known to have the $t_{1/2}$ values of 53 h (dAbr3) and 43 h (dAbr16) in rats (see Holt et al., (2008) *Protein Eng Des Sel.* 21, 283-288). Moreover, the $t_{1/2b}$ of Ab Fab4D5-H with a 92 nM affinity to RSA was 26.9 h (see Nguyen et al., 2006). Therefore, it is implied that the in vivo functionality of SL335 is comparable to that of previously reported dAbs and peptides specific for SA. It is noteworthy that the $V_H$ and the $V_L$ of SL335 shared only a 65-67% amino acid homology at the full sequence level, and a ~50% amino acid homology at the complementarity determining region (CDR) level with the previously reported albumin-specific dAbs (data not shown). Specifically, the Fab specific for serum albumin (SA) in an embodiment of the present invention comprises a heavy chain variable domain which has an amino acid sequence selected from the group consisting of SEQ ID NO.1 (SA138 VH: QVQLLQSGAE VKKPGASVKV SCKASGYTFT SYGISWVRQA PGQGLEWVGW INTYSGGTKYA QKFQGRVTMT RDTSISTVYM ELSGLKSDDTAVY YCARLGHCQRGICSDAL DTWGQGTLVT VSS), SEQ ID NO.2 (SA139 VH: EVQLLQSGAE VKEPGASVKV SCKASGYTFS SYGISWVRQA PGQGLEWVGR INTYNGNTGYA QRLQGRVTMT TDTSTSIAYM EVRSLRSDDTAVY YCARLGHCQRGICSDAL DTWGQGTMVT VSS), SEQ ID NO.3 (SA140 VH: QVQLVQSGGG VVQTGGSLRL SCAASGFTFR NYGIHWVRQA PGKGLEWVAS ISYDGSNKYYA DSVKGRFTIS RDNSRNTVHV QMDSLRGGDTAVY YCARDVHYYGSGSYYNAF DIWGQGTLVT VSS), SEQ ID NO.4 (SA141 VH: QVQLVQSGGG LVQPGGSLRL SCAASGFTFS SYAMSWVRQA PGKGLEWLSV ISHDGGFQYYA DSVKGRFTVS RDNSKNTLYL QMNSLRAEDTAVY YCARAGWLRQYGM DVWGQGTLVT VSS), SEQ ID NO.5 (SL18 VH: EVQLVQSGTE VKKPGESLKI SCKISGYSFT AYWIAWVRQM PGKGLEWMGM IWPPDADARYS PSFQGQVTFS VDKSISTAYL QWHSLKTSDTAVY YCARLYSGSY SPWGQGTLVT VSS) and SEQ ID NO.6 (SL301, SL310 and SL335 VH: QVQLVQSGGG PVKPGGSLRL SCAASGFMFR AYSMNWVRQA PGKGLEWVSS ISSSGRYIHYA DSVKGRFTIS RDNAKNSLYL QMNSLRAEDTAVY YCARETVMAGKAL DYWGQGTLVT VSS); and a light chain variable domain which has an amino acid sequence selected from the group consisting of SEQ ID NO.7 (SA130: ELVLTQSPSS LSASVGDRVT ITCRASQSIS RYLNWYQQKP GKAPKLLIYG ASRLESGVPS RFSGSGSGTD FTLTISSLQP EDFATYYCQQ SDSVPVTFGQ GTRLEIKR), SEQ ID NO.8 (SA139 VL: DIVLTQSPSS LSASVGDRVT ITCRASQSIS SYLNWYQQKP GKAPKLLIYA ASSLQSGVPS RFSGSGSGTD FTLTISSLQP EDFATYYCQQ SYSTPPYTFGQ GTKLEIKR), SEQ ID NO.9 (SL18 VL: ELVLTQSPGT LSLSPGERAT LSCRASQSIF NYVAWYQQKP GQAPRLLIYD ASNRATGIPA RFSGSGSGTD FTLTISSLEP EDFAVYYCQQ RSKWPPTWTFGQ GTRVDIKR), SEQ ID NO.10 (SL301 VL: ELVLTQSPGT LSLSPGERAT LSCRASETVSS RQLAWYQQKP GQAPRLLIYG ASSRATGIPD RFSGSGSGTD FTLTISRLEP EDSAVFYCQQ YGSSPRTFGG GTKLEIKR), SEQ ID NO.11 (SL310 VL: ELVLTQSPGT LSLSPGERAT LSCRASQSVSS SSLAWYQQKP GQAPRLLIYG ASSRATGIPD RFSGSGSGTD FTLTISSLQP EDAATYYCQK YSSYPLTFGQ GTKLEIKR) and SEQ ID NO.12 (SL335 VL: ELVLTQSPGT LSLSPGETAT LSCRASQSVG SNLAWYQQKP GQAPRLLIYG ASTGATGVPA RFSGSRSGTD FTLTITSLQP EDFATYYCQQ YYSFLAKTFGQ GTQLEIKR). And the $V_H$ domain of the Fab above is bound to the heavy chain constant 1 domain ($C_{H1}$ domain), and VL domain of the Fab is bound to light chain constant domain ($C_{\kappa L}$ domain). Furthermore, the Fab specific for serum albumin (SA) of the present invention comprises the amino acid sequences of SEQ ID NO. 13 (CDR1)(AYSMN), 14 (CDR2) (SISSSGRYIHYADSVKG) and 15 (CDR3) (ETVMAGKALDY) in the VH region of SL335, and the amino acid sequence of SEQ ID NOS. 16 (CDR1)(RASQSVGSNLA), 17 (CDR2)(GASTGAT) and 18 (CDR3)(QQYYSFLAKT) in the VL region of SL335.

In one embodiment, the amino acid of cysteine of $C_{H1}$ domain and $C_{\kappa L}$ domain of the Fab might be deleted or substituted with serine residues. In particular, as for the SL335 above, the amino acid of cysteine of $CH_1$ domain is the $233^{th}$ amino acid starting from the N-terminus of the $C_{H1}$ domain, and the cysteine of $C_{\kappa L}$ domain is the $214^{th}$ amino acid starting from the N-terminus of the $C_{\kappa L}$ domain are substituted with serine residues. To avoid confusion, the H chains and the L chains that compose the Fab were named as follow: 1) Hcys: the H chain with cysteine at the $233^{th}$ position, 2) Lcys: the L chain with cysteine at the $214^{th}$ position, 3) Hser: the H chain with serine at the $233^{th}$ position, and 4) Lser: the L chain with serine at the $214^{th}$ position.

In another embodiment of the present invention, the Fab-effector fusion is constructed by linking the effector domain to the N- or C-terminus of either the Fd or light chain of a Fab molecule through genetic fusion. Since the folding and heterodimerization mechanisms of recombinant proteins in the periplasmic environment of *E. coli* are rather complicated and largely unknown, it is unpredictable which Fab-effector fusion format is optimal for a functional expression.

Further, in another embodiment, a fusion construct of an antigen binding fragment(Fab) and effector domain (a bioactive effector moiety) is provided, wherein the amino acid of Cysteine of $C_{H1}$ domain and the amino acid of Cysteine of $C_{\kappa L}$ domain of the Fab are deleted or substituted with serine residues; and wherein the bioactive effector moiety is a protein or a (poly)peptide; and wherein the Fab and the bioactive effector moiety are covalently linked by genetic fusion. The Fab and the bioactive effector moiety may be covalently linked by genetic fusion using a peptide linker of 0 to 20 amino acids. Among six Fab-effector fusion formats (or constructs) comprising hGH of the present invention, the results clearly demonstrated that HserG/Lser exhibited the highest expression yield in *E. coli*. That is, in accordance with this embodiment, the removal of both $Cys^{233}$ in the $C_{H1}$ domain and $Cys^{214}$ of in the $C_{Lk}$ either by deletion or substitution with other amino acid residue improves soluble expression of SL335-fusion effector constructs in the culture supernatant. This addresses three important issues. First, the fusion of an effector moiety, for example, hGH to the C-terminus of $C_{H1}$ is preferable to the C-terminus of $C_{Lk}$. Previously, Lu et al. had reported that the genetic linkage of the anti-Flt-1 scFv to the C-terminus of $C_{H1}$ of the anti-KDR Fab produced a five-fold higher yield than linkage to the C-terminal of $C_L$ domain (see Lu et al., (2002) *J Immunolog Meth.* 267, 213-226). Although the data were not included, we inventor's western blot analysis using total *E. coli* lysates revealed that the Fd fragments of LcysG/Hcys and LserG/Hcys were almost completely degraded, resulting in no detection of the soluble form of the fusion proteins in the *E. coli* supernatant. Because $V_H$ domains are prone to aggregate in *E. coli* (Dudgeon et al., (2009) *Protein Eng Des Sel.* 22, 217-220), it can be speculated that the presence of an effector domain at the C-terminal end of $C_L$ may restrain the interaction of a $V_H$ domain to a $V_L$ domain and a $_{CH1}$ domain to a $C_L$ domain, leading to rapid aggregation and degradation of Fd fragments. Comparing the soluble expression yields between LserG/Hcys and LserG/Hser, the presence of $Cys^{233}$ in the $C_{H1}$ domain seemed to accelerate this process probably due to aberrant disulfide bond formations. After removing $Cys^{233}$ in the $C_{H1}$ domain, the presence of an effector domain at the end of a $C_{H1}$ might have a beneficial effect on reducing $V_H$ domain aggregation by the partial blocking of hydrophobic surfaces on the $V_H$ domain before $V_H$-$V_L$ pairing. Second, the presence of the $Cys^{214}$ of $C_{Lk}$ further aggravates the soluble production of SL335-hGH fusion protein in an additive manner. Lower yield of HserG/Lcys than that of HserG/Lser could be explained by the tendency of L chains to form homodimers, known as Bence Jones proteins (see Kirsh et al., (2005) *J Immunol Methods.* 301, 173-185), in which the $Cys^{214}$ of $C_{Lk}$ may act on stabilization of homodimers, or is involved in forming aberrant disulfide bond(s) with other cysteine residues in the fusion protein. It has been also known that the disulfide bonds between the C-termini of $C_{H1}$ and $C_L$ in a Fab are highly mobile with a considerable degree of flexibility (see Rothlisberger et al., (2005) *J. Mol. Biol.* 347, 773-789; Humphreys et al., (2007) *Protein Eng Des Sel.* 20, 227-234). In this regard, the present invention provides an antigen-binding fragment (Fab) without the $Cys^{233}$ of heavy chain constant domain 1 ($C_{H1}$) and the $Cys^{214}$ of light chain constant domain ($C_{Lk}$). Likewise, HerGF/Lser and Hser-IFNb/Lser exhibited the highest expression yield in *E. coli*. In the fusion construct of the present invention, the molar ratio of the bioactive polypeptide (or protein) to the Fab is between 1:1 and 10:1, preferably between 1:1 and 4:1. Third, not only the expression yield but the accessibility of the anti-hGH antibody to the hGH domain is also restrained at some extend by the presence of these two C-terminal cysteine residues in SL335. This could be important for the therapeutic function of an effector domain in a Fab-effector fusion if the interaction between an effector domain and its ligand is also interfered. We inventors demonstrated that the utilization of $Fab_{Ads}$ as a fusion partner is beneficial not just for hGH, because other effectors such as G-CSF and IFN-b produced identical conclusions.

In another aspect of the present invention, an expression vector and the mutant *E. Coli* SUPEX5 strain (deposited in Korean Collection for Type Cultures with an address of 125 Gwahak-ro, Yuseong-gu, Daejeon 305-806, Republic of Korea under accession number of KCTC 12657BP on Aug. 20, 2014) as a host cell are provided to solve the technical problems. This strain was created by random chemical mutagenesis of MC1061 *E. coli* strain which was chosen because it derives from *E. coli* K12 stain, one of major host strain for producing commercial bio-pharmaceuticals. By comparing with the parental MC1061 strain, utilization of the mutant SUPEX5 *E. coli* strain as an expression host further implemented the beneficial effect on the production of HserG/Lser. Not only for SL335-hGH fusion, but the combination of Fab$_{ds}$ and SUPEX5 *E. coli* strain is also advantageous in soluble expression of a Fab-effector fusion protein in general, which was clearly demonstrated by the results obtained from SL335-GCSF fusions (SL335$_{wt}$-GCSF vs. SL335$_{Ads}$-GCSF), SL335-IFNβ fusions (SL335$_{wt}$-IFNb vs. SL335$_{Ads}$-IFNβ) EGL4-hGH fusions (EGL4$_{wt}$-hGH vs. EGL4$_{Ads}$-hGH), and 1β28-hGH fusions (1β28$_{wt}$-hGH vs. 1β28$_{Ads}$-hGH). Therefore, the results strongly support that the utilization of Fab$_{Ads}$, the mutant form of Fab without the Cys$^{233}$ of C$_{H1}$ and the Cys$^{214}$ of C$_{LK}$, is beneficial over a conventional Fab in the soluble expression of Fab-effector fusion proteins at least in SUPEX5 *E. coli* strain. The coexpression of chaperone proteins or disulfide isomerase (FkpA, SurA, Skp, Sec A, Sec B, DsbA or Dsb C) would improve the soluble and functional expression of SL335$_{wt}$-GCSF or even SL335$_{Ads}$-GCSF, since these fusions are known to increase the periplasmic production yield of soluble Fab fragments in *E. coli* (see Schlapschy et al., (2006) *Escherichia coli. Protein Eng Des Sel.* 19, 385-390). We inventors believe the utilization of Fab$_{ds}$ can be beneficial especially when chaperones and the catalytic machinery for disulfide formation in the endoplasmic reticulum are overloaded because of the high expression of Fab-effector fusion proteins in host cells.

In one embodiment of the present invention, SL335$_{Ads}$-hGH was produced at approximately 10 mg/L concentration using a culture flask, which is higher yield than the previous reports, despite of a 4-fold increase in molecular size in the present invention. According to the prior reports, studies on soluble expression of rhGH in the periplasm of *E. coli* showed that the yield was 0.64-2.57 mg/L for pelB-hGH and 0.32-2.29 mg/L for ompA-hGH (see Sockolosky and Szoka, (2013) *Protein Exp Purif.* 87, 129-135), while the yields of rhGH were largely dependent on the promoters and host *E. coli* strains that were used (see Soares et al., (2003) *Protein Engineering.* 16, 1131-1138). Through a simple medium optimization, we inventors routinely obtained the yield of ~50 mg/L in the culture supernatant using a culture flask that allows the cell density of OD$_{600nm}$=~10-11 (manuscript in preparation), which can be further improved enough for an industrial scale through the refined adjustment of medium compositions and a fed-batch culture system.

In another aspect of the present invention, SL335$_{ds}$-effector proteins shows increased affinity to HSA. In one embodiment, SL335$_{ds}$-hGH showed a five to nine-fold increase in response to HSA(Human Serum Albumin) and a 1.3 to 4-fold decrease in response to RSA(Rat Serum Albumin) depending on the pH condition compared to those of parent SL335. Genetic linking of an antibody fragment and an effector domain would affect an antigen-binding affinity of the antibody fragment, and the changes in affinity can be varied at large extent depending on the nature of an antibody fragment, an effector domain and how to link these two functional moieties. It is not clear whether these differences in affinity result from the absence of the interchain disulfide bond or the presence of the hGH fusion domain. Nonetheless, the effect of hGH fusion on the binding affinities of SL335$_{Ads}$ to the antigens seems negligible compared to that of IFN-a2b-DOM7 h-14, whose affinities to human, mouse and rat SA decreased 7.7, 22.3 and 15.8-fold relative to the parent DOM7 h-14 (see Walker et al., (2010) *Protein Eng Des Sel.* 23, 271-278). Therefore, Fab might have an advantage over domain Ab in maintaining the affinity and effector folding because the C$_{H1}$ and C$_L$ domains provide space for reducing steric hindrance between an antigen-binding region and an effector domain that binds to the respective ligands.

In another embodiment of the present invention, SL335$_{Ads}$-hGH profoundly extended the serum half-life in that its t$_{1/2}$ (16.6 h in intravenous administration) was similar to that of PEGS-hGH (250 kDa) (see Clark et al., 1996). Interestingly, the t$_{1/2}$ of SL335$_{Ads}$-hGH was 5.6-fold longer than that of Albutropin® (t$_{1/2}$=2.96 h), and the difference in the t$_{1/2}$ between SL335$_{Ads}$-hGH and Albutropin® was further extended in the S.C. (subcutaneous) administration up to 16-fold (97.2 h vs. 5.93 h) (see Osborn et al., 2002), although these comparisons are circumstantial unless the experiments are performed under the same settings. Similarly, the t$_{1/2}$ of IFN-a2b-DOM7 h-14 was also approximately 1.5 times longer than that of HSA-IFN-a2b (see Walker et al., 2010). Therefore, it seems likely that the fusion of an albumin-binder provides a longer half-life than the fusion with albumin, and the underlying mechanisms are yet to be determined. It is noteworthy that the serum t$_{1/2}$ of SL335$_{Ads}$-hGH in I.V. administration was similar to that of VRS-317 (t$_{1/2}$=15 h) (Cleland et al., (2012) *J Pharm Sci.* 101, 27442754). This may suggest that longer than once-weekly or even once a month dosing could be possible for SL335$_{Ads}$-hGH (termed SAFAtropin®).

In another embodiment of the present invention, the pharmacodynamic effects of SL335$_{Ads}$-hGH seemed far superior to those of Albutropin®, and 7-fold more potent than Growtropin® at molar basis considering the once-weekly dosage regimen. Unfortunately, we had to discontinue a 2-week pharmacodynamic study at Day 11 because some of the hypophysectormized rats, especially those belonging to the Excipient Only group, died early. It seemed likely that the animals were severely stressed by the long-distance transportation from Japan to South Korea after surgery during August, which manifested by 5% weight loss of those belonging to the Excipient Only group and the bigger standard deviation values than we anticipated. Nonetheless, it seems clear that SL335$_{Ads}$-hGH has a huge potential being developed as a long-acting hGH, and, therefore, we referred it to SAFAtropin® now on.

In another embodiment of the present invention, the bioactive polypeptide fused to the Fab above is anyone selected from the group consisting of hormone, cytokine, enzyme, antibody, growth factor, transcription factor, blood factor, vaccine, structure protein, ligand protein, and receptor.

In yet another embodiment of the present invention, the bioactive polypeptide is anyone selected from the group consisting of human growth hormone, growth hormone releasing hormone (GHRH), growth hormone releasing peptide, interferons, interferon receptors, colony stimulating factors (CSFs), glucagon-like peptides, G-protein-coupled receptor, interleukins, interleukin receptors, enzymes, interleukin binding proteins, cytokine binding proteins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, virus derived vaccine antigens, monoclonal antibodies, polyclonal antibodies, and antibody fragments.

In another aspect of the present invention, a pharmaceutical composition is provided, wherein the composition comprises the Fab-effector moieties fusion constructs of the present invention and pharmaceutically acceptable excipient, and has increased in vivo sustainability. The pharmaceutical composition of the president invention can be administered into a body through various ways including oral, transcutaneous, subcutaneous, intravenous, or intramuscular administration, and more preferably can be administered as an injection type preparation. Further, the pharmaceutical composition of the present invention can be formulated using the method well known to the skilled in the art to provide rapid, sustained or delayed release of the active ingredient following the administration thereof. The formulations may be in the form of a tablet, pill, powder, sachet, elixir, suspension, emulsion, solution, syrup, aerosol, soft and hard gelatin capsule, sterile injectable solution, sterile packaged powder and the like. Examples of suitable carriers, excipients, and diluents are lactose, dextrose, sucrose, mannitol, xylitol, erythritol, maltitol, starches, gum acacia, alginates, gelatin, calcium phosphate, calcium silicate, cellulose, methyl cellulose, microcrystalline cellulose, polyvinyl pyrrolidone, water, methylhydroxybenzoates, propylhydroxybenzoates, talc, magnesium stearate and mineral oil. Further, the formulations may additionally include fillers, anti-agglutinating agents, lubricating agents, wetting agents, favoring agents, emulsifiers, preservatives and the like.

It should be be understood that the amount of the fusion protein or polypeptide actually administered ought to be determined in light of various relevant factors including the condition to be treated, the selected route of administration, the age, sex and body weight of the individual patient, and the severity of the patients symptom; and the type of bioactive polypeptide of active ingredient. Since the fusion protein of the present invention has very excellent sustainability in blood, the number and frequency of administration of the peptide preparations comprising the fusion protein of the present invention can be reduced significantly.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

In the present invention, the "bioactive polypeptide or protein" is the (poly)peptide or protein representing useful biological activity when it is administered into a mammal including human.

In the present invention, the "Fab-effector moietie(s) fusion construct(or format)" is the construct wherein a bioactive (poly)peptide or protein covalently bonded to the Fab. Further, "Fag-effector moietie(s) fusion construct (or format)" is understood to include Fab-fusion protein, Fab-fusion (poly)peptide, fusion constructs, and fusion formats.

In this regard, the present invention is described in detail in examples. It should be noted that the description of the examples does not limit the scope of the invention as described in the preceding disclosure.

In the present invention, an anti-Serum Albumin $Fab_{Ads}$-Associated (SAFA) technology is provided as a novel platform technology for developing long-acting biotherapeutics. In this regard, the present invention has advantages over other conventional technologies including PEGylation, Fc-fusion, AlbudAb technology and albumin-fusions in terms of long acting in vivo, maintaining the conformation of an effector domain, binding affinities, and simple production and procedures with low costs.

BRIEF DESCRIPTION OF DRAWINGS

FIG. 4 is a diagram depicting six SL335-hGH fusion formats constructed in this study.

FIG. 5A shows the concentration of soluble SL335-hGH fusions that was measured by sandwich ELISA using the mouse anti-human Fd mAb as a capturing Ab and the goat anti-human kappa L chain pAb conjugated with HRPO as a detecting antibody; FIG. 5B shows the binding reactivity of SL335-hGH fusions to HSA; FIG. 5C the binding reactivity of SL335-hGH fusions to T-20; and FIG. 5D shows the binding reactivity of SL335-hGH fusions to NYThGH.

(FIG. 6A); 25° C. (FIG. 6 B); or 30° C. (FIG. 6C).

FIGS. 9A through 9C represent the Analyses of $SL335_{wt}$-hGH and $SL335_{ds}$-hGH by SDS-PAGE and western blot. FIG. 9A shows the results of Coomassie Blue staining; FIG. 9B shows the western blot results by the goat anti-human kappa L Ab-conjugated with AP to detect Lcys and Lser; and FIG. 9C show the western blot results by T-20 anti-hGH pAb.

FIG. 12A shows the FPLC results where arrows indicate the fractions chosen for SDS-PAGE analysis and FIG. 12B shows the SDS-PAGE results of these fractions.

Figure 19:
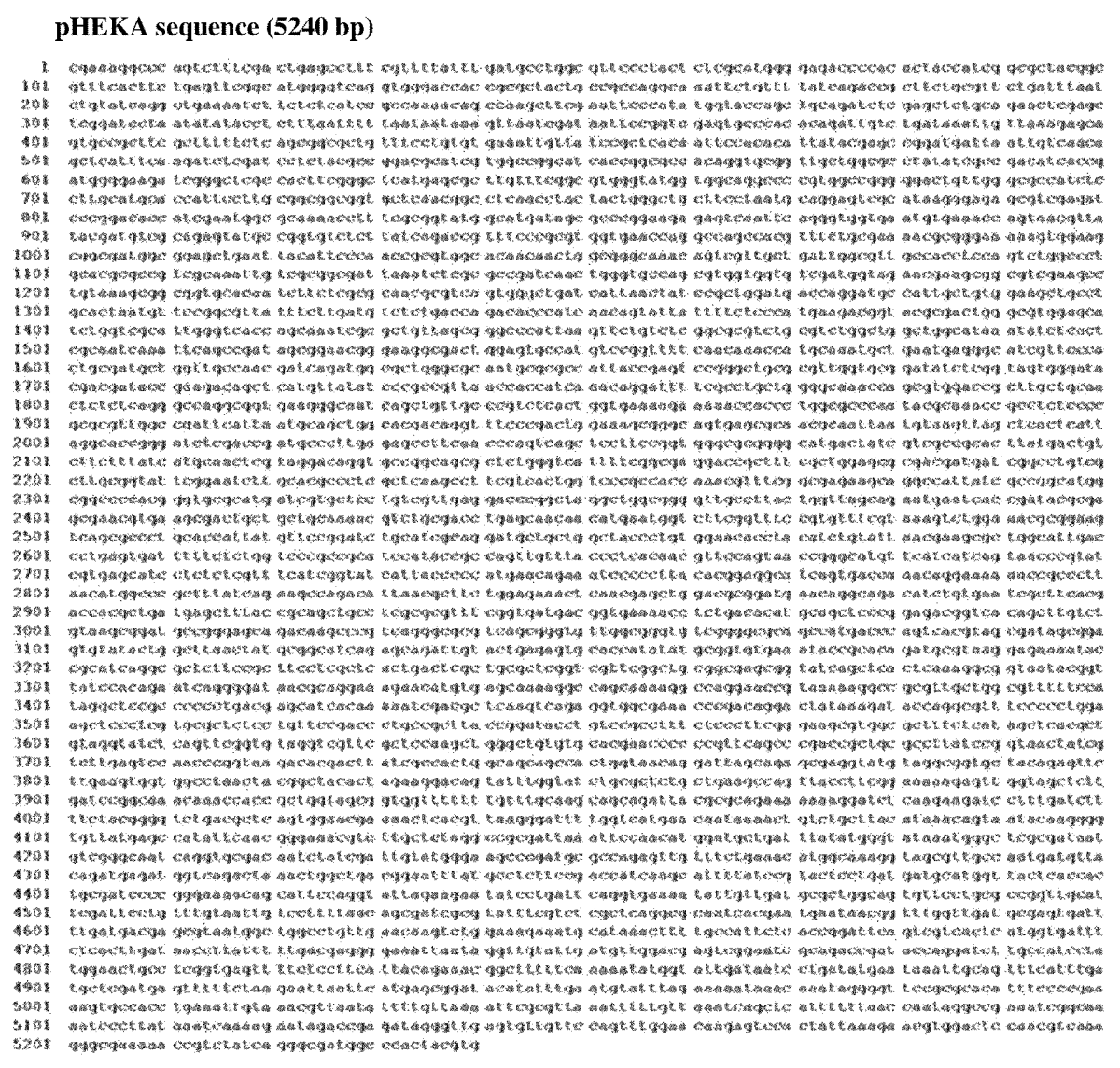

FIG. 19 shows the nucleic acid sequence of the pHEKA vector (SEQ ID NO: 110) of the present invention.

Figure 21A:
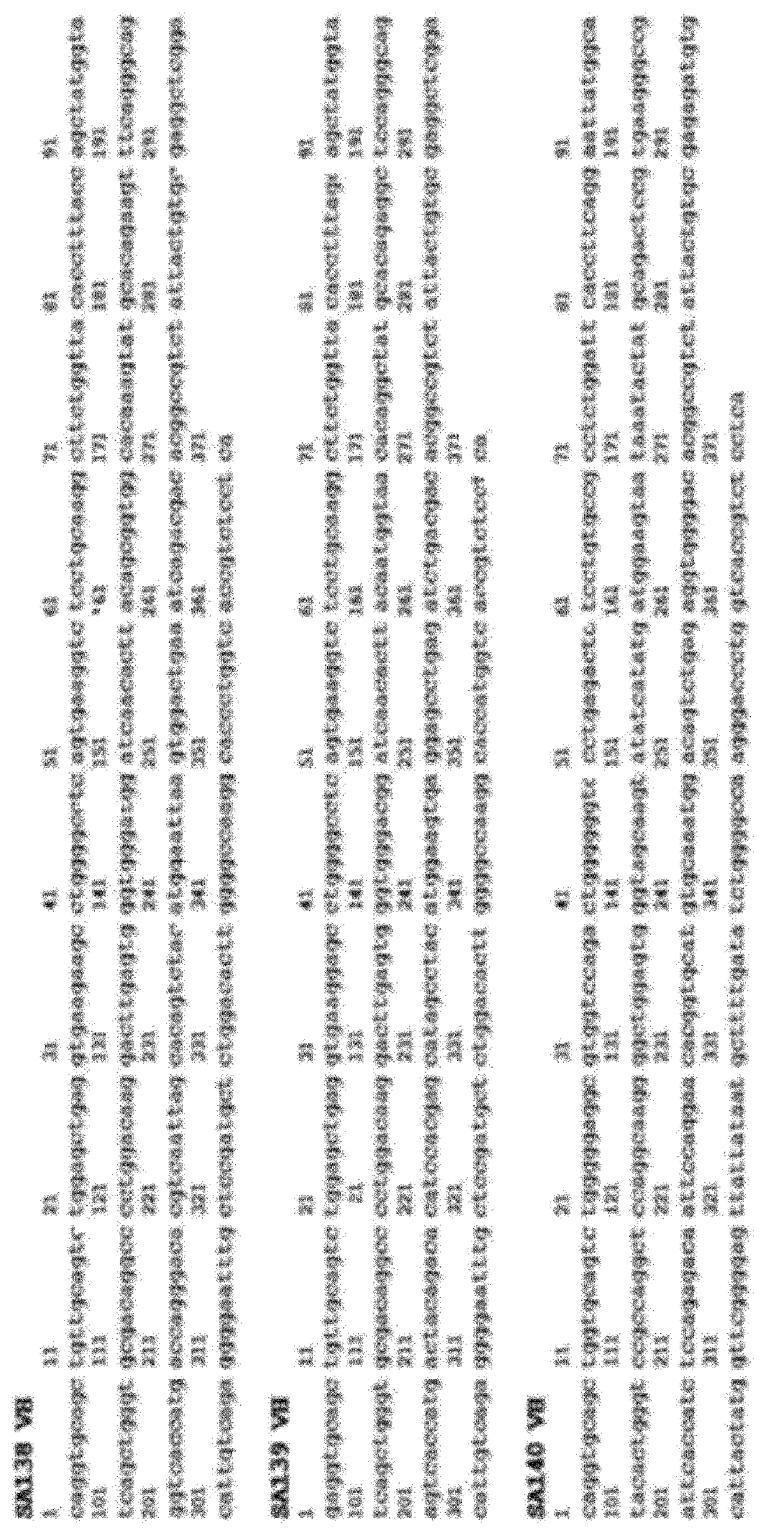
Figure 21B:
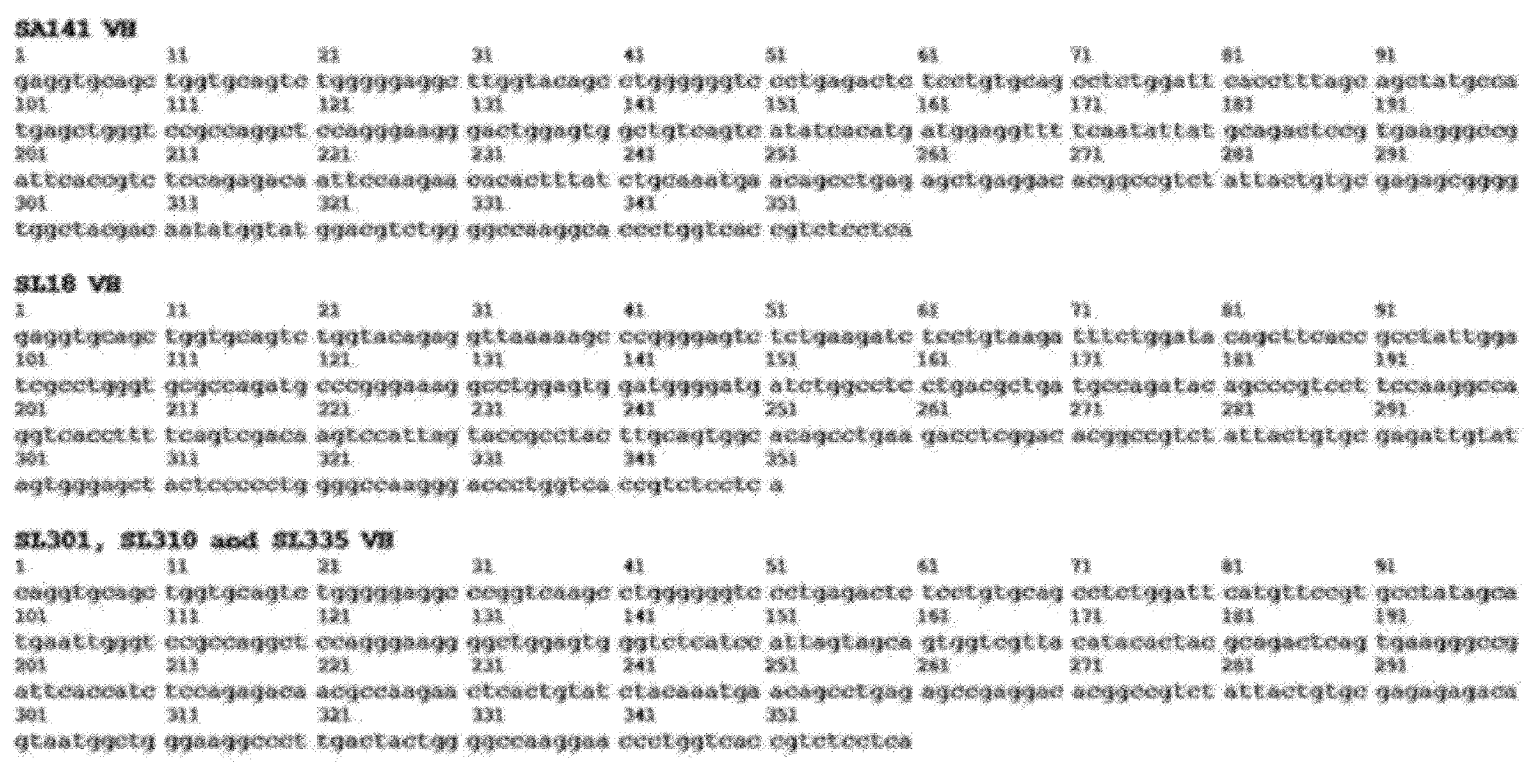
Figure 21C:
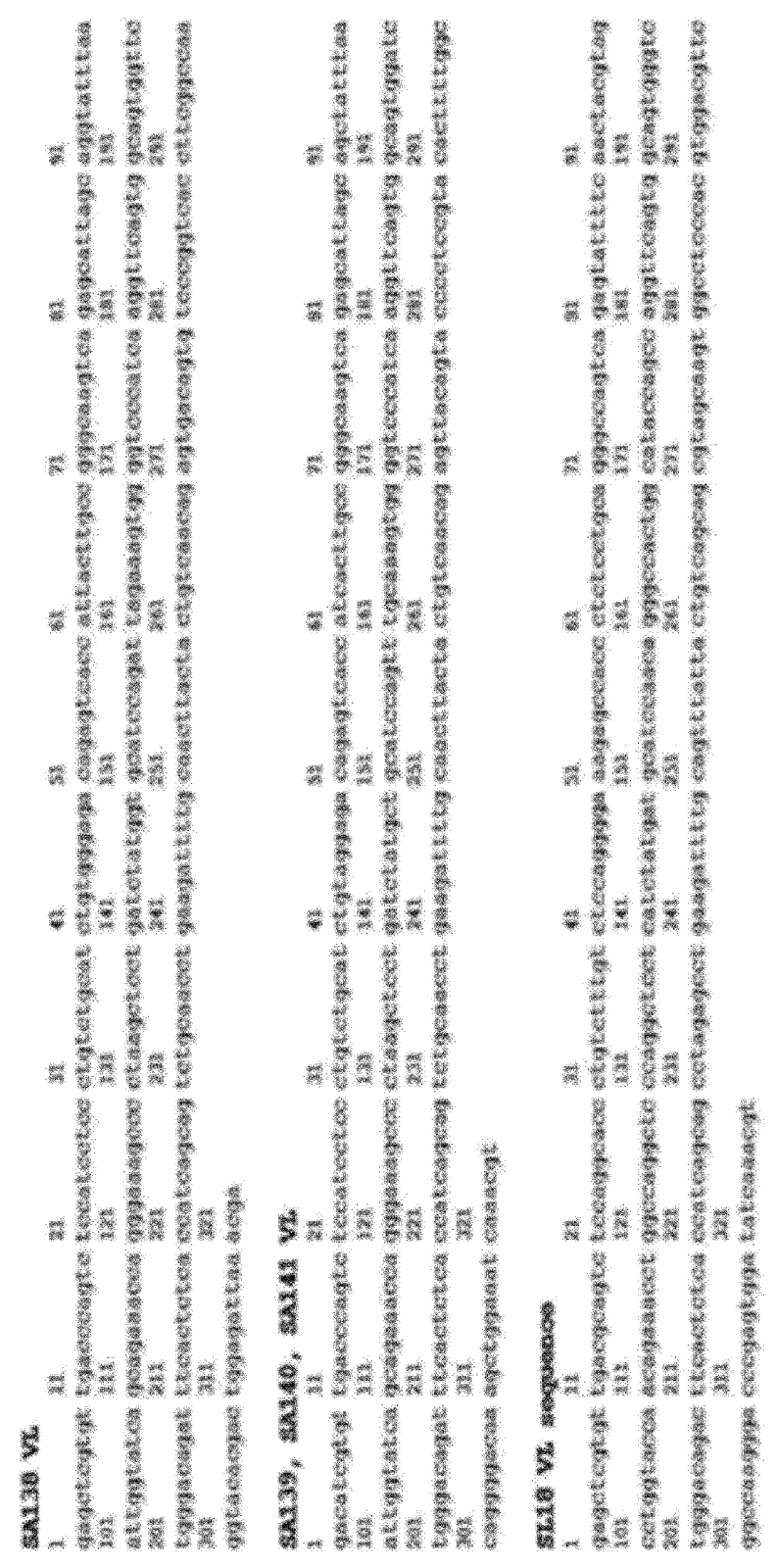
Figure 21D:
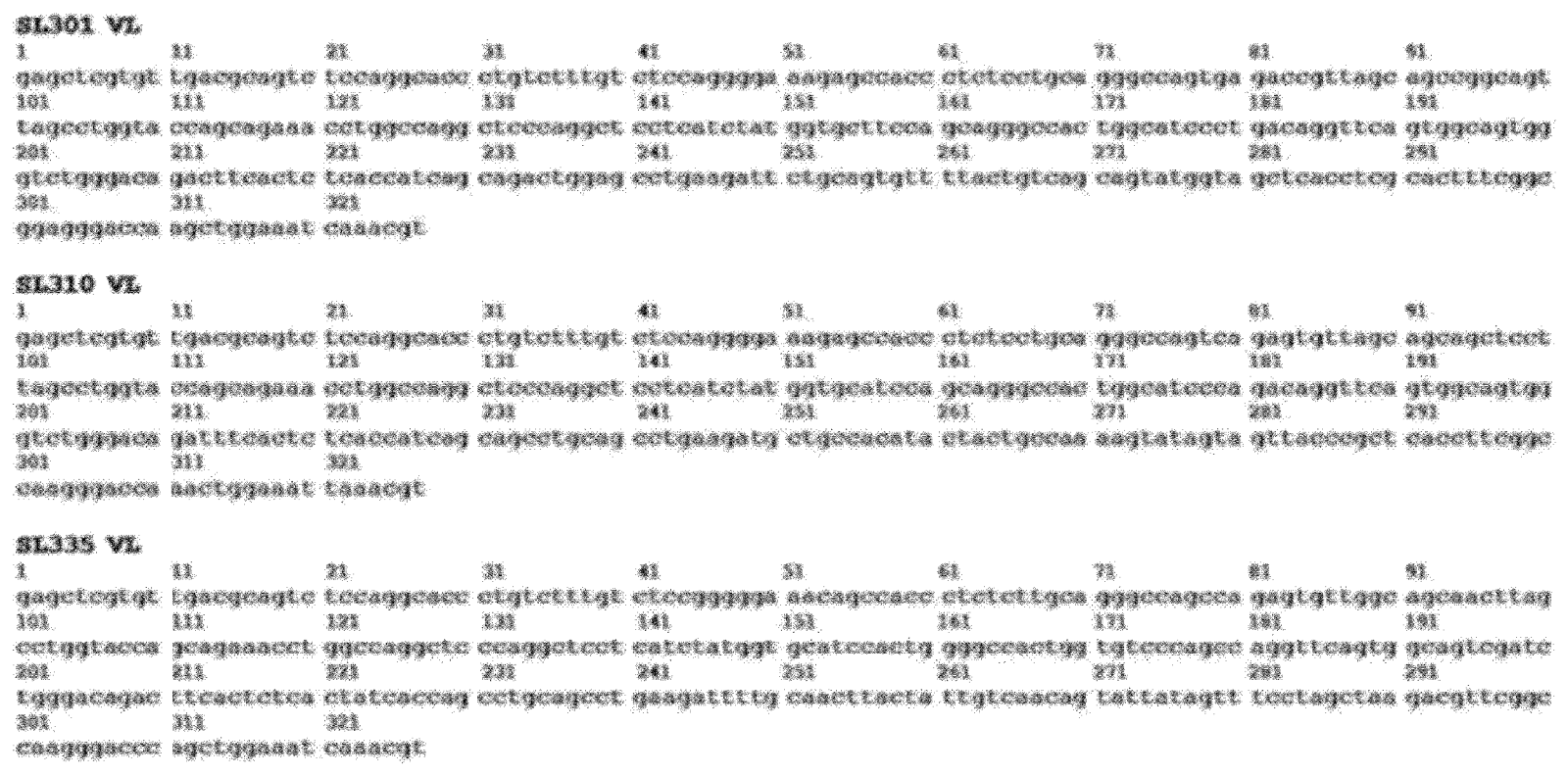

FIGS. 21A through 21D show the DNA sequence of the VH (FIG. 21A and FIG. 21B) and the VL genes (FIG. 21C and FIG. 21D) utilized by the anti-SA Fab clones of the present invention: SA138 VH (SEQ ID NO: 98); SA139 VH (SEQ ID NO: 99); SA140 VH (SEQ ID NO: 100); SA141 VH (SEQ ID NO: 101); SL18 VH (SEQ ID NO: 102); SL301, SL310 and SL335 VH (SEQ ID NO: 103); SA138 VL (SEQ ID NO: 104); SA139, SA140, SA141 VL (SEQ ID NO: 105); SL18 VL (SEQ ID NO: 106); SL301 VL (SEQ ID NO: 107); SL310 VL (SEQ ID NO: 108); and SL335 VL (SEQ ID NO: 109).

FIGS. 22A through 22J show the sequence information of the Fab-effector fusion constructs of the present invention. The linker and the effector domains were underlined and CDRs were written in bold. FIG. 22A shows SL335$_{wt}$-hGH (SEQ ID Nos: 58-61, top to bottom); FIG. 22B shows SL335$_{Ads}$-hGH (SEQ ID Nos: 62-65, top to bottom); FIG. 22C shows SL335$_{wt}$-GCSF (SEQ ID Nos: 66-69, top to bottom); FIG. 22D shows SL335$_{Ads}$-GCSF (SEQ ID Nos: 70-73, top to bottom); FIG. 22E shows SL335$_{wt}$-IFNβ (SEQ ID Nos: 74-77, top to bottom); FIG. 22F shows SL335$_{Ads}$-IFNβ (SEQ ID Nos: 78-81, top to bottom); FIG. 22G shows EGL4$_{wt}$-hGH (SEQ ID Nos: 82-85, top to bottom); FIG. 22H shows EGL4$_{Ads}$-hGH (SEQ ID Nos: 86-89, top to bottom); FIG. 22I shows 1β28$_{wt}$-hGH (SEQ ID Nos: 90-93, top to bottom); and FIG. 22J shows 1β28$_{Ads}$-hGH (SEQ ID Nos: 94-97, top to bottom).

DETAILED DESCRIPTION

Figure 1A:
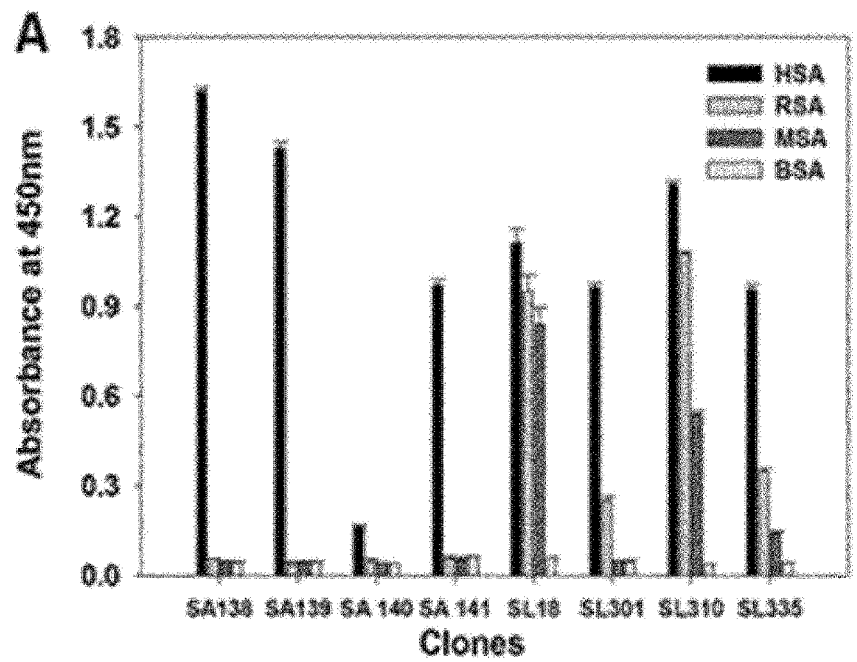
FIGS. 1A and 1B show the results of monoclonal phage ELISA to determine the binding specificity of anti-SA Fab phage antibodies under pH 6 (FIG. 1A) or pH 7.4 (FIG. 1B) conditions.

1. Materials and Analysis 1-(1) Cloning and Strains

All of the DNA cloning experiments were performed according to standard procedure (See Sambrook et al., (1989) Molecular cloning: A laboratory manula, 2nd ed., (New Youk, USA: Cold Spring Harbor Laboratory Press)). The oligonucleotides of sequencing grade and the codon-optimized genes for constructing SL335-effector fusion constructs were synthesized by Bioneer, Daej eon, South Korea. PCR amplification was performed using Pyrobest or Ex-Taq DNA polymerase (Takara, tsu, Japan) under the condition of 25 cycles at 94° C. for 1 min, 58° C. for 1 min and 72° C. for 1 min, followed by 72° C. for 10 min unless otherwise noted. The restriction endonucleases, shrimp alkaline phosphatase (SIP) and T4 DNA ligase were also purchased from Takara. The E. coli MC1061 strain [araD139 Del(araA-leu) 7697 Del(lac)X74 galK16 ga/E15(GalS) lambda-e14- mcrA0 relA1 rpsL150(strR) spoT1 mcrB1 hsdR2] (ATCC, Manassas, USA) was used for cloning and the E. coli SUPEX5 strain was used for recombinant protein expression. The E. coli TG1 strain {F' [traD36 proAB⁺ lacI$^q$lacZΔM15]supE thi-1 Δ(lac-proAB) Δ(mcrB-hsdSM)5, ($r_K^-m_K^-$)}(Agilent Technologies, Palo Alto, USA) was used for recombinant phage preparations.

1-(2) Biopanning of the HuDVFab-8L Antibody Library

An enrichment of recombinant phages bound to target antigens was performed as previously described (see Joo et al., (2008) J. Immunol. Methods. 333, 24-37; Hur et al., (2010) Immunol Lett. 132, 24-30). Briefly, tosylated magnetic beads conjugated with human, rat or mouse serum albumin (HSA, RSA or MSA, respectively) (Sigma-Aldrich, St. Louis, Mo., USA) were mixed with $10^{10}$ phages from the HuDVFab-8L antibody library (AprilBio, Chuncheon, South Korea) for 4 h at 4° C., and washed three times with phosphate-buffered saline containing 0.02% Tween (PBST). The phage antibodies that were bound to the beads were eluted with elution buffer (0.1 M glycine, pH 2). Fresh TG1 cells carrying the corresponding light (L) ($V_L+C_{Lk}$) chains were infected with eluted phages, and grown in 2 YT medium containing 25 μg/ml ampicillin, 10 μg/ml carbenicillin and 10 μg/ml tetracycline (2× YT/ACT). The recombinant phages were then amplified using Ex-12 helper phage (AprilBio) for subsequent panning. After the final panning, a monoclonal phage ELISA was performed to identify the positive clones. The Fd ($V_H+C_{H1}$) genes from the positive clones were subcloned into the pHg3A-3 vector (AprilBio, Chuncheon, South Korea), and L chain optimization was performed using 1.4·10⁸humannave kL chain repertoire in pLf1T-3 phagemid vector(AprilBio).

1-(3)-DNA Sequencing Analysis

The pHflg3A-2 (AprilBio) phagemid and pLf1A-3 plasmid (AprilBio) were isolated from E. coli cells producing anti-SA Fab molecules using the Wizard Plasmid Miniprep Kit (Promega, Medison, Wis., USA). Two different sequencing primers (5'-gtgccgttctatagccatagcac-3' (SEQ ID NO:19) and 5'-ggcactggctggtttcgctaccgtg-3'(SEQ ID NO:20)) that were complementary to pHflg3A-2 or pLT-2 were used to read the $V_H$ and $V_L$ genes, respectively. The DNA sequencing was performed by SolGent, Daej eon, South Korea.

1-(4) Construction of the pHEKA Expression Vector

Figure 18:
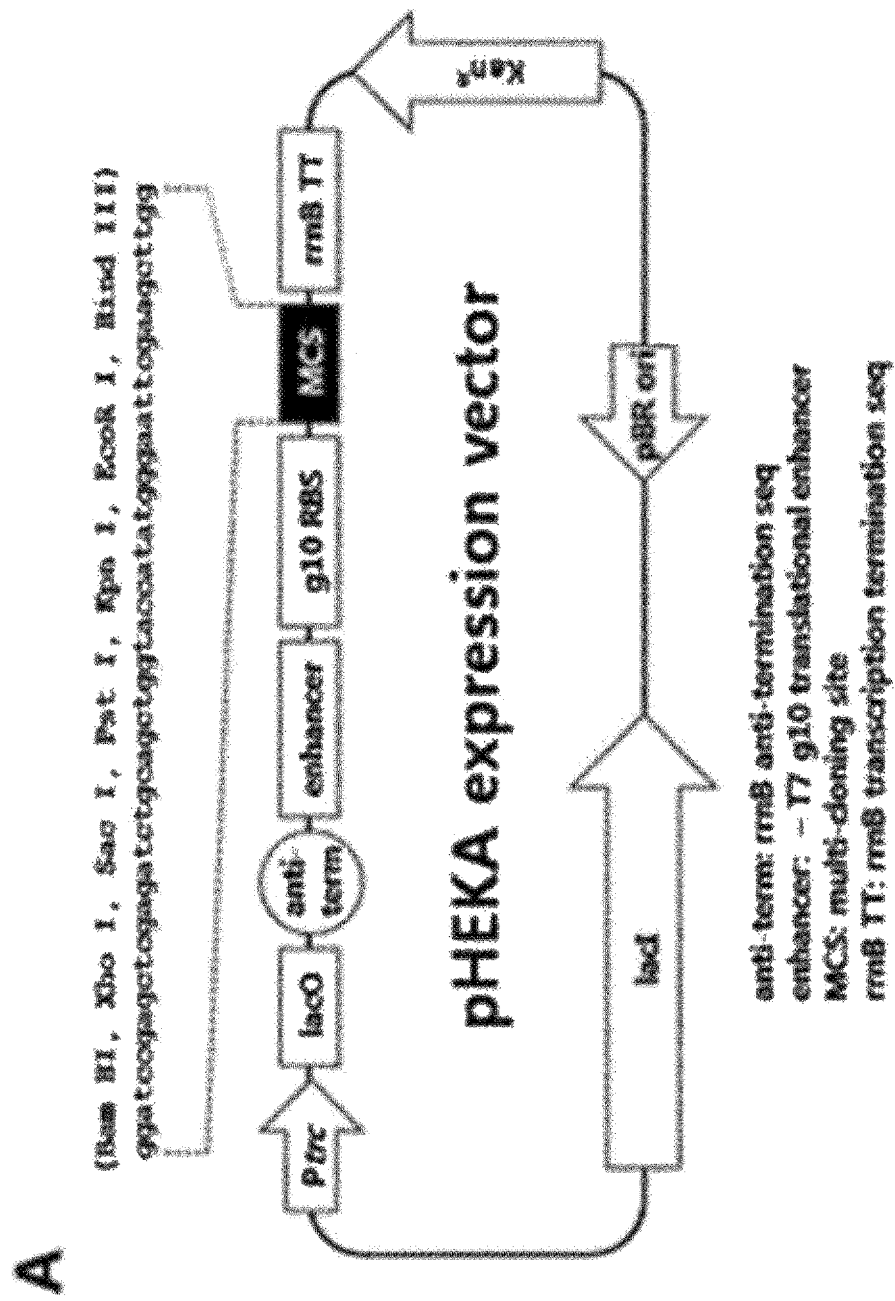
FIG. 18 depicts the pHEKA vector of the present invention.
Figure 20:
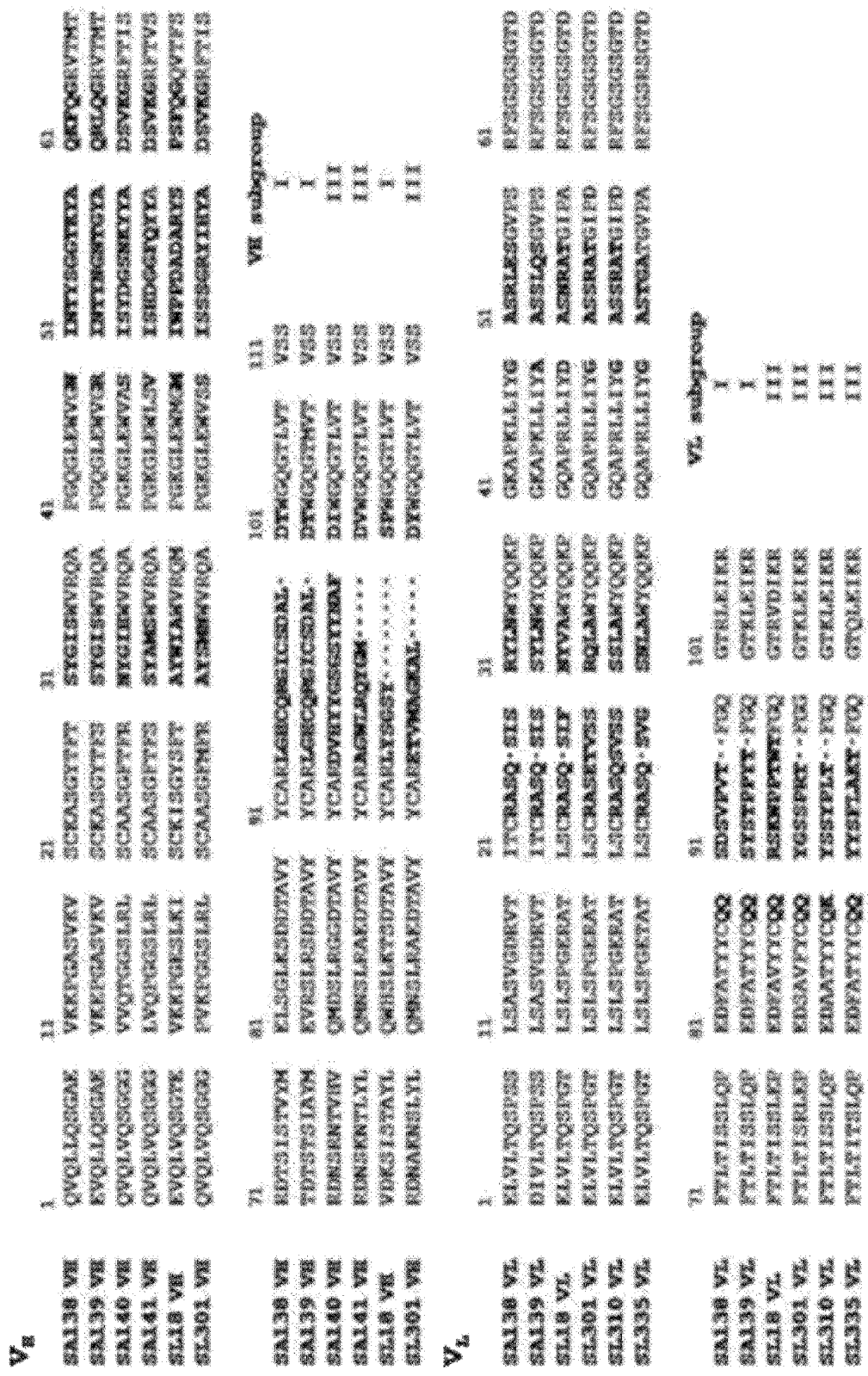
FIG. 20 shows the deduced amino acid sequence of the VH and the VLgenes utilized by the anti-SA Fab clones of the present invention: SA138 VH (SEQ ID NO: 1); SA139 VH (SEQ ID NO: 2); SA140 VH (SEQ ID NO: 3); SA141 VH (SEQ ID NO: 4); SL18 VH (SEQ ID NO: 5); SL301 VH (SEQ ID NO: 6); SA138 VL (SEQ ID NO: 7); SA139 VL (SEQ ID NO: 8); SL18 VL (SEQ ID NO: 9); SL301 VL (SEQ ID NO: 10); SL310 VL (SEQ ID NO: 11); and SL335 VL (SEQ ID NO: 12).

The DNA fragment #1 containing a Bgl II restriction site+trc promoter+g10 translation enhancer-ribosome binding site (RBS) was obtained by PCR amplification from the pTrcHis-B vector (Invitrogen, Carlsbad, Calif., USA) using Pyrobest DNA polymerase and a set of the PCR primer #1 (5'-gggagatcttgaaatgagctgttgacaattaatcatccg-3' (SEQ ID NO: 21)) and #2 (5'-cctctttaattttaataataaagttaatcgataattcc-3' (SEQ ID NO: 22)). The DNA fragment #2 containing a g10 translation enhancer+RBS+BamH I+multi-cloning site (MCS)+transcription terminator was obtained by PCR amplification from the same template as above using the PCR primer #3 (5'-ggaattatcgattaacthattattaaaaattaaagagg-tatatattaggatccgagctcgagttctgca-3' (SEQ ID NO: 23)) and #4 (5'-gggcactacgtgcgaaaggcccagtctttcgact-3' (SEQ ID NO: 24)). A linking PCR was performed to assemble these two DNA fragments using Ex-Taq DNA polymerase and a set of the PCR #1 and #4 primers. The resulting ~520 bp DNA fragment was isolated through agarose gel electrophoresis. Thereafter, the linking PCR product and the pET28a (Invitrogen) plasmid were restricted with Bgl II and Dra III and ligated together using T4 DNA ligase 2 h at RT. After transforming MC1061 electrocompetent cells with 3 ml of the ligation reaction, the E. coli transformants were selected on 2 YT plates containing 50 µg/ml of kanamycin (Sigma-Aldrich). For subcloning Fab genes into the pHEKA vector, the Fd ($V_H+C_{H1}$) chain genes were PCR amplified from the pHflg3A-2 phagemid vector using a set of PCR primer #5 (5'-ggccgcagatctgttaattaaggaggaatttaaagaattcatgaaaaaactgct-gacgcgattccgct-3' (SEQ ID NO: 25)) and #6 (5'-gggaagctt-attaacaagatttgggctcaactctcttgtcc-3' (SEQ ID NO: 26)), and the L chain genes were PCR amplified from the pLT-2 plasmid vector using a set of PCR primer #7 (5'-gggggatc-catgaaaaagacagctatcgcgattgcagtg-3' (SEQ ID NO: 27)) and #8 (5'-attcctccttaattaacagatctgcggccgcactcgagattaacactctc-ccctgagaagctattgt-3' (SEQ ID NO: 28)). The resulting Fd and L chain gene fragments were assembled through linking PCR using the PCR #6 and #7 primers, and the resulting PCR product of ~1.4 kbp in size was excised from the agarose gel. Thereafter, the PCR product and the pHEKA plasmid were restricted with BamH I and Hind III, ligated together using T4 DNA ligase for 2 h at RT, and electroporated into E. coli MC1061 or SUPEX5 electrocompetent cells. The PCR primers used in preparing pHEKA expression vector is shown in Table 1 below. And FIG. 18 shows a diagram of pHEKA expression vector.

TABLE 1

PCR primers preparing pHEKA expression vector

| Constructs | Primers | Oligonucleotide sequence |
|---|---|---|
| pHEKA | Primer 1 | 5'- gggagatcttgaaatgagctgttgacaattaatcatccg-3' (SEQ ID No: 21) |
| | Primer 2 | 5' - cctctttaattttaataataaagttaatcgataattcc-3' (SEQ ID No: 22) |
| | Primer 3 | 5' - ggaattatcgattaactttattattaaaaattaaagaggtatatattaggatccgagctcgagttctgca-3' (SEQ ID No: 23) |
| | Primer 4 | 5' - gggcactacgtgcgaaaggcccagtctttcgact-3' (SEQ ID No: 24) |
| | Primer 5 | 5' - ggccgcagatctgttaattaaggaggaatttaaagaattcatgaaaaaactgctgttcgcgattccgct-3' (SEQ ID No: 25) |
| | Primer 6 | 5' - gggaagcttattaacaagatttgggctcaactctcttgtcc-3' (SEQ ID No: 26) |
| | Primer 7 | 5' - gggggatccatgaaaaagacagctatcgcgattgcagtg-3' (SEQ ID No: 27) |
| | Primer 8 | 5' - attcctccttaattaacagatctgcggccgcactcgagattaacactctcccctgttgaagctctagt-3' (SEQ ID No: 28) |

1-(5)-Establishment of the Mutant E. Coli SUPEX5 Strain

Chemical mutagenesis was carried out essentially as described in previous work. Briefly, E. coli MC1061 cells expressing the anti-human branched chain keto acid dehydrogenase complex-E2(BCKD-E2) scFv fused with alkaline phosphatse(AP) were grown in Luria Broth (LB) medium containing 50 µg/ml of ampicilin to an $OD_{600}$ of ~0.3. The cells contained in 5 ml of culture were collected by centrifugation at 3,000 g for 10 min, washed twice with cold 0.1 M sodium citrate buffer (pH 5.5). The cells were then resuspended in 1.9 ml of the same buffer, and treated with 50 µg/ml of N-methyl-N'-nitro-N-nitrosoguanidine(MNNG) (Sigma-Adrich,St. Louis, Mo., USA) at 37° C. for 15, 30 and 45 min. After MNNG treatment, the cells were mixed, washed twice and resuspended in 2 ml of LB medium. Colony lift assay with a two-membrane system was then performed as described. Briefly, LB agar plates containing 50 µg/ml ampicillin and 10 µg/ml carbenicillin were covered with the first nylon membranes (0.45 m Nytran N Nylon blotting membrane) (GE Healthcare Life Science, Wauwatosa, Wis., USA) of low protein binding capacity. The mutated bacteria were spread on the membranes at the density of a $10^6$ cells/plate and grown for 8 h at 37° C. Meanwhile, the second nitrocellulose membranes (Bio-Trace™ NT Nitrocellulose Transfer Membrane) (PALL, Port Washington, N.Y., USA) were laid over fresh LB agar plates containing 50 µg/ml ampicillin, 10 µg/ml carbenicillin and 1 mM isopropyl-D-1-thiogalactopyranoside (IPTG) (Sigma-Aldrich). The first nylon membranes were removed from the LB agar plated and placed on top of the second membranes, followed by incubation 37° C. for 5 h. After incubation, the first membrane (with colonies) was removed, placed onto fresh LB agar plates containing 50 µg/ml ampicillin and 10 µg/ml carbenicillin, and stored at 4° C. for later recovery of the bacteria. The second membranes were washed three times for 10 min in fresh phosphate-buffered saline containing 0.1% v/v Tween 20 (PBS/Tween), and immersed into the nitro blue tetrazolium chloride (NBT)/5-bromo-4-chloro-3-indolyl phosphate (BCIP) substrate (Duchefa, Haarelem, Netherlands) to visualize the AP of *E. coli* colonies. The *E. coli* colonies showing a distinctive AP activity were picked from the corresponding first filters, pooled together, and the second round of mutagenesis and colony lift assay were performed. After the second round of colony lift assay, the tentative positive *E. coli* clones were selected, and grown in 10 ml 2 YT medium containing 50 µg/ml ampicillin and 10 µg/ml carbenicillin until $OD_{600}$ reaches 0.5. IPTG was added into the culture at 0.1 mM final concentration, and the cells were grown over night at 27° C. The culture supernatant was then harvested by centrifugation at 3,300 g for 20 min. For preparing periplasmic extracts, the cell pellet was resuspended in the periplasmic extraction buffer (2 stock; 200 mM Tris-HCl, 20 mM EDTA, 2 M NaCl, pH 7.4), frozen and thawed three times, and centrifuged at 10,000 g for 20 min at 4° C. The periplasmic extract containing soluble anti-BCKD-AP fusion was finally obtained by harvesting the supernatant. Serial dilutions of the culture supernatant and the periplasmic extract were prepared by using PBS containing 1% bovine serum albumin (BSA) (Sigma-Aldrich), and 50 ml of the culture supernatant or the periplasmic extract samples were mixed with 100 ml of a p-nitrophenyl phosphate (pNPP) substrate (Roche, South Sna Francisco, Calif., USA) in a 96-well microtiter plate (SPL, South Korea). After 5-10 min, 25 µl of 3 M NaOH was added into each well the stop the reaction, and the absorbance at 415 nm was measured suing an ELISA reader (Bio-Rad, Hercules, Calif., USA). Four mutant *E. coli* strains (M #5, M #7, M #54 and M #69) showing the enhanced expression of the anti-BCKD-AP fusion were grown in 2 YT medium without antibiotics at 37° C. overnight. The cells were then spread onto LB agar plates at a ~$10^3$ cells/plate density, and grown at 37° C. overnight. The resulting colonies were replicated onto LB agar plates with or without 50 µg/ml ampicillin. The *E. coli* colonies grown in the LB agar plates without antibiotics but failed to grow in the LB agar plates with antibiotics were selected, and grown in 2 YT medium without antibiotics until $OD_{600}$ reaches ~1.0. The cell stocks were prepared by adding glycerol (20% v/v), and stored at 80° C. Forbeing used for cloning, the electro competent cells were prepared from the mutant strains according to a standard protocol, and stored at 80° C. M #5, one of the mutant *E. coli* strains, was named as SUPEX5 (KCTC 12657BP), and used for expressing Fab and Fab-effector fusion proteins.

1-(6)-Enzyme-Linked Immunosorbent Assay(ELISA)

For the monoclonal phage ELISA, the recombinant phage was obtained from positive *E. coli* clones by phage rescue, and ~$10^8$ CFU/well were added to MaxiSorb ELISA plates (Nunc, Roskilde, Denmark) that were coated with 5 µg/ml HSA, RSA, MSA or BSA. The phage was allowed to bind to the antigens either at pH 6 or at pH 7.4 for 1 h at 37° C. A goat anti-human kappa L Ab-conjugated with HRPO (Sigma-Aldrich) was used as a secondary antibody. The binding signals were visualized with a TMB substrate (BD Science, San Jose, Calif., USA), and the absorbance at 450 nm was measured using an ELISA reader (Bio-Rad, Hercules, Calif., USA). The data represent the average of three experiments standard deviation. For the conventional ELISA, the various antigens [human SA, rat SA, mouse SA, monkey SA (Alpha diagnositic Intl., San Antonio, Tex., USA), canine SA (CUSABIO, Wuhan, Hubei, China). rabbit SA (Sigma-Aldrich), epidermal growth factor receptor (EGFR) (R&D systems, Minneapolis, Minn., USA), epithelial cell adhesion molecule (EpCAM) (R&D systems), IL-15 receptor a (IL-15Ra) (R&D systems), IL-10 (eBioscience, San Diego, Calif., USA), CD16a (R&D systems), c-MET (Sinobiological, Beijing, China)] at 5 µg/ml concentrations were immobilized on the microtiter plates, and the Fab molecules were allowed to bind to the antigens, and detected as above. To determine the concentration of soluble Fab or Fab-hGH fusion proteins, a sandwich ELISA was performed using a mouse anti-human IgG Fd mAb (AprilBio) as a capturing Ab and the goat anti-human kappa L chain pAb-HRPO conjugated (Sigma-Aldrich) as a detecting antibody. The human Fab fragment (Bethyl, Montgomery, Tex., USA) with a known concentration was used to draw the standard curve. For detecting the hGH domain, T-20, a goat pAb specific for the C-terminus of the hGH (Santacruz Biotechnology, Dallas, Tex., USA) and NYThGH, a mouse mAb specific for full-length hGH (Prospec, East Brunswick, N.J., USA) were used followed by a rabbit anti-goat IgG pAb-HRPO conjugated (Sigma-Aldrich) or a goat anti-mouse IgG pAb-HRPO conjugated (Sigma-Aldrich), respectively as a secondary antibody. A goat anti-human GCSF pAb (R&D Systems) was used to detecting the G-CSF domain, and a rabbit anti-human IFN-β pAb (PEPROTECH, Rocky Hill, USA) was used to detect the IFN-β domain.

1-(7)-Preparation of Soluble Fab and Fab-Effector Fusion Proteins

Soluble Fab and Fab-hGH fusion proteins were produced by growing *E. coli* SUPEX5 cells in 10 ml or 1 L of 2 YT medium containing 50 µg/ml kanamycin at 37° C. until an $OD_{600nm}$=0.5 followed by the addition of 0.05 mM IPTG. After 20 h of incubation at 20° C. with vigorous shaking, the culture supernatant and cell pellet were separated by centrifugation at 3,300 g for 20 min. The periplasmic extracts were obtained as described earlier. For purification, the culture supernatant and/or the periplasmic extracts were then passed through Sepharose 4B resins that were immobilized with HSA (AprilBio). After extensive washing the Fab molecules bound to the resin were eluted with elution buffer (0.1 M glycine, 10% glycerol, pH 3) followed by immediate neutralization with Tris buffer (0.5 M Tris HCl, 2 M NaCl, pH 9.0). Gel filtration of HserG/Lser was also performed after affinity purification using AKTA FPLC (GE Healthcare, Wauwatosa, Wis., USA). Briefly, Hiprep™ 16/60 Sephacryl™ S-200HRP repacked Column was equilibrated with equilibration buffer (20 mM HEPES,150 mM NaCl, pH 7.4), and loaded with 5 µl of HserG/Lser ($SL335_{Ads}$-hGH fusion). Elution was performed with equilibration buffer at 0.35 Mpa alarm pressure and 0.5 µl/min running flow rate. Fraction number 13, 16, 19 and 23 were analyzed by SDS-PAGE as described below.

1-(8) Affinity Measurement by Biolayer Interferometry

Real-time binding assays between the purified SL335 and the antigens (human SA, rat SA or mouse SA) were performed using biolayer interferometry with an Octet RED system (ForteBio, Menlo park, Calif., USA) as previously described except that AR2G (Amine Reactive Second-Generation) sensors were used (Costin et al., (2013) *J Virol.* 87, 52-66). Briefly, the predetermined concentration of SL335 was coupled to kinetics grade AR2G biosensors, and unbound Fab fragments were removed from the surfaces of the sensors by incubating in the kinetics buffer (1 M ethanolamine, pH 8.5). The probes were then allowed to bind to human SA, rat SA or mouse SA at the predetermined concentrations under pH 6.0 or pH 7.4 conditions (human SA concentration at pH 6 and pH 7.4: 200 nM, 100 nM, 50 nM, 25 nM and 12.5 nM; rat SA concentration at pH 6: 4 mM, 1 mM, 500 nM, 250 nM and 125 nM; rat SA concentration at pH 7.4: 4 mM, 2 mM, 1 mM, 500 nM and 125 nM;

mouse SA concentration at pH 6 and pH 7.4: 20 mM, 10 mM, 5 mM, 2.5 mM and 12.5 mM), followed by dissociation in PBS containing 0.1% BSA, pH 6 or pH 7.4. The binding and dissociation kinetics were calculated using the Octet QK software package, which fit the observed binding curves to a 1:1 binding model to calculate the association rate constants. The association and dissociation rate constants were calculated using at least three different concentrations of human SA, rat SA or mouse SA. The equilibrium dissociation constants were calculated as the kinetic dissociation rate constant divided by the kinetic association rate constant.

1-(9) Generation of the SL335-hGH Fusion Constructs

To create SL335ds, the mutant Fd (Cys$^{233}$ Ser$^{233}$ substitution), termed Hser, was obtained by PCR amplification from the codon-optimized Fd chain gene of SL335 using a set of PCR primer #9 (5'-ggggaatt catgaaatatctgctgcctacg-gcggcggcgggcctgctgctgctggctgcacaa-3' (SEQ ID NO:29)) and #10 (5'-gggaagcttttagctgctcttcggttccacgcgtt-3' SEQ ID NO:30)). The ~750 bp PCR product was treated with EcoR I/Hind III and ligated with pHEKA. The mutant L chain (Cys$^{214}$→Ser$^{214}$ substitution), termed Lser, was also obtained by PCR amplification from the codon-optimized L chain gene of SL335 using a set of PCR primer #11 (5'-gggggatccatgaaaaaaactgcgattgcgattgcggtgctggccggctttg-3' (SEQ ID NO:31)) and #12 (5'-gggctcgagttagctttcgc cgcg-gttaaagctctttg-3' (SEQ ID NO:32)), cut with BamH I/Xho I and cloned into pHEKA containing Hser. The cloning procedures for generating the HcysG/Lcys construct were as follow: the wild type Fd with Cys$^{233}$, termed Hcys, was PCR amplified from the codon-optimized Fd of SL335 using a set of PCR primer #9 and #13 (5'-agatccaggagctggtgcagaac-cgcagctcttcggttccacgcgtt-3' (SEQ ID NO: 33)), and the hGH containing a linker sequence was also PCR amplified from the codon-optimized hGH gene using a set of PCR primer #14 (5'-ggttctgcaccagctcctggatcttttccgaccattccgctgagccg-3' (SEQ ID NO: 34)) and #15 (5'-gggaagcttttagaagccgcaggagc-cctcca-3' (SEQ ID NO: 35)). The Hcys and the hGH genes were linked together to generate HcysG by assembly PCR using a set of PCR #9 and #15 primers, cut with EcoR I/Hind III, and cloned into pHEKA containing the wild type L chain with Cys$^{214}$ of SL335, termed Lcys. To generate the LcysG/Hcys construct, Lcys, was PCR amplified from the codon-optimized L chain of SL335 using a set of PCR primer #11 and #16 (5'-agatccaggagctggtgcagaaccgcattcgccgcggt-taaagctcttt-3' (SEQ ID NO: 36)), and the hGH containing a linker sequence was also PCR amplified from the codon-optimized hGH gene using a set of PCR primer #14 and #17 (5'-gggctcgagttagaagccgcaggagccctcca-3' (SEQ ID NO: 37)). Lcys and the hGH gene were linked to generate LcysG by assembly PCR using a set of PCR #11 and #17 primers, cut with BamHI I/Xho I and cloned into pHEKA containing the wild type Fd. To create the HserG/Lcys construct, Hser was PCR amplified from the codon-optimized wild type Fd chain using a set of PCR primer #9 and #18 (5'-gggctcgagt-tagaagccgcaggagccctcca-3' (SEQ ID NO: 38)). The PCR amplification of the hGH containing a linker sequence, assembly PCR and cloning of HserG were performed as creating the HcysG/Lcys construct. To generate the LserG/Hcys construct, Lser was PCR amplified from the codon-optimized L chain of SL335 using a set of PCR primer #11 and #19 (5'-agatccaggagctggtgcagaaccgctgctcttcggttc-cacgcgtt-3' (SEQ ID NO: 39)). PCR amplification of the hGH containing a linker sequence, assembly PCR and cloning of LserG were performed as in creating the LcysG/Hcys construct. To generate the HerG/Lser construct, the PCR amplification of HserG and the hGH, and assembly PCR were performed as creating the HserG/Lcys construct except that pHEKA containing Lser was used for cloning. LserG/Hser was also constructed as the creation of the LserG/Hcys construct except that pHEKA containing Hser was used for cloning. The PCR primers for preparing SL335-hGH fusion constructs and SL335$_{Ads}$-hGH fusion constructs are shown in Table 2 below.

TABLE 2

PCR primers for SL335-hGH or SL335$_{Ads}$-hGH fusion constructs

| Constructs | Primers | Oligonucleotide sequence |
| --- | --- | --- |
| SL335$_{Ads}$ | Primer 9 | 5'-ggggaattcatgaaatatctgctgcctacggcggcggcgggcctgctgctgctggctgcacaa-3' (SEQ ID No: 29) |
| | Primer 10 | 5'-gggaagcttttagctgctcttcggttccacgcgtt-3' (SEQ ID No: 30) |
| | Primer 11 | 5'-gggggatccatgaaaaaaactgcgattgcgattgcggtgctggccggctttg-3' (SEQ ID No: 31) |
| | Primer 12 | 5'-gggctcgagttagctttcgc cgcggttaaagctctttg-3' (SEQ ID No: 32) |
| SL335$_{wt}$-hGH fusion | Primer 13 | 5'-agatccaggagctggtgcagaaccgcagctcttcggttccacgcgtt-3' (SEQ ID No: 33) |
| | Primer 14 | 5'-ggttctgcaccagctcctggatcttttccgaccattccgctgagccg-3' (SEQ ID No: 34) |
| | Primer 15 | 5'-gggaagcttttagaagccgcaggagccctcca-3' (SEQ ID No: 35) |
| | Primer 16 | 5'-agatccaggagctggtgcagaaccgcattcgccgcggttaaagctcttt-3' (SEQ ID No: 36) |
| | Primer 17 | 5'-gggctcgagttagaagccgcaggagccctcca-3' (SEQ ID No: 37) |
| SL335$_{Ads}$-hGH fusion | Primer 18 | 5'-agatccaggagctggtgcagaaccgctgctcttcggttccacgcgtt-3' (SEQ ID No: 38) |
| | Primer 19 | 5'-agatccaggagctggtgcagaaccgctttcgccgcggttaaagctctttg-3' (SEQ ID No: 39) |

1-(10)-Generation of the SL335-GCSF Fusion Constructs

The cloning procedures for generating the HcysGF/Lcys construct were as follow; Hcys was PCR amplified from the codon-optimized H chain of SL335 using a set of PCR primer #9 and #20 (5'-agatccaggagctggtgcagaaccgctttcgccgcggttaaagctctttg-3' (SEQ ID NO: 40)), and the G-CSF containing a linker sequence was also PCR amplified from the codon-optimized G-CSF gene using a set of PCR primer #21 (5'-ggttctgcaccagctcctggatctgcgcctacctatcgcgcgagca-3' (SEQ ID NO:41)) and #22 (5'-gggaagcttattaaggctgtgccagatggcgcag-3' (SEQ ID NO:42)). The Hcys and the G-CSF genes were linked together by assembly PCR using a set of PCR #9 and #22 primers, cut with EcoR I/Hind III, and cloned into pHEKA containing the L chain of SL335. To generate the LcysGF/Hcys construct, Lcys was PCR amplified from the codon-optimized L chain of SL335 using a set of PCR primer #11 and #23 (5'-agatccaggagctggtgcagaaccgcattcgccgcggttaaagctcttt-3' (SEQ ID NO: 43)), and the G-CSF containing a linker sequence was also PCR amplified from the codon-optimized G-CSF gene using a set of PCR primer #21 and #24 (5'-taacagatctgcggccgcactcgagattaaggctgtgccagatggcgcag-3' (SEQ ID NO: 44)). The Lcys and G-CSF genes were linked by assembly PCR using a set of PCR primer #11 and #25 (5'-agatccaggagctggtgcagaaccgctgctcttcggttccacgcgtt-3' (SEQ ID NO: 45)), cut with BamH I/Xho I and cloned into pHEKA containing the Fd of SL335. To create the HserGF/Lser construct, Hser was PCR amplified from the codon-optimized Fd of SL335 using a set of PCR #9 and #25 primers. The Hser and the G-CSF genes were linked together by assembly PCR using a set of PCR #9 and #22 primers, cut with EcoR I/Hind III, and cloned into pHEKA containing Lser. To generate the LserGF/Hser construct, Lser was PCR amplified from the codon-optimized L chain of SL335 using a set of PCR primer #11 and #26 (5-agatccaggagctggtgcagaaccgctttcgccgcggttaaagctctttg-3(SEQ ID NO: 46)), and the G-CSF containing a linker sequence was also PCR amplified from the codon-optimized G-CSF gene using a set of PCR #21 and #24 primers. The Lcys and G-CSF genes were linked by assembly PCR using a set of PCR #11 and #25 primers, cut with BamH I/Xho I and cloned into pHEKA containing Hser. The PCR primers for preparing SL335-GCSH fusion constructs and SL335$_{Ads}$-GCSF fusiong constructs are shown in Table 3 below.

TABLE 3

PCR primers for SL335-GCSH or SL335$_{Ads}$-GCSF fusion constructs

| Constructs | Primers | Oligonucleotide sequence |
|---|---|---|
| SL335r$_{wt}$-GCSF fusion | Primer 20 | 5'-agatccaggagctggtgcagaaccgcagctcttcggttccacgcgtt-3' (SEQ ID No: 40) |
| | Primer 21 | 5'-ggttctgcaccagctcctggatctgcgcctacctatcgcgcgagca-3' (SEQ ID No: 41) |
| | Primer 22 | 5'-gggaagcttattaaggctgtgccagatggcgcag-3' (SEQ ID No: 42) |
| | Primer 23 | 5'-agatccaggagctggtgcagaaccgcattcgccgcggttaaagctcttt-3' (SEQ ID No :43) |
| | Primer 24 | 5'-taacagatctgcggccgcactcgagattaaggctgtgccagatggcgcag-3' (SEQ ID No :44) |
| SL335$_{Ads}$-GCSF fusion | Primer 25 | 5'-agatccaggagctggtgcagaaccgctgctcttcggttccacgcgtt-3' (SEQ ID No: 45) |
| | Primer 26 | 5'-agatccaggagctggtgcagaaccgctttcgccgcggttaaagctctttg-3' (SEQ ID No :46) |

1-(11) Generation of the SL335-IFN-b Fusion Constructs

The cloning procedures for generating the HcysIFNb/Lcys construct were as follow. Hcys was PCR amplified from the codon-optimized H chain of SL335 using a set of primer #9 and #27 (5'-agatccaggagctggtgcagaaccgcagctcttcggttccacgcgtt-3' (SEQ ID NO: 47)), and the IFN-b containing a linker sequence was also PCR amplified from the codon-optimized IFN-b1a gene using a set of PCR primer #28 (5'-ggttctgcaccagctcctggatcttcatacaacctgctgggcttcctg-3' (SEQ ID NO:48)) and #29 (5'-gggaagcllllagttgcgcagatagccggtcag-3' (SEQ ID NO:49)). Hcys and the IFN-b1a genes were linked together by assembly PCR using a set of PCR #9 and #29 primers, cut with EcoR I/Hind III, and cloned into the pHEKA containing Lcys. To create the HserIFN-b/Lser construct, Hser was PCR amplified from the codon-optimized H chain of SL335 using a set of PCR primer #9 and #30 (5'-agatccaggagctggtgcagaaccgctgctcttcggttcacgcgtt-3' (SEQ ID NO:50)). Hser and the IFN-1a genes were linked together by assembly PCR using a set of PCR #9 and #29 primers, cut with EcoR I/Hind III, and cloned into the pHEKA containing Lser. The PCR primers for preparing SL334-IFNb fusion constructs and SL335$_{Ads}$-IFNb fusion constructs are shown in Table 4 below.

TABLE 4

PCR primers for SL335-IFNb or SL335$_{Ads}$-IFNb fusion constructs

| Constructs | Primers | Oligonucleotide sequence |
|---|---|---|
| SL335$_{Ads}$-IFNb and SL335-IFNb fusion | Primer 27 | 5'-agatccaggagctggtgcagaaccgcagctcttcggttccacgcgtt-3' (SEQ ID NO: 47) |
| | Primer 28 | 5'-ggttctgcaccagctcctggatcttcatacaacctgctgggcttcctg-3' (SEQ ID NO: 48) |
| | Primer 29 | 5'-gggaagcttttagttgcgcagatagccggtcag-3' (SEQ ID NO: 49) |
| | Primer 30 | 5'-agatccaggagctggtgcagaaccgctgctcttcggttccacgcgtt-3' (SEQ ID NO: 50) |

1-(12) Generation of the EGL4-hGH and the 1b28-hGH Fusion Constructs

EGL4, a human anti-EGFR Fab, and 1b28, a human anti-IL-1b Fab, had been isolated from HuDVFab-8L antibody library (unpublished, AprilBio Co.). To create EGL4$_{wt}$ fusions using the same PCR primer sets except that 1b28 cDNA was served for PCR templates. The PCR primers for preparing EGL4-hGH and the 1b28-hGH fusion constructs are shown in Table 5 below,

TABLE 5

PCR primers for repaing EGL4-hGH and the 1b28-hGH fusion constructs

| Constructs | Primers | Oligonucleotide sequence |
|---|---|---|
| EGL4-hGH and 1b28-hGH fusion | Primer 31 | 5'-gggaagcttattaactagatttgggctcaactctcttg - 3' (SEQ ID NO. 51) |
| | Primer 32 | 5' -gggctcgagttagcattcgccgcggttaaagctcttt - 3' (SEQ ID NO. 52) |
| | Primer 33 | 5' -gggctcgagttagctttcgccgcggttaaagctcttt - 3' (SEQ ID NO. 53) |
| | Primer 34 | 5' - agatccaggagctggtgcagaaccacaagatttgggctcaactctcttgtc - 3' (SEQ IN NO. 54) |
| | Primer 35 | 5' - agatccaggagctggtgcagaaccactagatttgggctcaactctcttgtc - 3' (SEQ ID NO. 55) | and EGL4$_{Ads}$, Hcys and Hser were PCR amplified from the H chain gene of EGL4 cDNA using a set of PCR primer #5 and #6, and #5 and #31 (5'-gggaagcttattaactagatttgggct-caactctcttg-3' (SEQ ID NO: 51)), respectively. The ~750 bp PCR products were treated with EcoR I/Hind III and ligated with pHEKA, followed by transforming MC1061 competent cells. Lcys and Lser were also PCR amplified the L chain gene of EGL4 cDNA using a set of PCR primer #11 and #32 (5'-gggctcgagttagcattcgccgcggttaaagctcttt-3' (SEQ ID NO: 52)), and #11 and #33 (5'-gggctcgagttagctttcgccgcggt-taaagctcttt-3' (SEQ ID NO: 53)), respectively. They were cut with BamH I/Xho I and cloned into the pHEKA containing Hcys or Hser of EGL4, respectively. To create the EGL4$_{wt}$-hGH fusion construct, the cloning procedures for generating the HcysG/Lcys construct were as follow. Hcys was PCR amplified from the H chain of EGL4 cDNA using a set of PCR primer #5 and #34 (5'-agatccaggagctggtgcagaacca-caagatttgggctcaactctcttgtc-3' (SEQ ID NO: 54)), and the hGH containing a linker sequence was also PCR amplified from the codon-optimized hGH gene using a set of PCR #14 and #15 primers. The Hcys and the hGH genes were linked together by assembly PCR using a set of PCR #5 and #15 primers, cut with EcoR I/Hind III, and cloned into the pHEKA containing Lcys of EGL4. For creating the EGL4$_{Ads}$-hGH fusion construct construct, Hser was PCR amplified from the H chain of EGL4 cDNA using a set of PCR primer #5 and #35 (5-agatccaggagctggtgcagaaccacta-gatttgggctcaactctcttgtc-3' (SEQ ID NO: 55)), and the hGH containing a linker sequence was also PCR amplified from the codon-optimized HGH gene using a set of PCR #14 and #15 primers. The Hser and the hGH genes were linked together by assembly PCR using a set of PCR #5 and #15 primers, cut with EcoR I/Hind III, and cloned into the pHEKA containing Lser of EGL4$_{Ads}$. 1b28$_{wt}$, 1b28$_{Ads}$, 1b28$_{Ads}$-hGH and 1b28$_{Ads}$-hGH were created as EGL4-hGH 1-(13) SDS-PAGE and Western Blot Analyses For SDS-PAGE analysis, purified SL335$_{wt}$-hGH and SL335$_{Ads}$-hGH proteins were resuspended in NuPAGE® LDS Sample Buffer (Invitrogen) with or without NuPAGE® Sample Reducing Agent (Invitrogen), and loaded onto the gel at 7 μg/well concentration. The protein bands were visualized by using Coomassie Blue staining (Bio-Rad). For the western blot analysis, 500 ng of affinity-purified SL335$_{wt}$-hGH and SL335$_{Ads}$-hGH were loaded onto each well as above, and transferred to nitrocellulose membrane. After blocking the membrane with 3% skimmed milk (Bio-Rad) in PBS containing 0.01% Tween (Sigma-Aldrich), proteins were detected by incubation with a goat anti-human kappa L chain pAb conjugated with AP (Bethyl). The nitro blue tetrazolium chloride (NBT)/5-bromo-4-chloro-3-indo-lyl phosphate (BCIP) substrate (Duchefa) was added onto the membrane to visualize the binding signals.

1-(14) Chip-Based Capillary Electrophoresis

Chip-based capillary electrophoresis was carried out with the Agilent 2100 Bioanalyzer system (Agilent Technologies, Santa Clara, Calif., USA). The protein samples were prepared according to the manufacturers protocol and analyzed on the Protein 80 kit, which is recommended for the analysis of proteins between 5 to 80 kDa. Briefly, the samples were mixed with sample buffer in the presence or absence of DTT for reducing or non-reducing electrophoresis, respectively. The samples were denatured at 95° C. and loaded on the chip which had been filled with proper reagents including the fluorescent dye and gel solution. The chip was then inserted into the system and run on the system using the Expert 2100 software. The results were plotted to reflect fluorescence intensity units against protein size.

1-(15) MALDI-TOF Mass Spectrometry

MALDI-TOF mass spectrometry was performed on an Autoflex III Smartbeam device (Bruker Daltonics, Billerica, Mass., USA). Sample was mixed with the same volume of MALDI matrix (10 mg/mL of a-cyano-4-hydroxycinnamic acid) and spotted on a MALDI target plate. External calibration was performed with a Peptide and Protein MALDI-MS Calibration Kit (Sigma-Aldrich). Mass spectra in the m/z range of 15000160000 and 1000070000 were acquired for SL335$_{wt}$-hGH fusion and SL335$_{Ads}$-hGH fusion, respectively, in the positive ion mode.

1-(16) In Vitro hGH Bioactivity Assay

Nb2-11 rat lymphoma cells (Sigma-Aldrich) were grown in complete DMEM supplemented with 5% horse serum (Sigma-Aldrich) and 1% PenicillinStreptomycin (Invitrogen) in a humidified 5% $CO_2$ incubator at 37° C. (Tanakaet al., 1980). The cells were washed two times with DMEM, centrifuged at 1,000 g for 5 min and resuspended in DMEM containing 5% (v/v) horse serum at $8 \times 10^4$ cells/ml. A 50 µg aliquot of the cell suspension was added to each well of 96-well plates, and incubated overnight. The cells were then treated with increasing concentrations (0-20 nM) of Growtropin® (a unmodified rhGH; Dong-A Pharmaceuticals, Seoul, South Korea) or SL335$_{Ads}$-hGH in 50 ml DMEM containing 5% horse serum for 48 h at 37° C. Following the incubation, 10 µl of CCK-8 (Dojindo, Mashiki-machi, Japan) was added to each well, and incubated for 4 h. The absorbance was recorded on a microplate reader (Bio-Rad) at a wavelength of 450 nm.

1-(1 7) Serum Stability of SL335Δds-hGH

SL335$_{wt}$ and SL335$_{Ads}$-hGH (10 µg/ml final concentration) were resuspended in fetal bovine serum (FBS) (Thermo Scientific, Waltham, Mass., USA) containing 0.03% sodium azide, and incubated for 16 days at 37° C. Small aliquots (50 ml) were taken every day and stored at −20° C. before use. The binding reactivity to HSA was determined by ELISA, and the in vitro hGH bioactivity was measured using Nb2-11 cells(Sigma-Aldrich) as described above.

1-(18) In Vivo Pharmacokinetics Assay

The PK studies were performed at a certified CRO company (ChemOn, Suwon, South Korea). The animals were fed a standard diet of rodent pellets and water ad libitum and kept in a room of constant humidity and temperature with controlled lighting (12 h light followed by 12 h dark). Briefly, SL335 and Neg Fab (an irrelevant human Fab) were intravenously (I.V.) or subcutaneously (S.C.) injected separately into groups of three Sprague Dawley rats at 1 mg/kg, and serum samples were obtained at several time points (5 min, 15 min, 30 min, 1 h, 2 h, 4 h, 8 h, 24 h, 48 h, 96 h and 144 h for I.V., and 5 min, 15 min, 30 min, 1 h, 2 h, 4 h, 8 h, 24 h, 48 h, and 96 h for S.C.). The concentration of SL335 and Neg Fab in the serum samples was measured by sandwich ELISA using the mouse anti-human IgG Fd mAb and the goat anti-human kappa L chain pAb conjugated with HRPO as a capture and detecting antibodies, respectively. Human Fab fragments of known concentration were also included in the assay to obtain a standard curve. Curves of serum concentration versus time were fitted for a non-compartment model using WinNonlin software (SL335 and Neg Fab) and plotted using Sigma Plot software. Similarly, Growtropin® and SL335$_{Ads}$-hGH were intravenously or subcutaneously injected separately into group of three to four rats. The dosages of Growtropin® and SL335$_{Ads}$-hGH for I.V. administration were 0.3 mg/kg, and for S.C. administration were 0.6 mg/kg, respectively. Serum samples were obtained at several time points (5 min, 15 min, 30 min, 1 h, 2 h, 3 h, 4 h, 6 h and 8 h for Growtropin® and 5 min, 30 min, 1 h, 2 h, 4 h, 8 h, 24 h, 48 h, 96 h and 144 h for SL335$_{Ads}$-hGH. The amount of Growtropin® in the serum samples was measured using the hGH ELISA detection kit (Genway, San Diego, Calif., USA), and that of SL335$_{Ads}$-hGH was measured by sandwich ELISA as described above. A serum concentration versus time curve was fitted for a one compartment model using Phoenix™ WinNonlin software (Version 6.2).

1-(19) In Vivo Pharmacodynamics Assay

The ability of daily dosing of Growtropin® and once-weekly dosing of SL335$_{Ads}$-hGH to promote weight gain was analyzed in hypophysectomized rats by using S.C. administration at ChemOn as previously described (see Clark et al., (1996) *J. Biol. Chem.* 271, 21969-21977). Briefly, young hypophysectomized Sprague Dawley rats (Harlan, Tokyo, Japan) were purchased, and any animal gaining more than 7 g over the first 15 days following surgery was excluded from the study. The animals were randomized for five treatment groups (Excipient only, daily injection of 0.3 mg/kg Growtropin® and once-weekly injection of 0.6 mg/kg, 1.2 mg/kg or 2.4 mg/kg SL335$_{Ads}$-hGH). The body weights were recorded daily after starting dosage regimen. The tibia bone growth was carefully measured with a bone caliper. Statistical comparisons were made using an analysis of variance followed by Dunnetts Multiple Comparison Test, and p values less than 0.05 were considered significant.

2. Experimental Results 2-(1) Isolation of Anti-SA Fab Clones

Figure 1B:
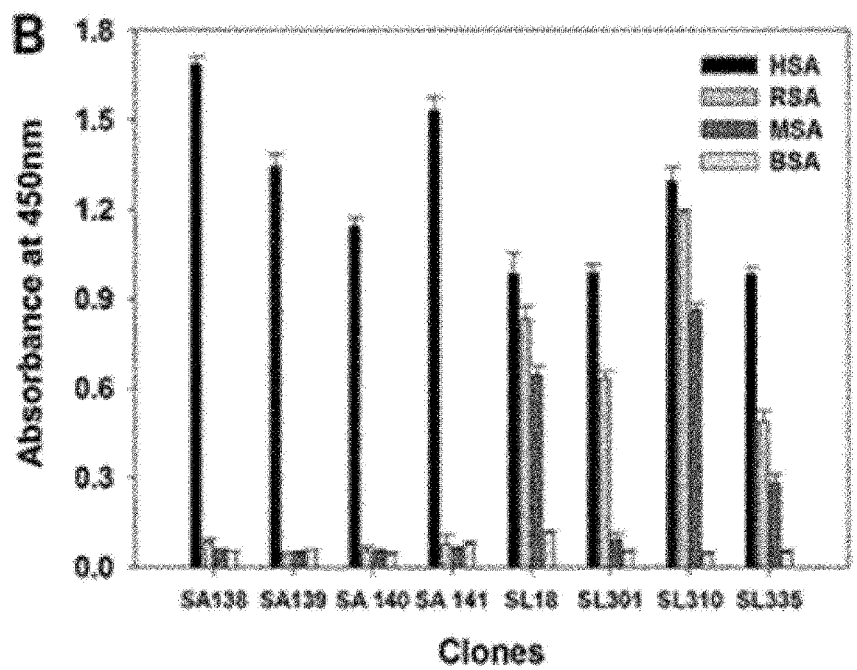
Figure 2A:
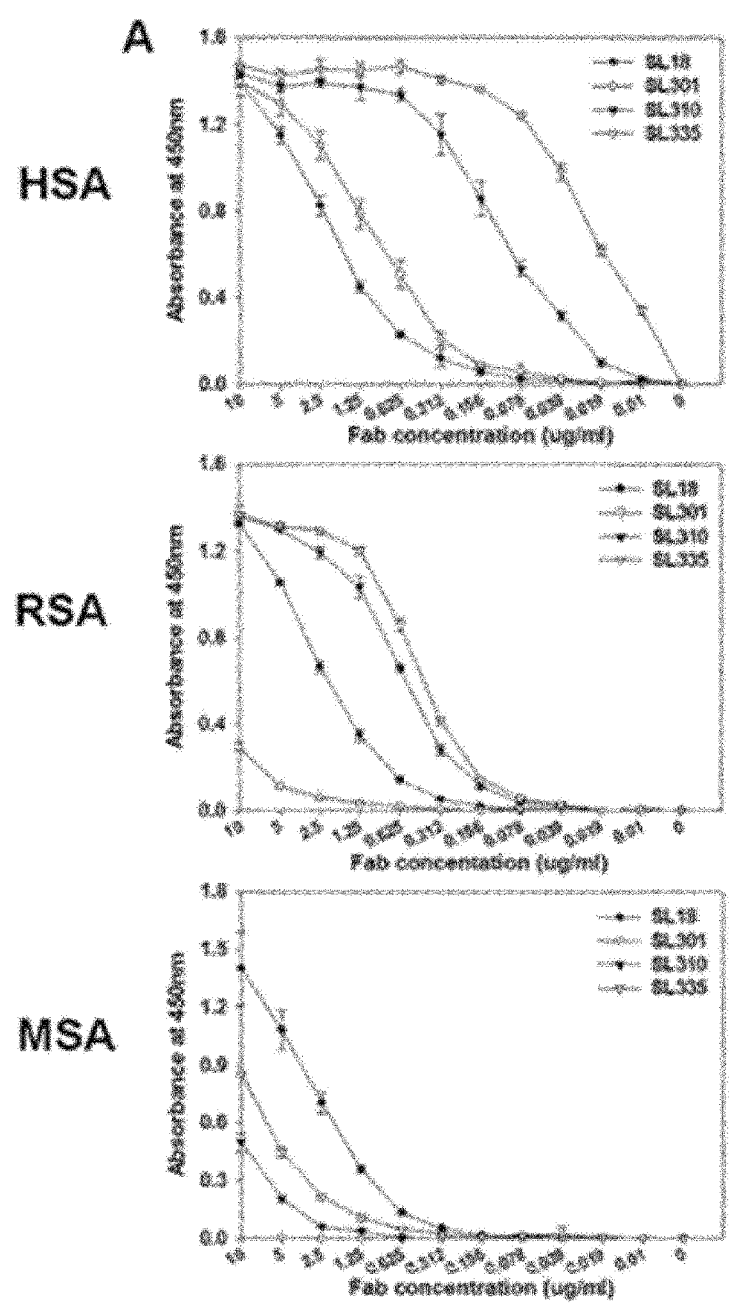
FIGS. 2A and 2B show the determination of the antigen-binding specificity of the human Fab clones by ELISA under pH 6 (FIG. 2A) or pH 7.4 (FIG. 2B) conditions.
Figure 2B:
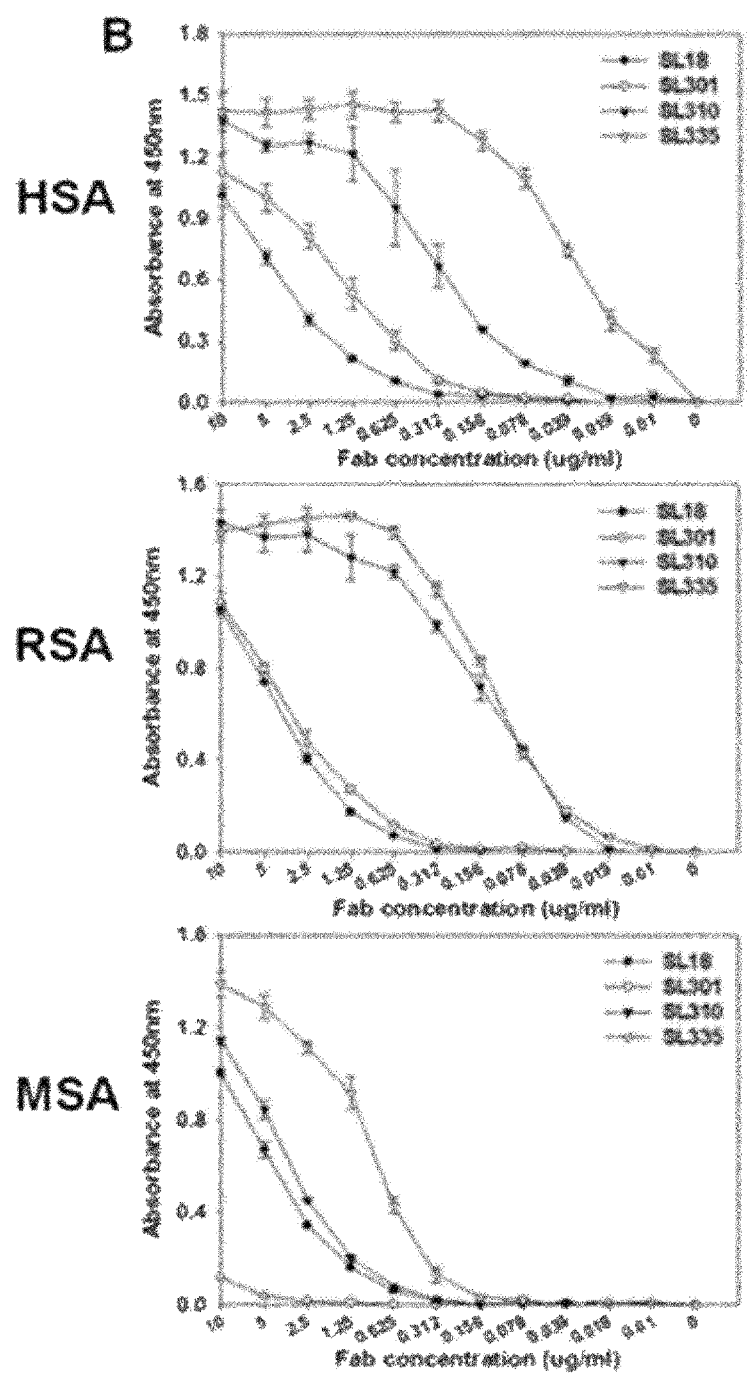

The HuDVFab-8L antibody library was selected against the magnetic beads conjugated with human SA, rat SA or mouse SA at pH 6 or pH 7.4. After three rounds of biopanning, a monoclonal phage ELISA was performed to identify the phage antibody clones that were specific for the antigens. More than 60 positive clones were identified by the ELISA (data not shown), and a DNA sequencing analysis of the $V_H$ and the $V_L$ genes identified eight discrete phage antibodies, termed SA138, SA139, SA140, SA141, SL18, SL301, SL310 and SL335, respectively. The binding reactivity of these clones to human SA, rat SA, mouse SA or bovine SA was confirmed by a monoclonal phage ELISA under pH 6 or pH 7.4 conditions (FIGS. 1A & 1B). Three phage antibody clones, SA138, SA139 and SA141, were reactive only to human SA regardless of pH conditions. SA140 also recognized human SA only at pH 7.4, but its binding reactivity disappeared at pH 6. On the other hand, SL18, SL310 and SL335 bound to human SA, rat SA and mouse SA under both pH conditions with slightly different intensities. SL301 was significantly reactive to human SA and rat SA at both pH, and weakly to mouse SA at pH 7.4 only. None of eight Fab clones were reactive to bovine SA. SL18, SL301, SL310 and SL335 were further characterized because of their cross-reactivity to SAs from at least two different species. The Fd and the L chain genes of four phage antibody clones were subcloned into the pHEKA vector for periplasmic expression in *E. coli*, and the soluble Fab fragments were prepared from the culture supernatant or periplasmic extracts. After affinity purification, an ELISA was performed to compare the binding reactivity of these fragments to human SA, rat SA or mouse SA under pH 6 (FIG. 2A) and pH 7.4 conditions (FIG. 2B). HSA, RSA, MSA or BSA at 5 µg/ml concentrations was immobilized in each well of the microtiter plates, and four purified Fab molecules (SL18, SL301, SL310 and SL335) were allowed to bind to the antigens at pH 6.0 (FIG. 2A) or at pH 7.4 (FIG. 2B). The goat antihuman kappa L chain pAb HRPO conjugate was used as a secondary antibody. The binding signals were visualized using TMB substrate, and the absorbance at 450 nm was measured using an ELISA reader (Bio-Rad).

The data represent the average standard deviation of three experiments. In the human SA binding, the order of binding signals was SL335>SL310>SL301>SL18 at both pH 6 and pH 7.4. In the rat SA binding, the order was SL335>SL310>SL301>SL18 at pH 6, and SL335=SL310>SL301=SL18 at pH 7.4. In the mouse SA binding, the order was SL18>SL335>SL310 at pH 6, and SL335>SL310>SL18 at pH 7.4. In accordance with FIG. 2, SL301 failed to bind to mouse SA at pH 6, yet very weakly at pH 7.4. SL335 was found to be the best binder among four the Fab clones to both human SA and rat SA regardless of the pH condition. SL335 bound to human SA at pH 6 twice as strongly than it did at pH 7.4 (50% binding signal at 20 ng/ml vs. 40 ng/ml), 20-fold stronger than to rat SA under the same pH condition (50% binding signal at 20 ng/ml vs. 400 ng/ml), and four-fold stronger than to rat SA at pH 7.4 (50% binding signal at 40 ng/ml vs. 160 ng/ml).

2-(2) Cross-Reactivity and Binding Affinity of SL335

Figure 3A:
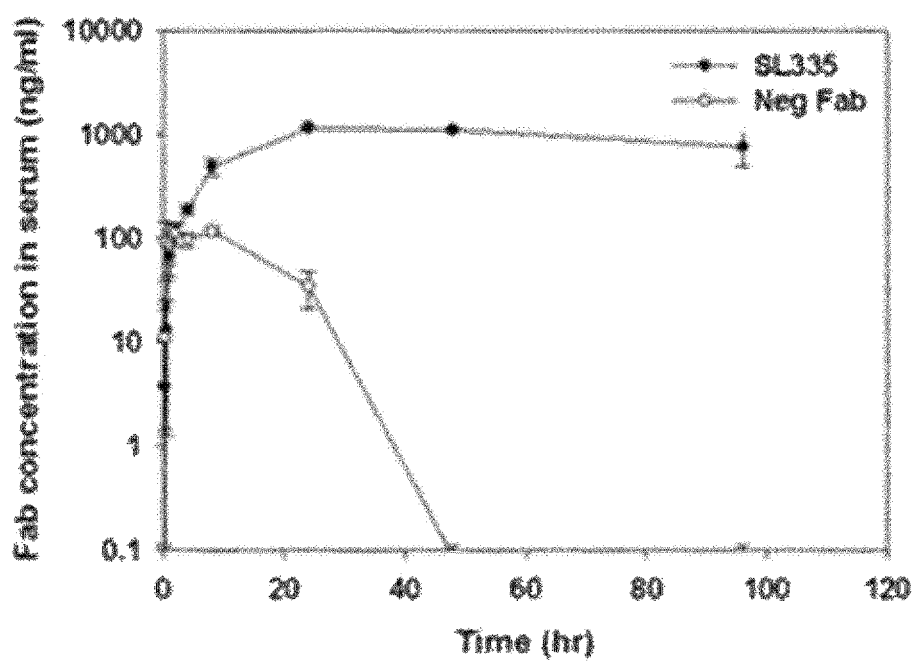
FIGS. 3A and 3B represent in vivo pharmacokinetics of SL335 in intravenous administration (FIG. 3A) and the subcutaneous injection (FIG. 3B).
Figure 3B:
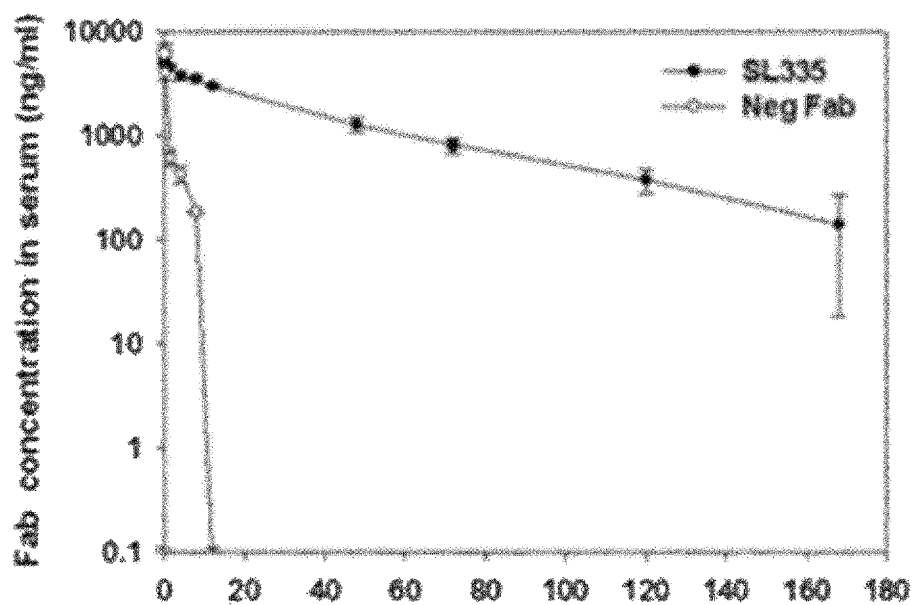

Since SL335 was the best binder among four anti-human SA Fab clones, its cross-reactivity was further analyzed by ELISA. Binding reactivity to human SA, rat SA and mouse SA was reproduced as shown in FIG. 2. It was also found that SL335 intensely recognized cynomolgus monkey SA and weakly bound to canine SA. However, SL335 did not recognize rabbit SA as well as other irrelevant antigens including EGFR, EpCAM, IL-15Ra, IL-lb, CD16a or c-MET. The binding affinities of SL335 to human SA, rat SA and mouse SA at pH 6 or pH 7.4 were further measured via biolayer interferometry by passing through different concentration of the antigens on biosensors that were coated with SL335 (see Table 6 below). The results correlated well with the ELISA data in FIG. 2 in that the dissociation constants of SL335 to HSA were 9 nM at pH 6 and 13 nM at pH 7.4, respectively, and those to RSA were 122 nM and 65 nM at pH 6 and pH 7.4, respectively. The binding affinities of SL335 for MSA were approximately 10 mM at pH 6 and 1.6 mM at pH 7.4, but these data were not included in Table 6 due to lack of reliability.

at 1 mg/kg, and serum samples were collected at several time points (5 min, 15 min, 30 min, 1 h, 2 h, 4 h, 8 h, 24 h, 48 h, 96 h and 144 h for I.V., and 5 min, 15 min, 30 min, 1 h, 2 h, 4 h, 8 h, 24 h, 48 h, and 96 h for S.C.). The concentration of SL335 and Neg Fab in the serum samples was measured by sandwich ELISA using the mouse anti-human IgG Fd mAb and the goat anti-human kappa L chain pAb conjugated with HRPO as a capture and detecting antibodies, respectively. Human Fab fragments of known concentration were also included in the assay to obtain a standard curve. Curves of serum concentration versus time were fitted for a one compartment model using WinNonlin software (SL335 and Neg Fab) and a two-compartment model using Sigma Plot software. In intravenous administration, the terminal half-life ($t_{1/2}$) of SL335 was 37 h and its area under the curve ($AUC_{0\to\infty}$) was 187 h mg/ml, representing a ten-fold increase in the $t_{1/2}$ and a 26-fold increase in $AUC_{0\to\infty}$ compared to Neg Fab (3.8 h and 7 h mg/ml, respectively) (FIG. 3A). The subcutaneous injection of SL335 produced similar measurements, including a nine-fold increase in $t_{1/2}$ (120 h vs. 13 h) and a 44-fold increase $AUC_{0\to\infty}$ compared to Neg Fab (87 vs. 2 h mg/ml) (FIG. 3B). These results clearly showed an extended serum half-life of SL335, and implied that SL335 would not interfere with the interaction between RSA and FcRn in rats.

2-(4) Production of the SL335-hGH Fusions

SL335 was used to create two SL335-hGH fusions and four additional SL335-hGH fusions by genetically fusing the recombinant hGH (27-191 aa) to the N- or C-terminus of the Fd or the L chain via a short peptide linker. Recombinant hGH cDNA (27-191 aa) was fused to the C-terminus of the H or L chain of $SL335_{wt}$ in a classic Fab form via a short peptide linker, resulting in construction of two fusion formats (HcysG/Lcys and LcysG/Hcys). Four additional fusion formats (HserG/Lcys, LserG/Hcys, HserG/Lser and LserG/Hser) were also constructed as above except for using SL335 in a null form ($SL335_{null}$) or a ds Fab form ($SL335_{\Delta ds}$) of which $Cys^{233}$ at the C-terminal $C_{H1}$ and/or

TABLE 6

Determination of binding affinity of SL335 and HserG/Lser by Biolayer interferometry binding assay

| Binder | Antigen | pH condition | KD (M) | K on (1/Ms) | K off (1/s) | Full R^2 | Chi2 values |
|---|---|---|---|---|---|---|---|
| SL335 | HSA | pH 6.0 | 8.68E−09 | 1.79E+05 | 1.55E−03 | 0.920807 | 0.479289 |
|  |  | pH 7.4 | 1.30E−08 | 1.17E+05 | 1.52E−03 | 0.966233 | 0.378597 |
|  | RSA | pH 6.0 | 1.22E−07 | 4.71E+04 | 5.76E−03 | 0.882417 | 1.299042 |
|  |  | pH 7.4 | 6.53E−08 | 4.32E+04 | 2.82E−03 | 0.839612 | 2.718799 |
| HserG/ | HSA | pH 6.0 | 1.68E−09 | 5.00E+05 | 8.41E−04 | 0.951998 | 1.015294 |
| Lser |  | pH 7.4 | 1.51E−09 | 6.73E+05 | 1.02E−03 | 0.915507 | 0.652098 |
|  | RSA | pH 6.0 | 4.99E−07 | 6.96E+04 | 3.47E−02 | 0.980042 | 0.214899 |
|  |  | pH 7.4 | 8.36E−08 | 9.33E+04 | 7.80E−03 | 0.836744 | 1.101016 |

The binding kinetics and the dissociation kinetics were calculated using the Octet QK software package.

2-(3) In Vivo Pharmacokinetics of SL335

Figure 4:
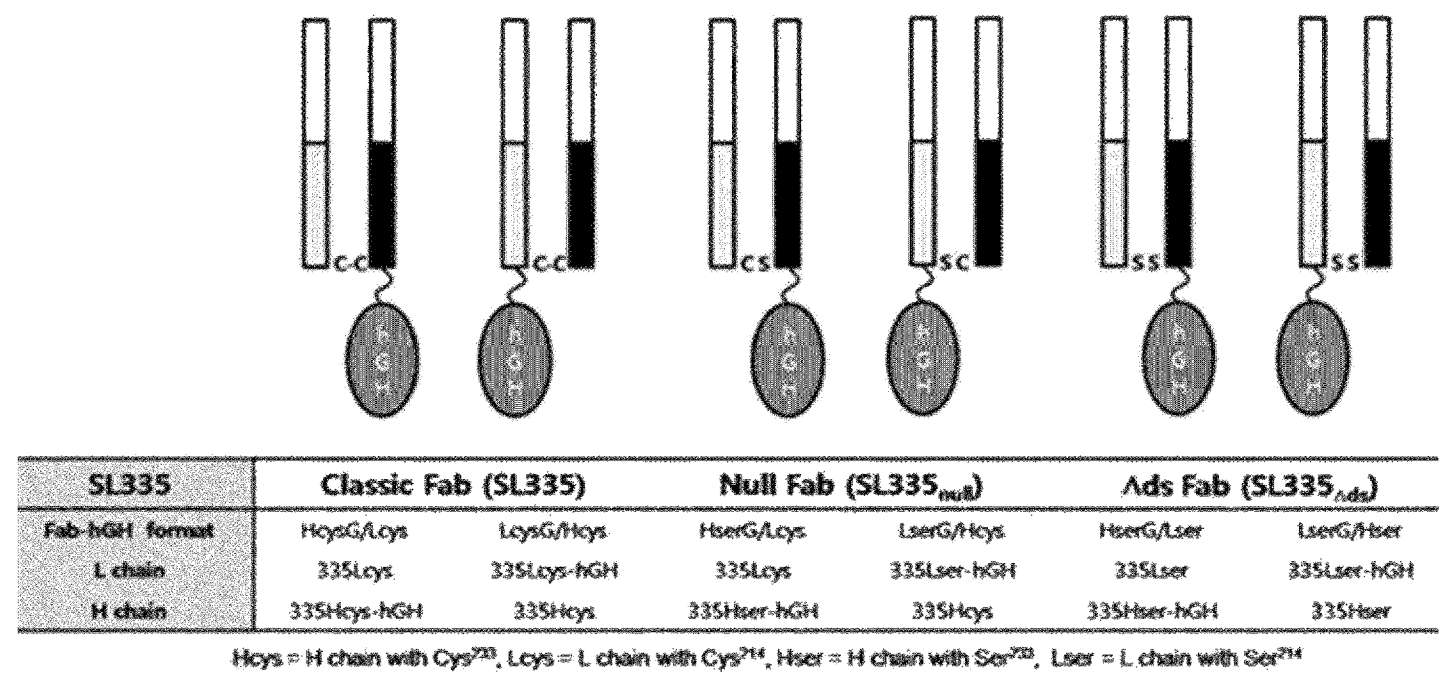
Figure 5A:
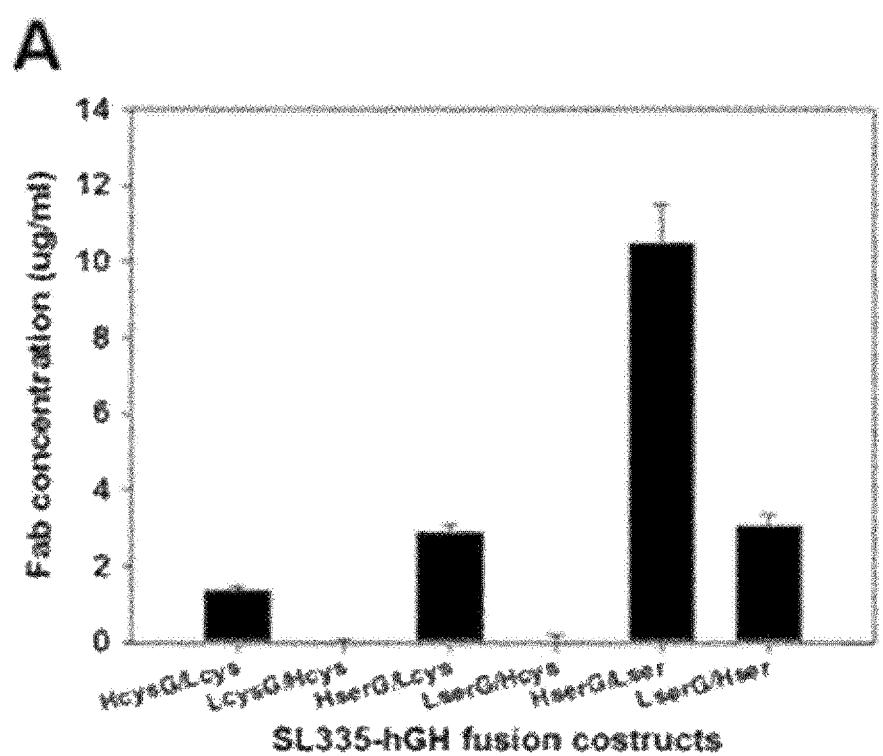
FIGS. 5A through 5D show the results of ELISA to determine the yields and the binding reactivity of soluble SL335-hGH fusions in E. coli culture supernatant. The binding signals were visualized using TMB substrate, and the absorbance at 450 nm was measured using an ELISA reader. The data represent the average±SD of three experiments.
Figure 5B:
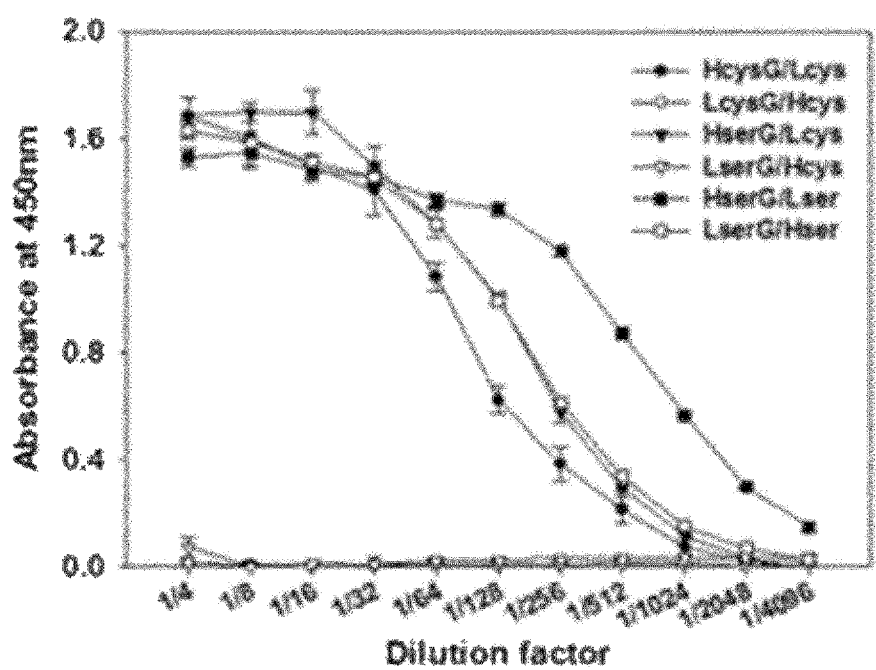
Figure 5C:
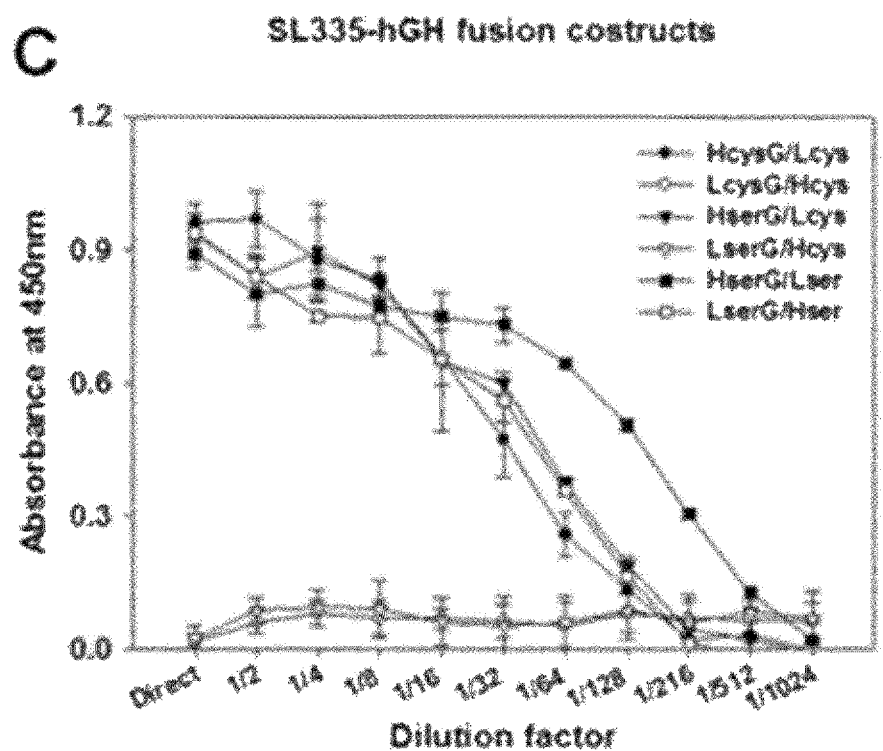
Figure 5D:
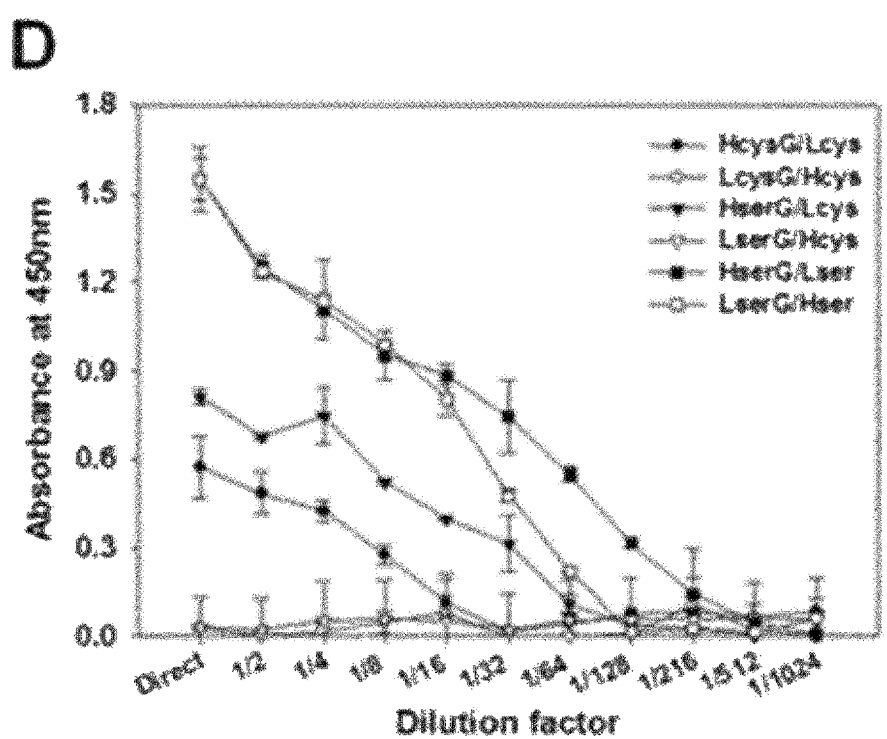

Of all of the plasma proteins, HSA has an exceptionally long half-life through the FcRn-mediated recycling mechanism, and is commonly used as a fusion partner for extending the half-lives of therapeutic proteins. In addition, antibody fragments that are associated with serum albumin have been known to have an extended serum half-life. Thence, a pharmacokinetic analysis was performed to verify whether SL335 also has a long serum half-life. Human Fab with an unknown binding specificity was included as a negative control (Neg Fab). SL335 and Neg Fab were intravenously or subcutaneously injected separately into group of three rats $Cys^{214}$ at the C-terminal $C_{Lk}$ were replaced with Ser. For periplasmic expression of the fusion proteins, the ompA (MKKTAIAIAVLAGFATVAQA (SEQ ID No:56)) leader sequence was located at the upstream of the L chain or the L-hGH fusions, and the pelB leader sequence (MKYLL-PTAAAGLLLLAAQPAMA (SEQ IN No:57)) was located at the upstream of the H chain or the H-hGH fusions. In these preliminary experiments, the genetic linking of hGH to the N-terminus of the Fd or the L chain resulted in low or no expression of soluble fusion proteins. The fusion of hGH to the C-terminus of the Fd also showed low expression yields, and seemed to interrupt the folding of the hGH domain probably due to aberrant disulfide bonding in the SL335-hGH fusion (data not shown). Previously, it had been reported that the removal of the interchain disulfide bond of a Fab by mutating the C-terminal Cys residues in the $C_{H1}$ and the $C_{Lk}$ ($Cys^{233}$ and $Cys^{214}$, respectively) does not affect the levels of periplasmic production, stability upon extraction and purification, serum stability or serum half-life (see Kabat et al., (1991) *Sequences of Proteins of Immunological Interest*; Humphreys et al., (1997) *J. Immunol. Methods.* 209, 193202; Humphreys et al., (2007) *Protein Eng Des Sel.* 20, 227234.). By replacing both $Cys^{233}$ of the $C_{H1}$ and $Cys^{214}$ of the $C_{Lk}$ with serine ($Cys^{233}$ $Ser^{233}$ and $Cys^{214}$ $Ser^{214}$ substitutions), we tested whether these Cys residues in SL335 modulate the soluble expression and appropriate folding of SL335-hGH fusions. FIG. 4 illustrates six SL335-hGH fusion constructs. Other than $SL335_{wt}$ and $SL335_{Ads}$, one more SL335 variant, termed $SL335_{null}$, was also created by substituting either $Cys^{233}$ of the $C_{H1}$ or $Cys^{214}$ of the $C_{Lk}$, with Ser to elucidate the effect of each cysteine residues ($Cys^{233}$ or $Cys^{214}$) separately. Two $SL335_{wt}$ fusion derivatives were HcysG/Lcys ($HCys^{233}$-hGH fusion paired with $LCys^{214}$) and LcysG/Hcys ($LCys^{214}$-hGH fusion paired with $HCys^{233}$), two $SL335_{null}$ fusion derivatives were HserG/Lcys ($HSer^{233}$-hGH fusion paired with $LCys^{214}$) and LserG/Hcys ($LSer^{214}$-hGH fusion paired with $HCys^{233}$). Finally, two $SL335_{Ads}$ fusion derivatives were HserG/Lser ($HSer^{233}$-hGH fusion paired with $LSer^{214}$) and LserG/Hser ($LSer^{214}$-hGH fusion paired with $HSer^{233}$). These six SL335-hGH fusion constructs were expressed in the *E. coli* SUPEX5 host cells, the yields and HSA-binding reactivity of these six SL335-hGH fusion proteins in the culture supernatant were analyzed by ELISA. *E. coli* clones expressing SL335-hGH fusion proteins were grown under the identical conditions in the presence of IPTG, and culture supernatant was harvested by brief centrifugation. The concentration of soluble SL335-hGH fusions was measured by sandwich ELISA using the mouse anti-human Fd mAb as a capturing Ab and the goat anti-human kappa L chain pAb conjugated with HRPO was used as a detecting antibody (FIG. 5A). No soluble Fab forms were detected from LcysG/Hcys or LserG/Hcys. Although the data were not presented, the western blot using the *E. coli* cell lysates revealed that $Cys^{233}$ of the Fd were responsible for heavy degradation and no secretion of the Fd fragments probably due to protein aggregation. The yield of HcysG/Lcys was 0.5 µg/ml, and those of HserG/Lcys and LserG/Hser were approximately 1.8 µg/ml and 1.4 µg/ml, respcectively(FIG. 5A). Interestingly, the yield of HserG/Lser was about 4 µg/ml which was eight-fold higher than that of HcysG/Lcys. The periplasmic extracts showed the identical expression pattern, although the total yields were only ~30% to those present in the culture supernatant (data not shown). In the repeated experiments, it was confirmed that the difference in the yields between HcysG/Lcys and HserG/Lser was independent of the clonal variation or growth rate of the *E. coli* clones. The binding reactivity of SL335-hGH fusions to HSA were compared using the microtiter plates coated with 5 µg/ml HSA, and incubated with the serial dilutions of the culture supernatant containing SL335-hGH fusions. SL335-hGH fusions bound to HSA were then detected using the goat anti-human kappa L chain pAb conjugated with HRPO. As expected, the detection of HserG/Lser that bound to HSA with the anti-human κL pAb produced an eight-fold stronger binding signal than that of HcysG/Lcys and approximately four-fold stronger binding signal than those of HserG/Lcys and LserG/Hser (FIG. 5B). Similar binding signal patterns were also observed when T-20, a goat pAb specific for the C-terminus of the hGH was used to detect the SL335-hGH fusions (FIG. 5C). In the detection with NYThGH, a mouse mAb specific for full-length hGH, however, HserG/Lser produced a 30-fold higher binding signal than those of both HserG/Lcys and LserG/Hser and 60-fold higher binding signal than that of HcysG/Lcys (FIG. 5D), suggesting that the binding of NYThGH to the hGH domain of HcysG/Lcys was interfered by the presence of the interchain disulfide bond in SL335. Since HcysG/Lcys and HserG/Lser represent the utilization of $SL335_{wt}$ and $SL335_{Ads}$ for creating the SL335-hGH fusions, they were named as $SL335_{wt}$-hGH fusion and $SL335_{Ads}$-hGH fusion, respectively, hereafter (FIG. 5).

Figure 6A:
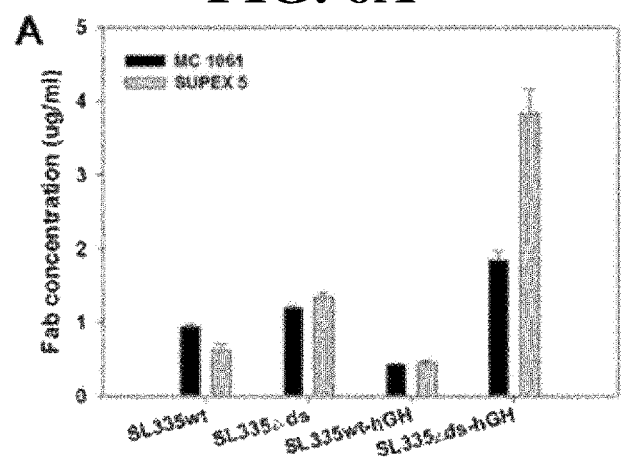
FIGS. 6A through 6C represents the ELISA to determine host E. coli- and temperature-dependent expression of SL335 and SL335-hGH variants at 20° C.
Figure 6B:
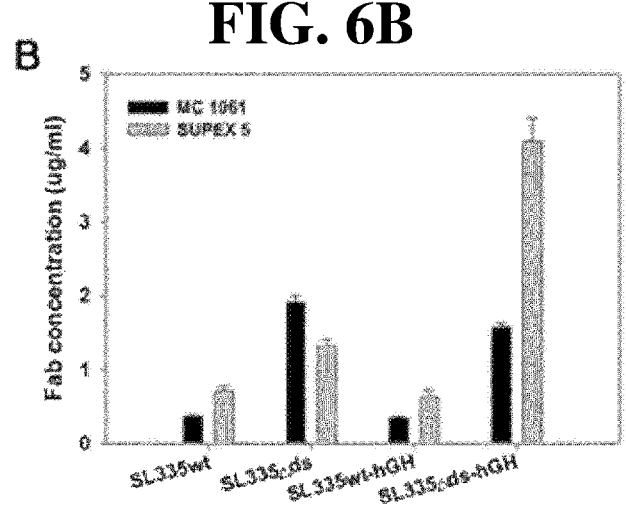
Figure 6C:
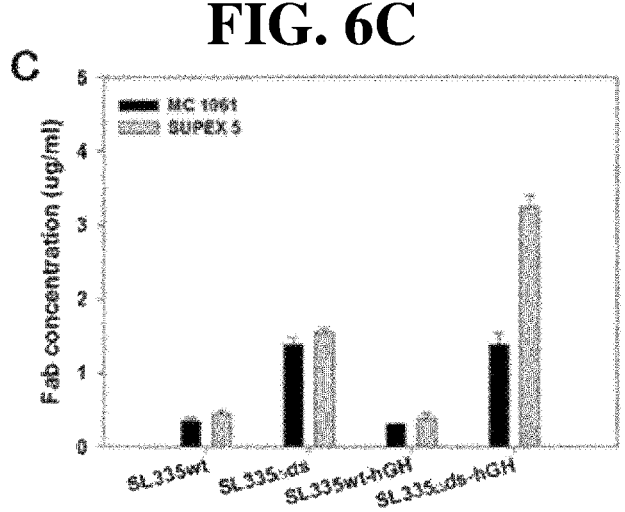

To determine the high yield of soluble $SL335_{Ads}$-hGH fusion was dependent upon removal of the interchain disulfide bond in SL335, host *E. coli* strains or induction temperature, $SL335_{wt}$, $SL335_{Ads}$, $SL335_{wt}$-hGH fusion and $SL335_{Ads}$-hGH fusion were expressed in the parental MC1061 as well as the mutant SUPEX5 cells at 20° C. (FIG. 6A), 25° C. (FIG. 6B) or 30° C. (FIG. 6C) and the amount of Fab molecules in the culture supernatant was measured by ELISA. The yield of $SL335_{wt}$ expressed in the MC1061 strain was 1 µg/ml at 20° C., which was about three-fold higher than that at 25° C. and 30° C. This implied induction of $SL335_{wt}$ below 25° C. is advantageous especially when MC1061 was used as a host strain. Similar results were also obtained with the SUPEX5 strain. In the case of $SL335_{Ads}$, the yield was about 1.3 µg/ml at 20° C. regardless of the host *E. coli* strains and induction temperature. These results indicated that the presence or absence of the interchain disulfide bond in a Fab did not significantly influence the yield of soluble Fab production at 20° C. regardless of the *E. coli* host strains. The yield of $SL335_{wt}$-GH fusion was about 0.3-0.5 µg/ml regardless of the host *E. coli* strains and induction temperature. On the other hand, the yield of $SL335_{Ads}$-hGH fusion expressed in the MC1061 strain was 1.8 µg/ml at both 20° C. and 25° C., and 1.5 µg/ml at 30° C., showing minor temperature-dependency, whereas, the yield of $SL335_{Ads}$-hGH fusion expressed in the SUPEX5 strain was 4.0 µg/ml at both 20° C. and 25° C., and 3.5 µg/ml at 30° C. These results meant that utilization of the $SL335_{Ads}$ form and the *E. coli* SUPEX5 strain enabled about 12-fold higher yield of the SL335-hGH fusion protein compared to the combination of the $SL335_{wt}$ form and the *E. coli* MC1061 strain.

Figure 7A:
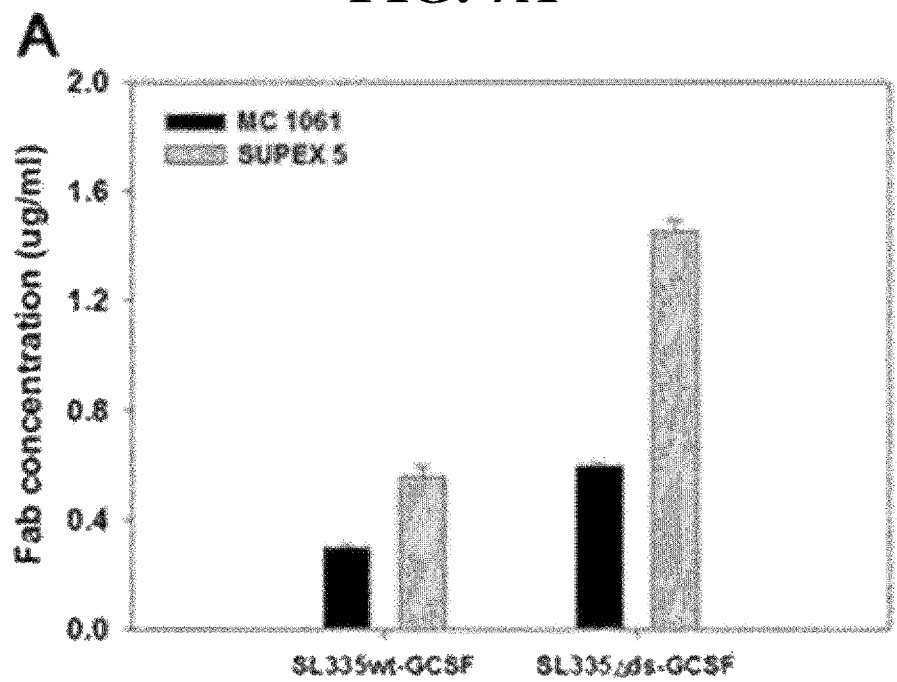
FIGS. 7A and 7B represent the ELISA to determine the yields of soluble SL335-GCSF (FIG. 7A) and SL335-IFNβ (FIG. 7B) fusion constructs in the E. coli culture supernatant.
Figure 7B:
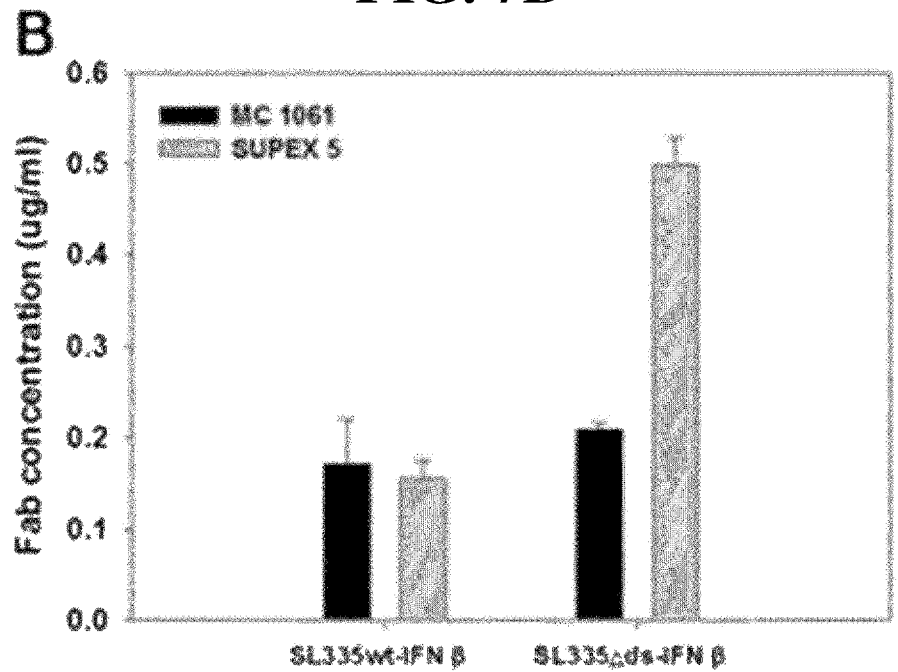

2-(5) Generation of the SL335-GCSF, SL335-IFNb, EGL4-hGH and 1b28-hGH Fusion Constructs To demonstrate the beneficial effect of a $Fab_{Ads}$ form and the SUPEX5 strain on improving soluble expression of a Fab-effector fusion protein, diverse Fab-effector fusioncon structs were generated. First, two SL335-GCSF fusion variants (HcysGCSF/Lcys that termed as $SL335_{wt}$-GCSF, HserGF/Lser that termed as $SL335_{Ads}$-GCSF) and two SL335-IFNb fusion variants (HcysIFNb/Lcys that termed as $SL335_{wt}$-IFNb, HserlFNb/Lser that termed as $SL335_{Ads}$-IFNb) were created as the same way as generating $SL335_{wt}$-hGH and $SL335_{Ads}$-hGH fusions to determine the influence of an effector domain. Induction temperature was set to optimal 20° C. and the expression yields of these fusion proteins in the *E. coli* culture supernatant were compared by ELISA. The yields of $SL335_{wt}$-GCSF were 0.3 and 0.6 mg/ml in MC1061 and SUPEX5, respectively, and those of $SL335_{Ads}$-GCSF were 0.6 and 1.5 mg/ml in MC1061 and SUPEX5, respectively (FIG. 7A). Whereas, the yield of $SL335_{wt}$-IFNb was approximately 0.16 mg/ml in both MC1061 and SUPEX5, and those of $SL335_{Ads}$-IFNb were 0.2 and 0.5 mg/ml in MC1061 and SUPEX5, respectively (FIG. 7B). Therefore, the combination of $SL335_{Ads}$-GCSF fusion and SUPEX5 strain produced about 5-fold higher yield of a SL335-GCSF fusion form compared to the combination of SL335$_{wt}$-GCSF fusion and the MC1061 strain, and the combination of SL335$_{Ads}$-IFNb fusion and SUPEX5 strain produced about 3-fold higher amount of a SL335-IFNb fusion form compared to the combination of SL335$_{wt}$-IFNb fusion and the MC1061 strain. Second, we also created two Fab-hGH fusion constructs using EGL4, a human anti-EFGR Fab, and 1b28, a human anti-IL-1b Fab to determine the influence of a Fab. As the same way as generating SL335$_{wt}$-hGH and SL335$_{Ads}$-hGH fusions, the two EGL4-hGH fusion constructs were EGL4$_{wt}$-hGH fusion in the HcysG/Lcys format and EGL4$_{Ads}$-hGH fusion in the HserG/Lser format. Likewise, the 1b284-hGH fusion constructs were 1b28$_{wt}$-hGH fusion in the HcysG/Lcys format and 1b28$_{Ads}$-hGH fusion in the HserG/Lser format. The yield of EGL4$_{wt}$-hGH fusion was 8090 ng/ml in the MC1061 and SUPEX5 strains, and the yields of EGL4$_{Ads}$-hGH fusion were 140 ng/ml in the MC1061 strain and 220 ng/ml in the SUPEX5, strain (FIG. 8A), indicating that the combination of EGL4$_{Ads}$-hGH fusion and the SUPEX5, host cell produced 2.4-fold higher amount of a EGL4-hGH fusion protein in the culture supernatant compared to the combination of EGL4$_{wt}$-hGH fusion and the MC1061 host cell. In the case of the 1b28-hGH fusion constructs, the yield of 1b284$_{wt}$-hGH fusion was 50 ng/ml in the MC1061 and 100 ng/ml SUPEX5 strains, respectively, and the yields of 1b28$_{Ads}$-hGH fusion were 900 ng/ml in the MC1061 strain and 4 mg/ml in the SUPEX5 strain (FIG. 8B), indicating that the combination of 1b28$_{Ads}$-hGH fusion and the SUPEX5 host cell produced 800-fold higher amount of a 1b28-hGH fusion form in the culture supernatant compared to the combination of 1b28$_{wt}$-hGH fusion and the MC1061 host cell.

2-(6) Molecular Characterization of SL335wt-hGH and SL335$_{Ads}$-hGH

SL335$_{wt}$-hGH and SL335$_{Ads}$-hGH fusions were further characterized at the molecular level. The fusion proteins in the culture supernatant were affinity-purified by passing through the resins coated with HSA, and analyzed by SDS-PAGE and western blot under the reducing and non-reducing conditions. HcysG/Lcys (lane 1) and HserG/Lser (lane 2) were affinity-purified from the culture supernatnat with HSA-immobilized sepharose beads, and SDS-PAGE was carried out using 4-12% Bis-Tris gel under the reducing or non-reducing condition. Protein bands were visualized with Coomassie Blue staining (FIG. 9A). The proteins of the separate SDS-PAGE were transferred to nitrocellulose membrane, and the goat anti-human kappa L Ab-conjugated with AP was used to detect Lcys and Lser (FIG. 9B). The binding signals were visualized with a NBT/BCIP substrate. In SDS-PAGE analysis, both SL335$_{wt}$-hGH and SL335$_{Ads}$-hGH produced two major protein bands at 46kDa and 23kDa in size which correspond to the Fd-hGH fusions and the L chains, respectively, under the reducing conditions. Under the non-reducing conditions, SL335$_{Ads}$-hGH expectedly produced two identical protein bands due to the absence of an interchain disulfidebond. In the case of SL335$_{wt}$-hGH, a major 70 kD a protein band which corresponds to a correct heterodimeric form of SL335$_{wt}$-hGH was visible. Yet, many different size of SL335$_{wt}$-hGH derivatives were also found, including four obvious protein bands ranging from 24 kDa to 45 kDa of unknown identity and a couple of weak protein bands corresponding to 100 kDa and 135 kDa in size. The proteins at 15 kDa and 12.5 kDa in size were also visible from all of the samples. Western blot analysis was then performed using an anti-human Fd mAb, the anti-kappa L chain pAb and the anti-hGH pAb, T-20. The blot with the anti-human Fd mAb detected only HcysG and HserG of 46 kDa in size under both non-reducing and reducing conditions (data not shown). On the other hand, four proteins bands ranging from 24 kDa to 45 kDa as well as those larger than 70 kDa in the SL335$_{wt}$-hGH sample were all detected by the anti-kappa L chain pAb under the non-reducing condition (FIG. 9B). This result indicated that Cys$^{214}$ of the L chain is responsible for the formation of the diverse multimeric L chains, at least, via aberrant disulfide bond formations. The blot with T-20 anti-hGH pAb correctly recognized the 70 kDa heterodimeric form of SL335$_{wt}$-hGH and the ~45 kDa monomeric HerG of SL335$_{Ads}$-hGH under the non-reducing condition (FIG. 9C). The proteins at 15 kDa and 12.5 kDa in size were not detected by any of those antibodies, suggesting that they were either the degraded products from the fusions or the contaminants from E. coli host proteins.

Figure 10A:
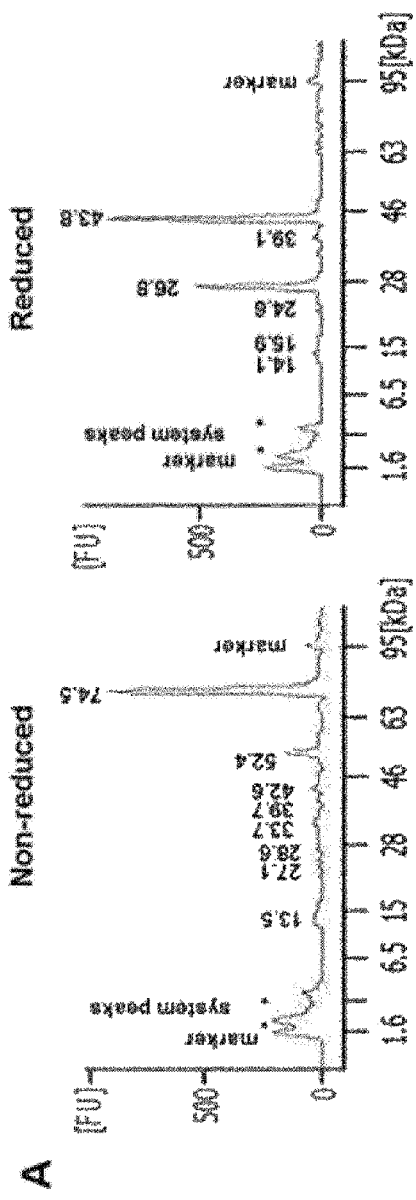
FIGS. 10A and 10B represent the analyses of HcycG/Lcys (FIG. 10A) and HserG/Lser (FIG. 10B) by Chip-based capillary electrophoresis.
Figure 10B:
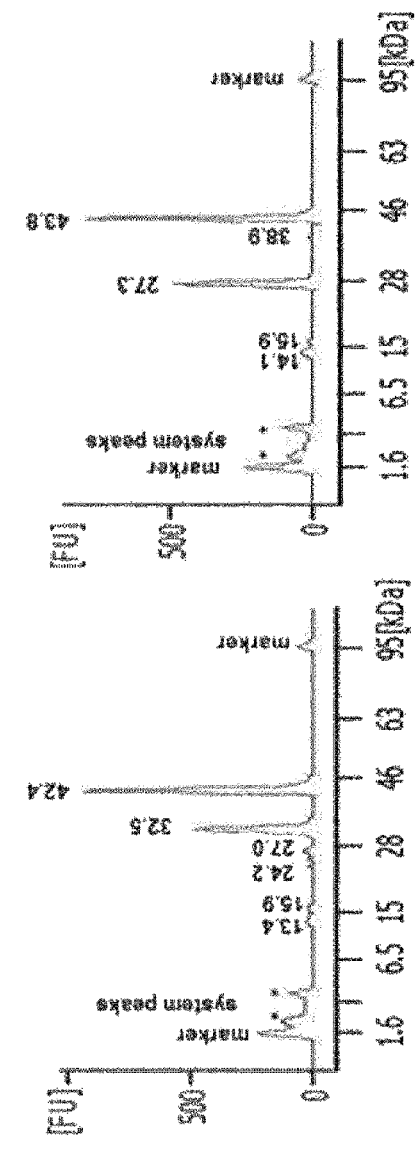

A chip-based capillary electrophoresis confirmed the SDS-PAGE analysis. HcysG/Lcys (FIG. 10A) and HserG/Lser (FIG. 10B) were prepared with sample buffer in the presence or absence of DTT for reducing or non-reducing electrophoresis, and chip-based capillary electrophoresis was carried out with the Agilent 2100 Bioanalyzer system according to the manufacturers protocol using the Protein 80 kit. The results were plotted to reflect fluorescence intensity units against protein size. SL335$_{wt}$-hGH produced several SL335$_{wt}$-hGH derivatives ranging from 27.1 kDa to 52.4 kDa in size under the non-reducing condition, and many of them disappeared under the reducing condition in the presence of DTT (FIG. 10A). SL335$_{Ads}$-hGH produced almost identical protein peaks between the non-reducing and reducing conditions except for minor changes in molecular weights (FIG. 10B).

Figure 8A:
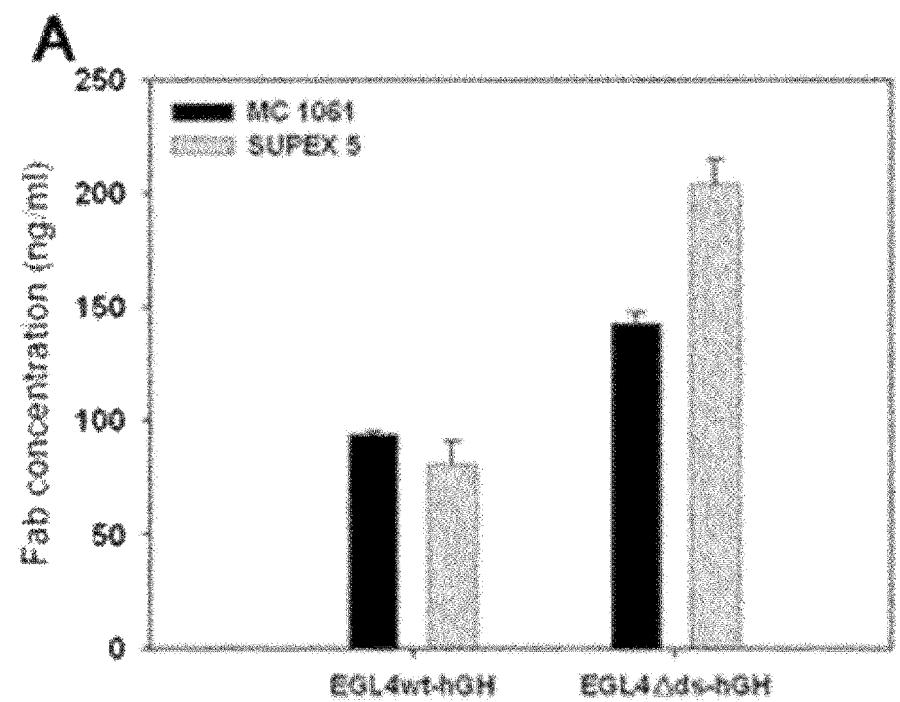
FIGS. 8A and 8B represent the ELISA to determine the yields of soluble EGL4-hGH (FIG. 8A), and 1β28-hGH fusions (FIG. 8B) in E. coli culture supernatant.
Figure 8B:
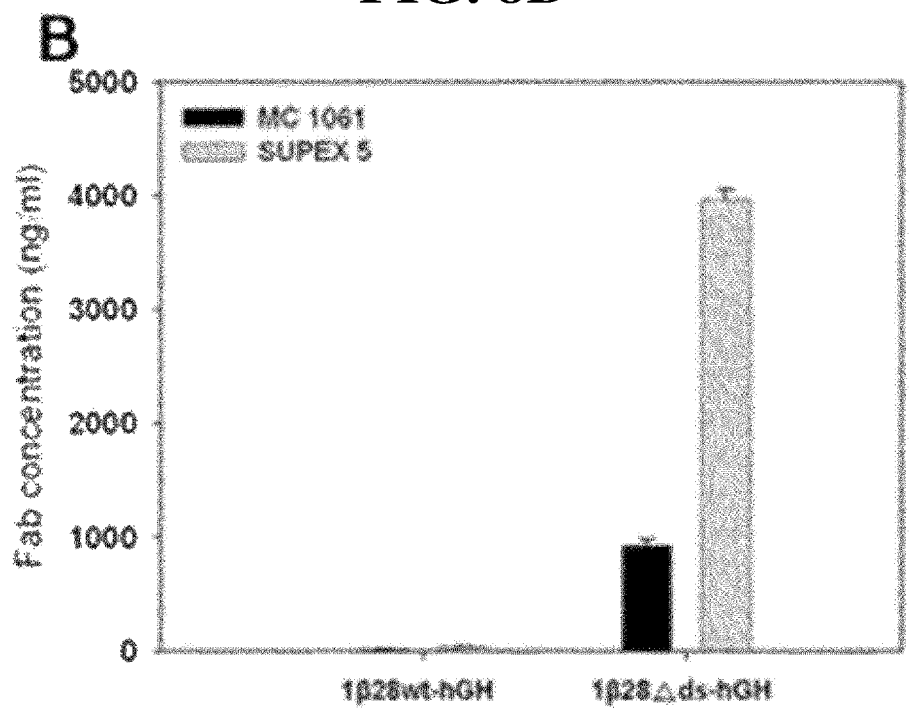
Figure 11A:
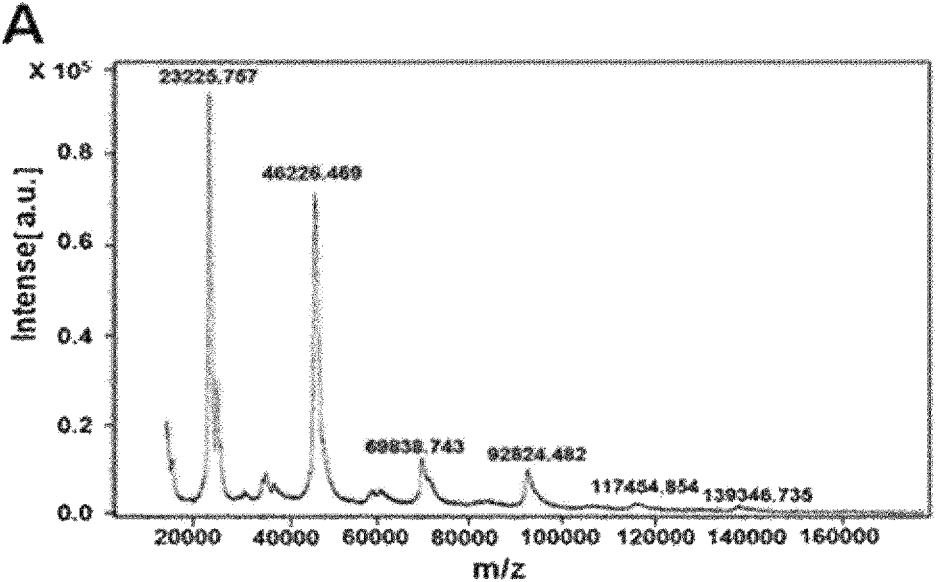
FIGS. 11A and 11B represent the analysis of HcycG/Lcys (FIG. 11A) and HserG/Lser (FIG. 11B) by MALDI-TOF mass spectrometry.
Figure 11B:
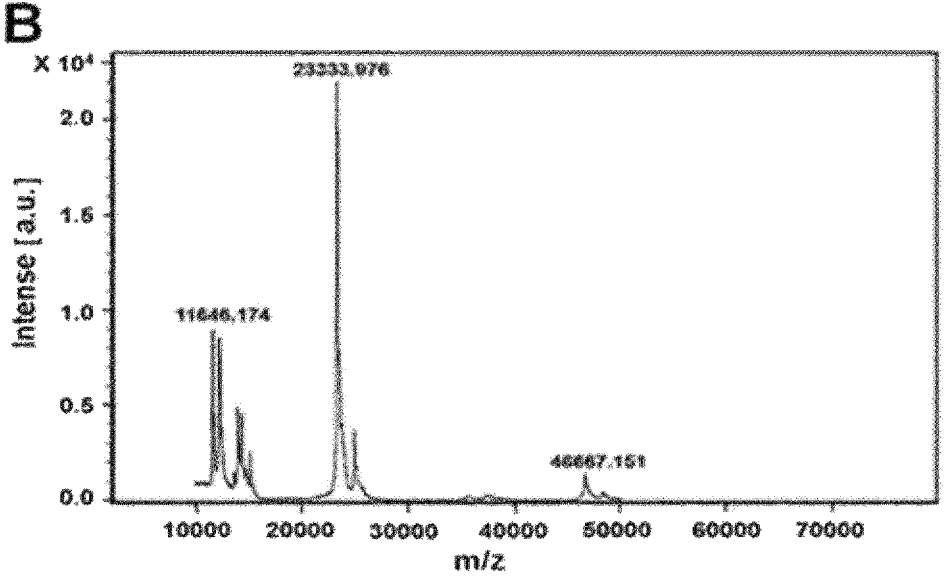

SL335$_{wt}$-hGH and SL335$_{Ads}$-hGH were further analyzed using MALDI-TOF mass spectrometry. MALDI-TOF mass spectrometry was performed on an Autoflex III Smartbeam device (Bruker Daltonics, Billerica, Mass., USA). Affinity-purified HcysG/Lcys (FIG. 11A) and HserG/Lser (FIG. 11B) were mixed with the MALDI matrix, and spectra were acquired over the m/z range 10000-150000 Da in the positive ion mode. Mass spectra in the m/z range of 10000-70000 were acquired for SL335$_{Ads}$-hGH. For SL335$_{wt}$-hGH, those of 15000-160000 were obtained because the SL335$_{wt}$-hGH sample showed the protein bands larger than 70 kDa as shown in FIG. 8A. Molecular masses of Lcys, HcysG and SL335$_{wt}$-hGH were identified as 23,226 Da, 46226 Da and 69,837 Da, respectively (FIG. 11A). The size of three discrete proteins those are bigger than the correct SL335$_{wt}$-hGH were found to be 92,824 Da, 117,455 Da and 139,347 Da. In the case of SL335$_{Ads}$-hGH, molecular masses of Lser and HserG were identified as 23,334 Da and 46,667 Da, respectively (FIG. 11B). The low peak of HserG compared to Lser might represent lower ionizing efficiency of larger molecules, or the presence of lower molar ratio of HserG than Lser in the sample.

Figure 12A:
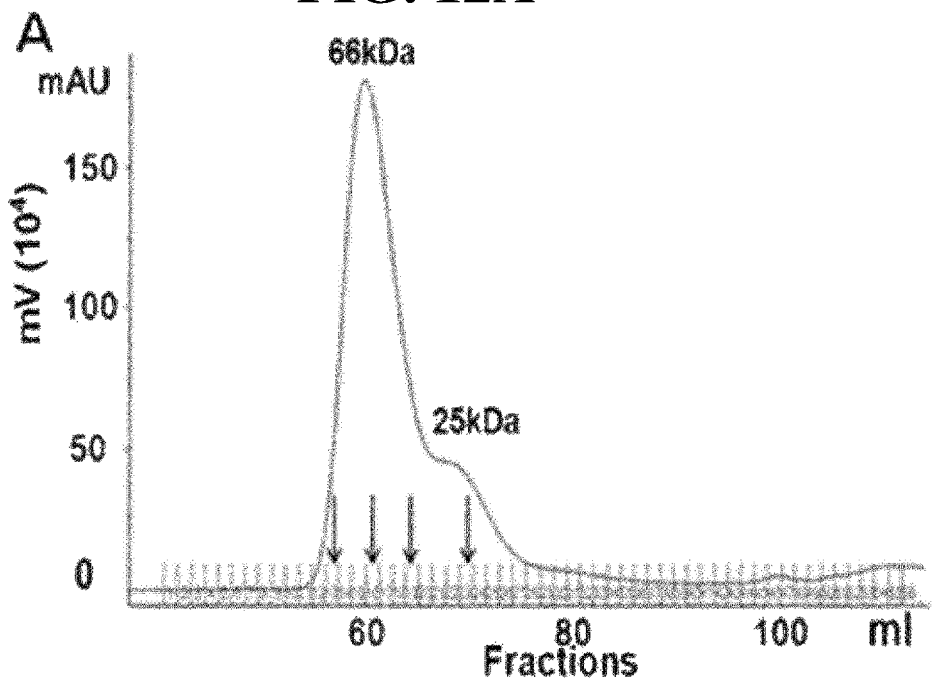
FIGS. 12A and 12B represent the purification of HserG/Lser via gel filtration using FPLC.
Figure 12B:
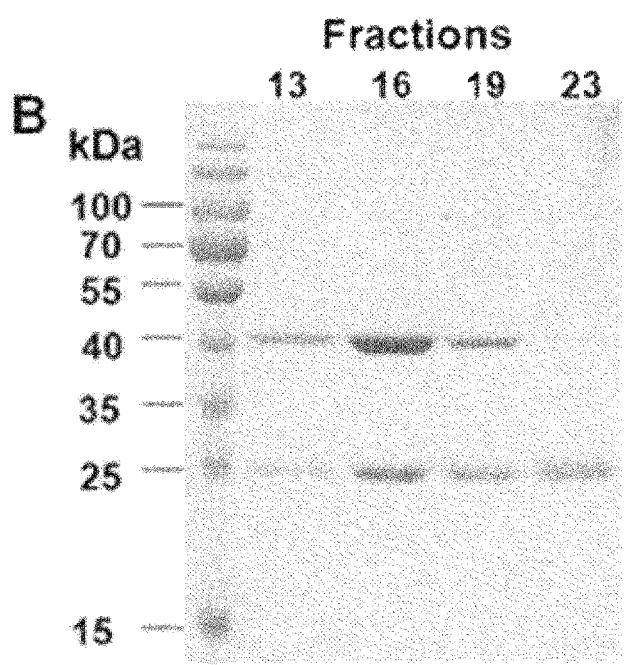

Affinity-purified SL335$_{Ads}$-hGH was further purified by passing through SephacrylS-200HR column using FPLC. Gel filtration of HserG/Lser was performed after affinity purification using Sephacryl™ S-200HR Prepacked Column and AKTA FPLC (GE Healthcare, Wauwatosa, Wis., USA). The column was equilibrated with equilibration buffer (20 mM HEPES pH 7.4 containing 150 mM NaCl), and loaded with affinity-purified HserG/Lser. Elution was performed with equilibration buffer at 0.5 ml/min running flow rate. Arrows indicate the fractions chosen for SDS-PAGE analysis (FIG. 12A). Fraction #13, #16, #19 and #23 that retrieved from two distinctive peaks were analyzed by 4-12% Bis-Tris gel under the reducing condition (FIG. 12B). Protein bands were visualized with Coomassie Blue staining. Two peaks that correspond to approximately 66 kDa and 25 kDa were visible from the fraction #12 to #27 (FIG. 9A). Thence, four fractions (fraction #13, #16, #19 and #23) were analyzed by SDS-PAGE under the reducing condition to determine protein contents in the fractions (FIG. 9B). The results showed that the fractions from the 66 kDa peak (fraction #13, #16 and #19) contained the heterodimeric SL335$_{Ads}$-hGH, and the fraction from the 25 kDa peak (fraction #23) mainly contained the monomeric Lser.

2-(7) In vitro Functional Characterization of SL335Δds-hGH

To determine whether removal of an interchain disulfide bond in SL335$_{wt}$ and the fusion of the hGH affect binding affinities to HSA or RSA, a biolayer interferometry assay was performed using SL335$_{Ads}$-hGH under pH 6 and pH 7.4 conditions (see the Table 6 below). The dissociation constants of SL335$_{Ads}$-hGH to HSA were 1.7 nM at pH 6 and 1.5 nM at pH 7.4, showing a five-fold and an 8.7-fold increase of affinity compared to those of SL335, respectively. The dissociation constants to RSA were 499 nM and 83.6 nM under pH 6 and pH 7.4, showing a 4.2-fold and a 1.3-fold decrease of affinity compared with those of SL335, respectively.

Figure 13A:
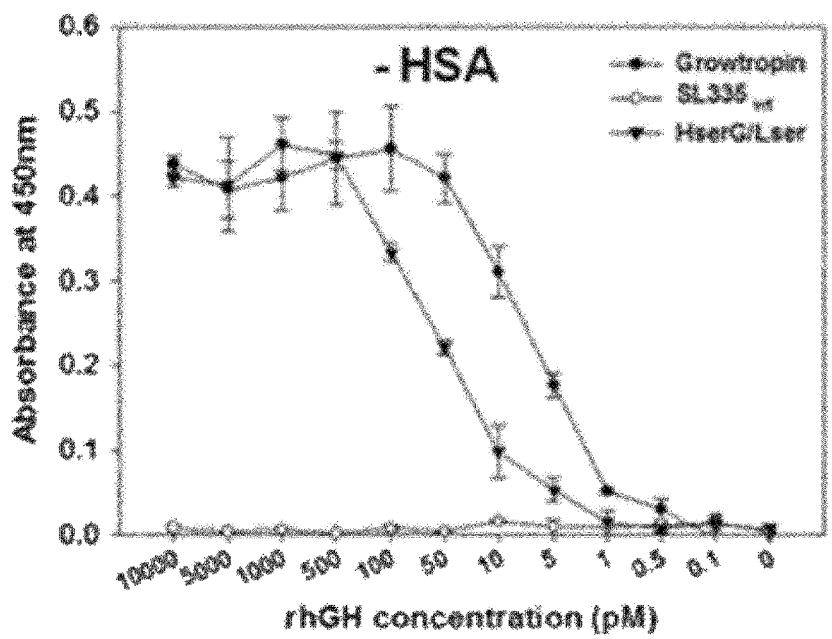
FIGS. 13A and 13B shows the determination of the in vitro hGH bioactivity of SL335$_{ds}$-hGH by the Nb2-11 cell proliferation assay without HSA (FIG. 13A) and with HSA (FIG. 13B).
Figure 13B:
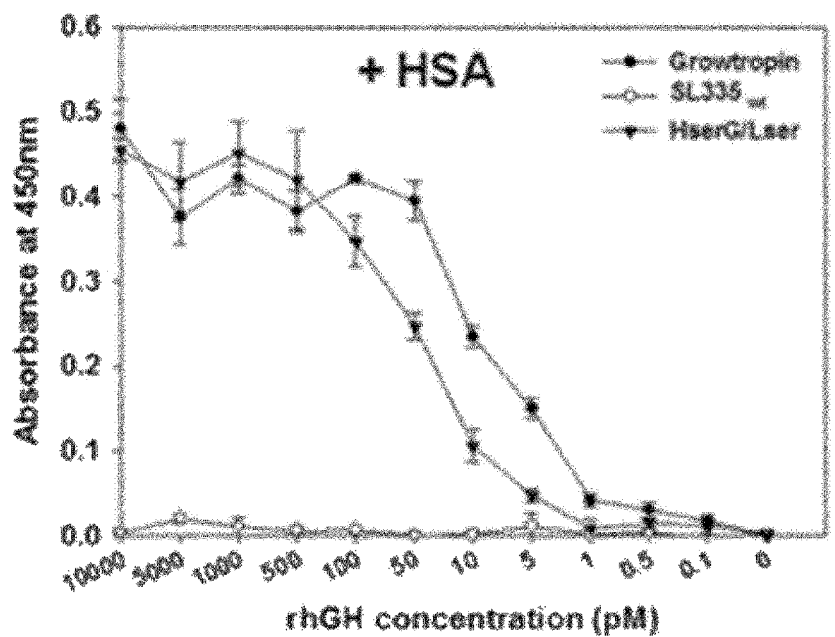

The in vitro hGH activity of SL335$_{ds}$-hGH was also measured using the Nb2-11 rat lymphoma cells that proliferate upon hGH treatment in a concentration-dependent manner. Nb2-11 rat lymphoma cells were resuspended in DMEM containing 5% (v/v) horse serum at 8×10$^4$ cells/ml, and a 50 µl aliquot of the cell suspension was added into each well of the 96-well plates, followed by overnight incubation. The cells were then treated with increasing concentrations of Growtropin® or HserG/Lser (0-20 nM) in 50 ml DMEM containing 5% horse serum for 48 h at 37° C. Following incubation, 10 ji of CCK-8 solution was added to each well, and cells were incubated for 4 h. The absorbance was recorded on a microplate reader at a wavelength of 450 nm. The data represent the average SD of three experiments. In the absence of HSA, SL335$_{Ads}$-hGH was able to stimulate the growth of Nb2-11 with an apparent EC$_{50}$ of 50 pM (3.5 ng/ml) (FIG. 13A). This value is 6.7-fold less potent than that of Growtropin®, the rhGH standard (7.5 pM). In the presence of 10 mM HSA, the respective potencies of Growtropin® and SL335$_{Ads}$-hGHwere largely unaffected, although SL335$_{Ads}$-hGH represented an approximately five-fold reduction in potency compared to that of Growtropin® (FIG. 13B). SL335 that was used as a negative control did not show any proliferative effect. These results clearly demonstrated a functional hGH bioactivity of SL335$_{Ads}$-hGH.

Figure 14A:
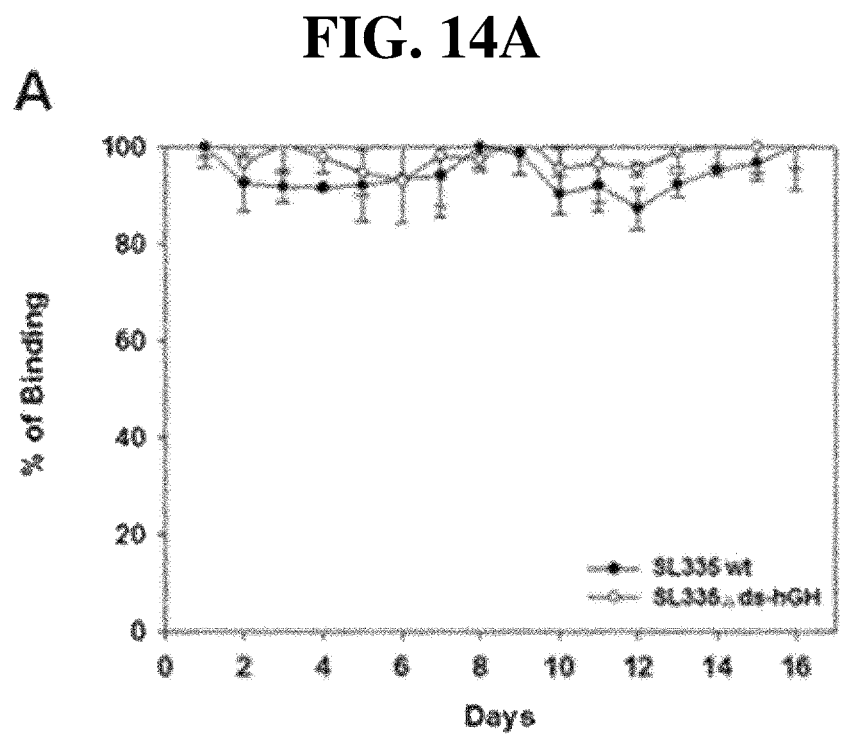
FIGS. 14A and 14B show the determination of serum stability of SL335$_{ds}$-hGH by ELISA (FIG. 14A) and in vitro Nb2-11 cell proliferation assay (FIG. 14B).
Figure 14B:
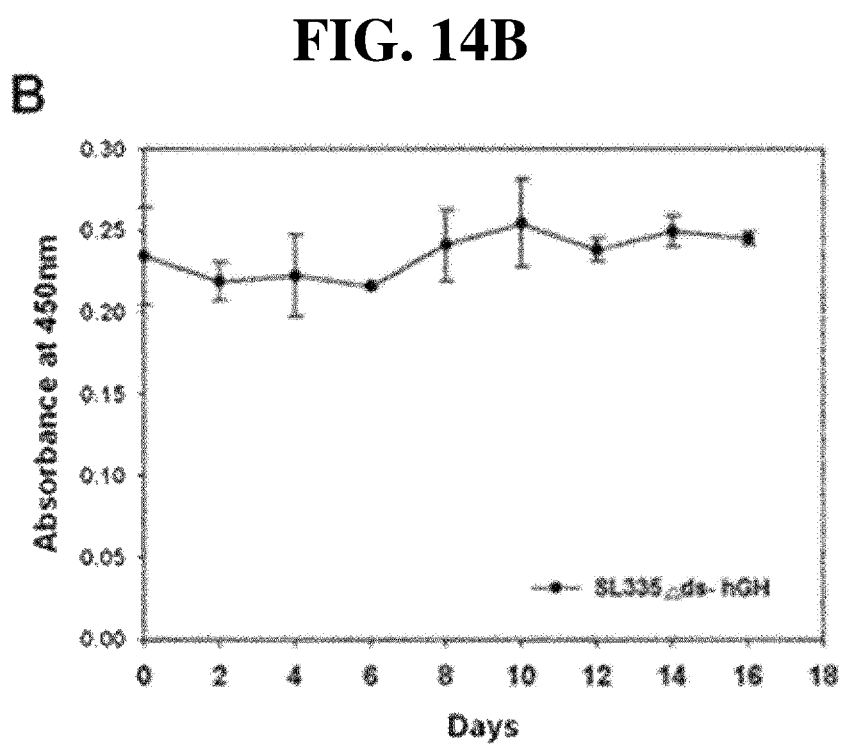

The serum stability was then determined by incubating SL335$_{Ads}$-hGH at 37° C. for 16 days. FBS was used instead of human serum for resuspending the samples because the binding capabilities of SL335$_{Ads}$-hGH and SL335 to HSA in human serum would complicate the subsequent experiments. Samples were collected once a day, and the HSA-binding reactivity and in vitro bioactivity were measured by ELISA (FIG. 14A) and the Nb2-11 cell proliferation assay (FIG. 14B), respectively. SL335 was also included as a control. Similar to SL335, the binding reactivity to HSA and the Nb2-11 proliferative activity of SL335$_{Ads}$-hGH did not change even after 16 days of incubation at 37° C., demonstrating that SL335$_{Ads}$-hGH is as stable as SL335 despite the absence of the interchain disulfide bond.

2-(8) Pharmacokinetics and Pharmacodynamics Studies in Rats

Figure 15A:
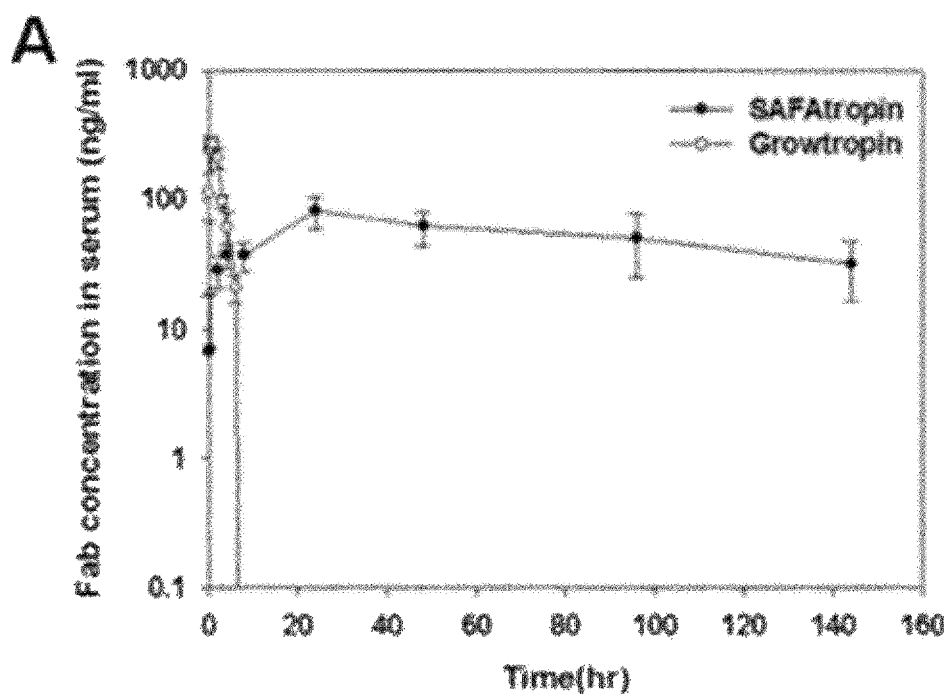
FIGS. 15A and 15B are the pharmacokinetic analysis of Growtropin or SL335$_{ds}$-hGH in rats by subcutaneous injection (FIG. 15A) and by intravenous injection (FIG. 15B).
Figure 15B:
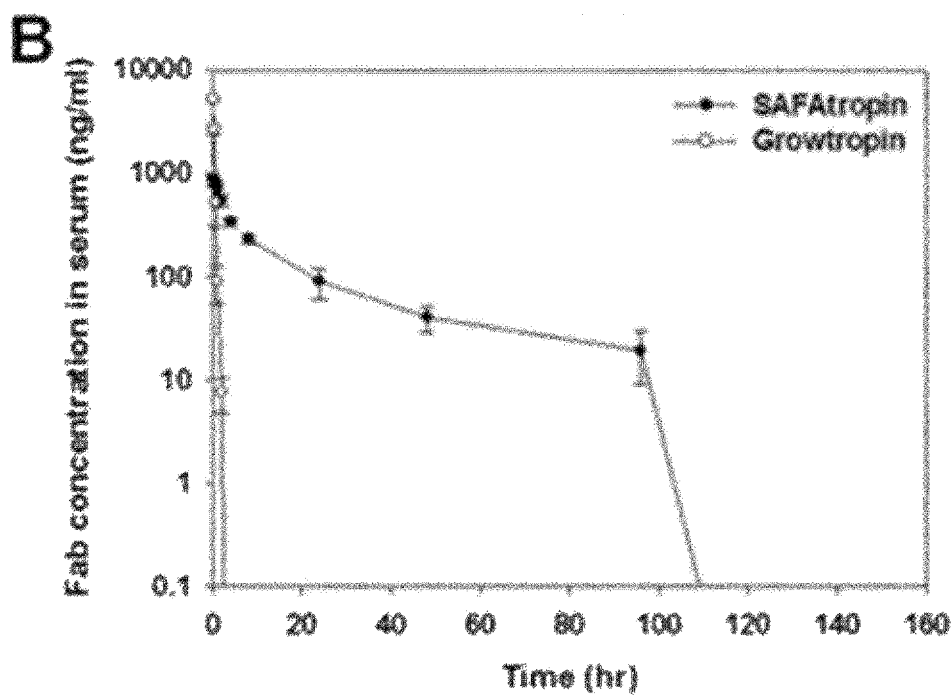

Because SL335$_{Ads}$-hGH was shown to be a promising candidate for a long-acting hGH, in vivo efficacy studies were performed. Firstly, the pharmacokinetics of Growtropin® and SL335$_{Ads}$-hGH were compared in rats by measuring serum levels of each analog as a function of time after a single intravenous or subcutaneous injection. Each group of rats (four in a group) was given subcutaneous injection (FIG. 15A) of a single bolus dose of 0.6 mg/kg of Growtropin or SAFAtropin, or intravenous injection (FIG. 15B) of a single bolus dose of 0.3 mg/kg of Growtropin or SAFAtropin. Serum samples were taken over intervals extending to 144h depending upon the protein. Serum samples were analyzed at indicated times for Growtropin® or SAFAtropin® by an ELISA as described above. The pharmacokinetic parameters are shown in Table 7.

TABLE 7

Pharmacokinetic parameters in rats given a single intravenous or subcutaneous injection of Growtropin or SAFAtropin

| | | $t_{1/2}$ (h) | Cmax (ng/ml) | AUC$_{0→∞}$ (h ng/ml) | Cl/f (ml/hr/kg) |
|---|---|---|---|---|---|
| I.V. | Growtropin | 0.23 ± 0.05 | 5168.69 ± 61.32 | 1759.97 ± 145.03 | 171.04 ± 13.66 |
| | SAFAtropin | 16.6 ± 1.5 | 882.2 ± 81.8 | 19580.3 ± 999.3 | 15.34 ± 0.76 |
| S.C. | Growtropin | 1.35 ± 0.13 | 283.42 ± 28.84 | 821.8 ± 52.56 | 714.79 ± 45.63 |
| | SAFAtropin | 97.16 ± 30.86 | 83.2 ± 23.12 | 7689.4 ± 2640.71 | 56.11 ± 25.39 |

Values shown are averages standard deviation. Abbreviations are as follow: Cmax: maximum concentration; $t_{1/2}$: terminal half-life; AUC$_{0→∞}$: area under the concentration-time curve extrapolated to infinity; Cl/f: apparent total plasma clearance.

SL335$_{Ads}$-hGH showed dramatically extension of the $t_{1/2}$ irrespective of the route of administration. In intravenous administration, SL335$_{Ads}$-hGH represented an 83-fold increase in the $t_{1/2}$ compared to Growtropin (16.6 h vs. 0.2 h) and a 69-fold increase in the subcutaneous administration (97.2 h vs. 1.4 h).

SL335$_{Ads}$-hGH also exhibited a ~10-fold increase in AUC$_{0→∞}$ and a more than 10-fold slower clearance rate (Cl/f) compared to those of Growtropin® regardless of the route of administration. Each group of rats (four in a group) was given subcutaneous injection of a single bolus dose of 0.6 mg/kg of Growtropin or SAFAtropin, or intravenous injection of a single bolus dose of 0.3 mg/kg of Growtropin or SAFAtropin. Serum samples were taken over intervals extending to 144 h depending upon the protein. Serum samples were analyzed at indicated times for Growtropin® or SAFAtropin® by an ELISA as described above. Interestingly, the $C_{max}$ values of SL335$_{Ads}$-hGH were 6-fold and 3-fold lower than those of Growtropin® depending on the route of administration.

Figure 16:
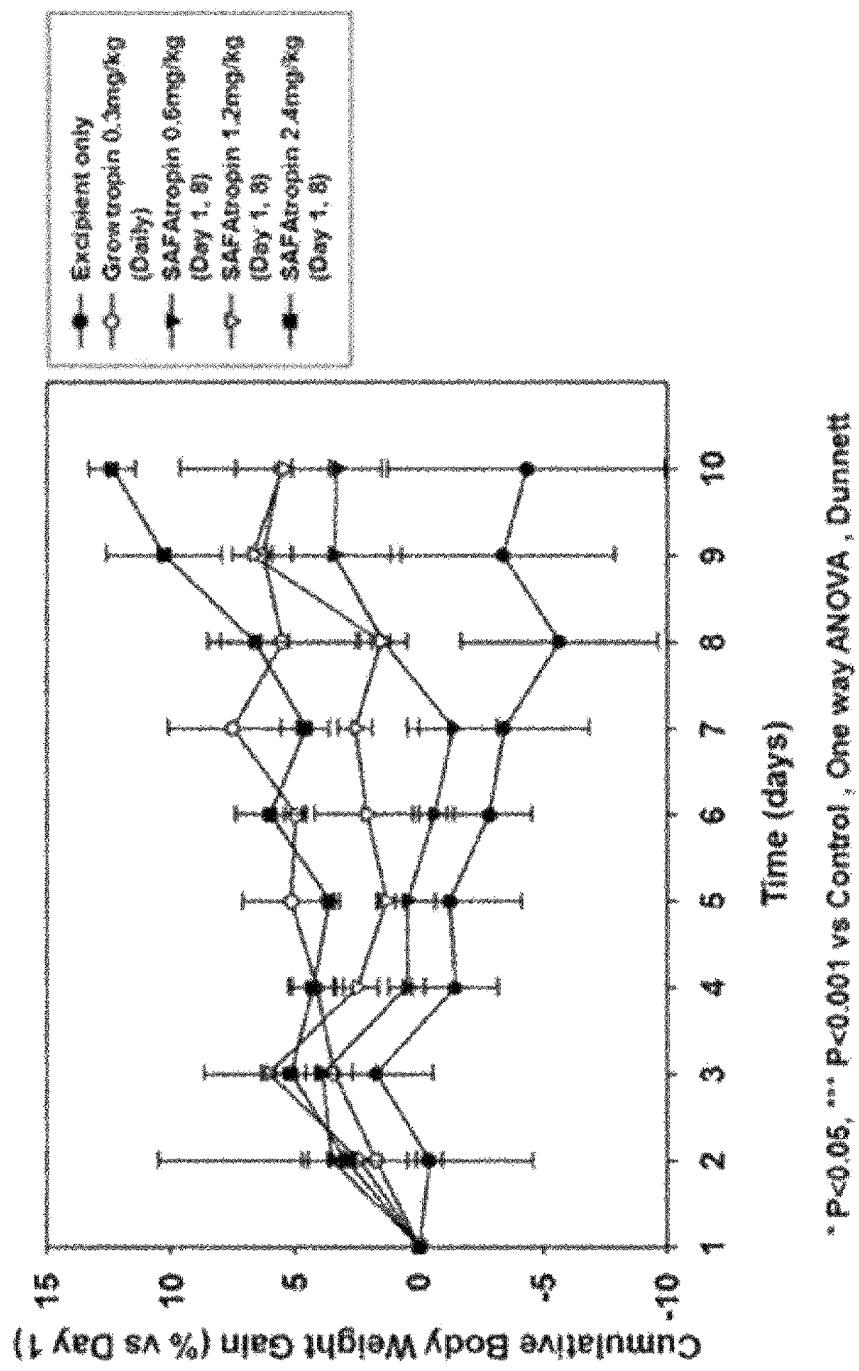
FIG. 16 shows the dose-dependent weight gain in hypophysectomized rats treated with Growtropin® or SL335$_{Ads}$-hGH. N=3 rats per treatment group, one daily weight measurement per rat.

Next, the growth rates of hypophysectomized rats were compared over ten days after daily S.C. administration of Growtropin® or an excipient buffer control (Excipient only), or once-weekly S.C. administration of SL335$_{ds}$-hGH. Hypophysectomized rats were treated with Excipient only or 0.3 mg/kg Growtropin® daily, or with increasing dose of SAFAtropin® on days 0 and 7 (FIG. 16). Solid lines indicate the mean percentage change in body weight. Error bars represent standard deviation. The excipient-treated rats showed an approximately 5% weightloss. Whereas, those receiving daily injection of Growtropin® (0.3 mg/kg) showed a 5% weight gain, resulting in a total 10% weight gain over the Excipient Only group. Once-weekly injections of SL335$_{\Delta ds}$-hGH produced dose-dependent weight gains in that the 2.4 mg/kg dosage produced a 15% weight gain, and the 0.6 mg/kg dosage produced a 3.5% weight gain. An equimolar SL335$_{\Delta ds}$-hGH (1.2 mg/kg) dosage regimen resulted in a 5% weight gain which was comparable to that obtained by daily injections of Growtropin®.

Figure 17:
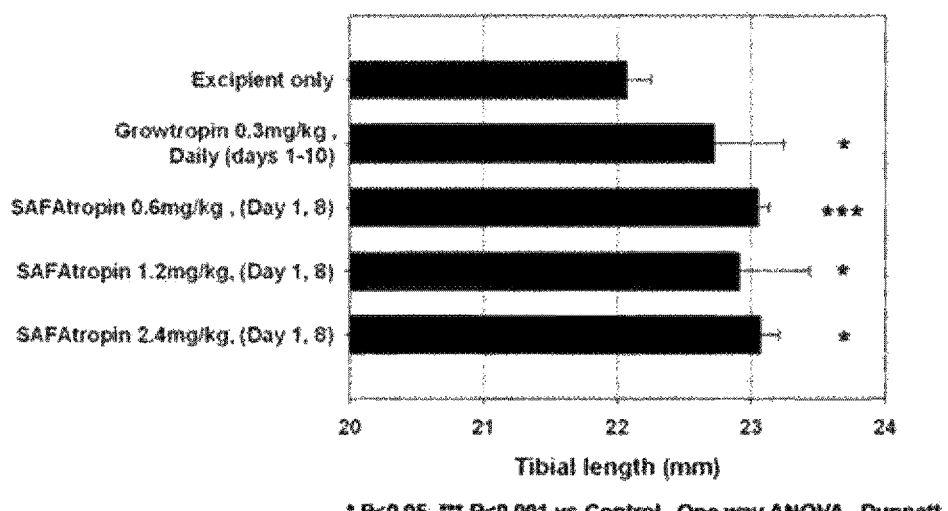
FIG. 17 shows the dose-dependent increase in tibia length with treated Growtropin® or SL335$_{Ads}$-hGH. N=3-4 rats per treatment group, one tibia measurement per rat.

FIG. 17 shows that the once-weekly administration of 0.6 mg/kg SL335$_{\Delta ds}$-hGH achieved equivalent increases in tibia length as those achieved by the daily administration of Growtropin®. Solid bars indicate the mean of measured tibia bone length. Error bars represent standard deviation.

The present invention would be used to develop bioactive protein or polypeptide therapeutic agents, since the fusion constructs of the invention can be prepared to comprise various types of effector moieties including human growth hormone, interferon, erythropoietin, colony stimulating factors or derivaties therof, and antibody derivatives, etc.

The teachings of all patents, published applications and references cited herein are incorporated by reference in their entirety.

The invention claimed is:

1. A method of increasing soluble expression of a bioactive protein or polypeptide in the periplasm of E. coli, the method comprising introducing an expression vector into E. coli,
wherein the expression vector comprises (a) a promoter, (b) a first nucleic acid sequence encoding a heavy chain portion (Fd) of an antigen binding fragment (Fab), (c) a second nucleic acid sequence encoding a light chain of the Fab, and (d) a third nucleic acid sequence encoding the bioactive protein or polypeptide and optionally a linker,
wherein the first nucleic acid sequence and the second nucleic acid sequence are in a sequential order, wherein the first nucleic acid sequence is followed by the second nucleic acid sequence or the second nucleic acid sequence is followed by the first nucleic acid sequence,
wherein the promoter, the first nucleic acid sequence, the second nucleic acid sequence, and the third nucleic acid sequence are operably linked,
wherein at least one cysteine of the heavy chain constant 1 domain (CH1 domain) of the Fab or the light chain constant domain (CκL domain) of the Fab is deleted or substituted with a serine residue and, wherein the E. coli is SUPEX5 (KCTC Accession No: KCTC 12657BP).

2. The method of claim 1, wherein the third nucleic acid sequence is fused to the first nucleic acid sequence in-frame.

3. The method of claim 1, wherein the third nucleic acid sequence is fused to the second nucleic acid sequence in-frame.

4. The method of claim 1, wherein the bioactive protein or polypeptide is one selected from the group consisting of hormone, cytokine, enzyme, antibody, growth factor, transcription factor, blood factor, vaccine, ligand protein, and receptor.

5. The method of claim 1, wherein the bioactive protein or polypeptide is one selected from the group consisting of human growth hormone (hGH), growth hormone releasing hormone (GHRH), growth hormone releasing peptide, interferons (IFNs), interferon receptors, colony stimulating factors (CSFs), glucagon-like peptides, G-protein-coupled receptors, interleukins, interleukin receptors, enzymes, interleukin binding proteins, cytokine binding proteins, macrophage activating factor, macrophage peptide, B cell factor, T cell factor, protein A, cell necrosis glycoproteins, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, virus derived vaccine antigens, antibodies, and antibody fragments.

6. A method of increasing soluble expression of a bioactive protein or polypeptide in the periplasm of E. coli, the method comprising introducing an expression vector into E. coli,
wherein the expression vector comprises (a) a promoter, (b) a first nucleic acid sequence encoding a heavy chain portion (Fd) of an antigen binding fragment (Fab), (c) a second nucleic acid sequence encoding a light chain of the Fab, and (d) a third nucleic acid sequence encoding a linker and the bioactive protein or polypeptide and optionally a linker,
wherein the first nucleic acid sequence and the second nucleic acid sequence are in a sequential order, wherein the first nucleic acid sequence is followed by the second nucleic acid sequence or the second nucleic acid sequence is followed by the first nucleic acid sequence,
wherein the promoter, the first nucleic acid sequence, the second nucleic acid sequence, and the third nucleic acid sequence are operably linked,
wherein at least one of amino acid cysteine of the heavy chain constant 1 domain (CH1 domain) of the Fab or the light chain constant domain (CκL domain) of the Fab is deleted or substituted with a serine residue, and
wherein the Fab specifically binds to human serum albumin, and the Fab comprises: (i) a heavy chain variable domain (VH domain) having an amino acid sequence selected from the group consisting of SEQ ID NO: 1, SEQ ID NO: 2, SEQ ID NO: 3, SEQ ID NO: 4, SEQ ID NO: 5 and SEQ ID NO: 6; and (ii) a light chain variable domain (VL domain) having an amino acid sequence selected from the group consisting of SEQ ID NO: 7, SEQ ID NO: 8, SEQ ID NO: 9, SEQ ID NO: 10, SEQ ID NO: 11 and SEQ ID NO: 12.

7. A method of increasing soluble expression of a bioactive protein or polypeptide in the periplasm of *E. coli*, the method comprising introducing an expression vector into *E. coli*,
wherein the expression vector comprises (a) a promoter, (b) a first nucleic acid sequence encoding a heavy chain portion (Fd) of an antigen binding fragment (Fab), (c) a second nucleic acid sequence encoding a light chain of the Fab, and (d) a third nucleic acid sequence encoding a linker and the bioactive protein or polypeptide and optionally a linker,
wherein the first nucleic acid sequence and the second nucleic acid sequence are in a sequential order, wherein the first nucleic acid sequence is followed by the second nucleic acid sequence or the second nucleic acid sequence is followed by the first nucleic acid sequence,
wherein the promoter, the first nucleic acid sequence, the second nucleic acid sequence, and the third nucleic acid sequence are operably linked,
wherein at least one of amino acid cysteine of the heavy chain constant 1 domain (CH1 domain) of the Fab or the light chain constant domain (CκL domain) of the Fab is deleted or substituted with a serine residue, and
wherein the Fab specifically binds to human serum albumin, and the Fab comprises: (i) the amino acid sequences of SEQ ID NOS: 13 (CDR1), 14 (CDR2) and 15 (CDR3) determining the CDRs of a heavy chain variable domain (VH domain); and (ii) the amino acid sequences of SEQ ID NOS: 16 (CDR1), 17 (CDR2) and 18 (CDR3) determining the CDRs of a light chain variable domain (VL domain).

8. A method of increasing the in vivo half-life of a bioactive protein or polypeptide, comprising genetically fusing the bioactive protein or polypeptide to an antigen binding fragment (Fab),
wherein the Fab specifically binds to human serum albumin, and the Fab comprises: (i) a heavy chain variable domain (VH domain) having an amino acid sequence selected from the group consisting of SEQ ID NO: 1, SEQ ID NO: 2, SEQ ID NO: 3, SEQ ID NO: 4, SEQ ID NO: 5 and SEQ ID NO: 6; and (ii) a light chain variable domain (VL domain) having an amino acid sequence selected from the group consisting of SEQ ID NO: 7, SEQ ID NO: 8, SEQ ID NO: 9, SEQ ID NO: 10, SEQ ID NO: 11 and SEQ ID NO: 12.

9. The method of claim 8, wherein the bioactive protein or polypeptide is linked to the Fab by a peptide linker of 1 to 20 amino acids.

10. The method of claim 8, wherein the bioactive protein or polypeptide is one selected from the group consisting of human growth hormone (hGH), growth hormone releasing hormone (GHRH), growth hormone releasing peptide, interferons (IFNs), interferon receptors, colony stimulating factors (CSFs), glucagon-like peptides, G-protein-coupled receptors, interleukins, interleukin receptors, enzymes, interleukin binding proteins, cytokine binding proteins, macrophage activating factor, macrophage peptide, B cell factor, T cell factor, protein A, cell necrosis glycoproteins, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, virus derived vaccine antigens, antibodies, and antibody fragments.

11. A method of increasing the in vivo half-life of a bioactive protein or polypeptide, the method comprising genetically fusing the bioactive protein or polypeptide to an antigen binding fragment (Fab),
wherein the Fab specifically binds to human serum albumin, and the Fab comprises: (i) the amino acid sequences of SEQ ID NOS: 13 (CDR1), 14 (CDR2) and 15 (CDR3) determining the CDRs of a heavy chain variable domain (VH domain); and (ii) the amino acid sequences of SEQ ID NOS: 16 (CDR1), 17 (CDR2) and 18 (CDR3) determining the CDRs of a light chain variable domain (VL domain).

12. The method of claim 11, wherein the bioactive protein or polypeptide is linked to the Fab by a peptide linker of 1 to 20 amino acids.

13. The method of claim 11, wherein the bioactive protein or polypeptide is one selected from the group consisting of human growth hormone (hGH), growth hormone releasing hormone (GHRH), growth hormone releasing peptide, interferons (IFNs), interferon receptors, colony stimulating factors (CSFs), glucagon-like peptides, G-protein-coupled receptors, interleukins, interleukin receptors, enzymes, interleukin binding proteins, cytokine binding proteins, macrophage activating factor, macrophage peptide, B cell factor, T cell factor, protein A, cell necrosis glycoproteins, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, virus derived vaccine antigens, antibodies, and antibody fragments.

14. A method of expressing a recombinant protein in *E. coli*, the method comprising introducing an expression vector comprising a nucleic acid sequence encoding said recombinant protein into the recombinant *E.coli* SUPEX5 (KCTC Accession No: KCTC 12657BP).

15. The method of claim 14, wherein the expression vector comprises the sequence of SEQ ID NO: 110.

16. The method of claim 14, wherein the method increases soluble expression of said recombinant protein in the periplasm of *E. coli* SUPEX5.

* * * * *